United States Patent [19]
Ozaki et al.

[11] Patent Number: 5,716,993
[45] Date of Patent: Feb. 10, 1998

[54] ANTHRANILIC ACID DERIVATIVES

[75] Inventors: Fumihiro Ozaki; Keiji Ishibashi; Hironori Ikuta; Hiroki Ishihara; Shigeru Souda, all of Ibaraki, Japan

[73] Assignee: Eisai Co., Ltd., Japan

[21] Appl. No.: 507,476

[22] PCT Filed: Dec. 27, 1994

[86] PCT No.: PCT/JP94/02262

§ 371 Date: Sep. 16, 1995

§ 102(e) Date: Sep. 16, 1995

[87] PCT Pub. No.: WO95/18097

PCT Pub. Date: Jul. 6, 1995

[30] Foreign Application Priority Data

Dec. 27, 1993 [JP] Japan .................................. 5-347092
Oct. 9, 1994 [JP] Japan .................................. 6-299110

[51] Int. Cl.[6] .................................................. A61K 31/165
[52] U.S. Cl. .......................... 514/619; 544/253; 544/321;
544/337; 544/351; 544/329; 544/468; 544/406;
544/428; 544/603; 549/441; 548/364.4;
548/568; 564/86; 564/168; 564/184; 546/197;
546/226; 546/283.9; 546/284.1; 546/300
[58] Field of Search .......................... 549/441; 514/351,
514/466, 253, 321, 337, 329, 428, 406,
468, 603, 619; 546/300, 197, 226, 283.7,
284.1; 548/568, 364.4; 564/184, 86, 168;
544/337

[56] References Cited

FOREIGN PATENT DOCUMENTS 632153  10/1963  Belgium.
0 371 731  6/1990  European Pat. Off..

OTHER PUBLICATIONS

Database Crossfire—Beilstein Informationssysteme GmbH, Frankfurt DE *see BRN=1910632* & J. Chem. Soc., 1932, pp. 2728–2729.

Database Crossfire—Beilstein Informationssysteme GmbH, Frankfurt, DE *BRN=471803* & J. Chem. Soc., 1928, p. 539.

Database Crossfire—Beilstein Informationssysteme GmbH, Frankfurt, DE *BRN=639027* & J. Amer. Chem.Soc., vol. 76, 1954, pp. 6336–6337.

Journal of the Heterocyclic Chemicstry, vol. 12, No. 3, Jun. 1975 Provo US, pp. 565–572, G. E. Hardtmann et al., "The Chemistry of 2H-3,1-Benzoxazine-2,4(1H)dione (Isatoic Anhydrides) 1. The Synthesis of N-substituted 2H-3, 1-Benzoxazine-2,4(1H)diones" *p. 568, compound 48; p. 569, compounds of 59–61, 65–69; p. 570, compounds 70–87.

*Primary Examiner*—Amelia Owens
*Attorney, Agent, or Firm*—Nixon & Vanderhye

[57] ABSTRACT

The present invention provides an anthranilic acid derivative having a cGMP-PDE inhibitory activity.

An anthranilic acid derivative represented by the general formula (I) or a pharmacologically acceptable salt thereof:

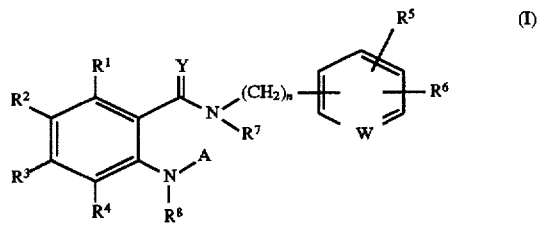

[wherein $R^1$, $R^2$, $R^3$ and $R^4$ represent the same or different from each other, a hydrogen atom, a halogen atom, a hydroxy group, an optionally halogenated lower alkyl group, an optionally halogenated lower alkoxy group, a nitro group, a hydroxyalkyl group, a cyano group or the like; $R^5$ and $R^6$ represent the same or different from each other, a hydrogen atom, a halogen atom, a hydroxy group, a cyano group, an optionally halogenated lower alkyl group, an optionally halogenated lower alkoxy group or the like;

W represents a group of the formula: —N= or —CH=; $R^7$ and $R^8$ represent the same or different from each other, a hydrogen atom, an optionally halogenated lower alkyl group or the like;

A represents a hydrogen atom, an optionally halogenated lower alkyl group or the like;

Y represents an oxygen atom or a sulfur atom; and n is an integer of 0 to 6].

7 Claims, No Drawings

ANTHRANILIC ACID DERIVATIVES

FIELD OF THE INVENTION

The present invention relates to an anthranilic acid derivative having an excellent activity as a drug.

BACKGROUND OF THE INVENTION AND PRIOR ART

Angina pectoris which is one of ischemic heart diseases has been known as a disease which frequently attacks the aged. Although nitrate and nitrite compounds, calcium antagonist, β-blocker and so forth have been used as remedies therefor, these drugs are still insufficiently effective in treating angina pectoris or in preventing the evolution thereof into myocardial infarction. Further, there have recently been observed lowering in the age of patient with angina pectoris and complication of condition of the patient owing to the change in life style and the stress increased by the complication of social mechanism, so that the development of a new type of more excellent drug has been eagerly expected.

With respect to the nitrate and nitrite compounds among the above-mentioned drugs currently used, it is believed that the action thereof relates to cyclic GMP (hereinafter abbreviated to "cGMP") which is one of the cyclic nucleotides known as intracellular second messenger. Further, it is well known that cGMP has a relaxant activity on vascular and bronchial smooth muscles. Although the mechanism of action of these drug is not always apparent, the above activity of cGMP is generally believed to be due to the synthesis of cGMP accelerated by an activated guanylate cyclase. However, these drugs exhibit low bioavailability and relatively short action time, and the occurrence of tolerance thereto has been reported, which becomes a clinical problem.

DISCLOSURE OF THE INVENTION

Under these circumstances, the inventors of the present invention started studies to develop a new type of more excellent drug.

Namely, the inventors of the present invention have directed their attention to an inhibitory activity against cGMP phosphodiesterase (hereinafter abbreviated to "cGMP-PDE") and have intensively studied on compounds having such an activity for many years. As a result of the studies, they have found that an anthranilic acid derivative which will be described below has these activity and is efficacious for various ischemic heart diseases. The present invention has been accomplished on the basis of this finding.

The present invention relates to an anthranilic acid derivative represented by the following general formula (I) or a pharmacologically acceptable salt thereof:

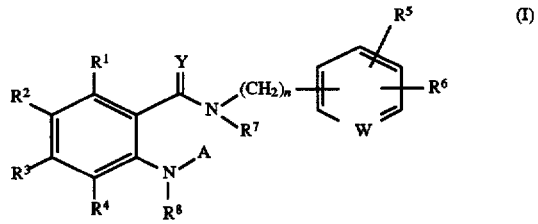

[wherein $R^1$, $R^2$, $R^3$ and $R^4$ represent the same or different from each other, a hydrogen atom, a halogen atom, a hydroxy group, an optionally halogenated lower alkyl group, an optionally halogenated lower alkoxy group, a nitro group, a hydroxyalkyl group, a cyano group, a group of the formula:

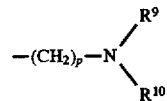

(wherein $R^9$ and $R^{10}$ represent the same or different from each other, a hydrogen atom, an optionally halogenated lower alkyl group, an arylalkyl group, a heteroarylalkyl group, an acyl group or an optionally protected carboxyl group, or alternatively $R^9$ and $R^{10}$ together with the nitrogen atom to which they are bonded may form a ring which may be substituted; and p is an integer of 0 to 6), an optionally substituted tetrazolyl group, an optionally protected carboxyl group, an optionally substituted carbamoyl group, an optionally substituted pyrazolyl group, an optionally substituted imidazolyl group, a group of the formula:

(wherein $R^{13}$ represents a hydrogen atom or an optionally halogenated lower alkyl group; and q is an integer of 0 to 2), or alternatively two substituents selected from among $R^1$, $R^2$, $R^3$ and $R^4$ which are adjacent to each other may form a ring together with the carbon atoms to which they are bonded respectively;

$R^5$ and $R^6$ represent the same or different from each other, a hydrogen atom, a halogen atom, a hydroxy group, a cyano group, an optionally halogenated lower alkyl group or an optionally halogenated lower alkoxy group; or alternatively $R^5$ and $R^6$ together with the carbon atoms to which they are bonded respectively may form a cycloalkyl ring, an oxolane ring, a 1,3-dioxolane ring or a 1,4-dioxane ring;

W represents a group of the formula: —N= or —CH=;
$R^7$ and $R^8$ represent the same or different from each other, a hydrogen atom or an optionally halogenated lower alkyl group, or alternatively $R^7$ and $R^8$ together with the carbon atoms to which they are bonded respectively may form a ring which may contain a nitrogen atom, an oxygen atom or a sulfur atom and which may be substituted;

A represents a hydrogen atom, an optionally halogenated lower alkyl group or a group of the formula: —X—(CH$_2$)$_m$—Z (wherein X represents the formula: —CO—, —CS—, —CH$_2$— or —S(O)$_2$—;

Z represents a hydroxy group, an optionally halogenated lower alkoxy group, a cyano group, a halogen atom, an optionally protected carbamoyl group, an optionally substituted aryl group, an optionally substituted aryloxy group, an optionally substituted heteroaryl group, an optionally substituted heteroarylalkyloxy group, a group of formula: —NR$^{11}$R$^{12}$ (wherein R$^{11}$ and R$^{12}$ represent the same or different from each other, a hydrogen atom, an optionally halogenated lower alkyl group, an optionally substituted arylalkyl group, an optionally substituted heteroarylalkyl group, an acyl group, an optionally protected carboxy group or optionally substituted carbamoyl group, or alternatively R$^{11}$ and R$^{12}$ together with the nitrogen atom to which they are bonded may form a ring which may be substituted), or an optionally substituted cycloalkyl group; and m is an integer of 0 to 6);

Y represents an oxygen atom or a sulfur atom; and n is an integer of 0 to 6].

Anthranilic acid is o-aminobenzoic acid and the anthranilamide structure is essential structure to the compounds of the present invention.

In the above definition of the general formula (I), the lower alkyl group consisting the optionally halogenated lower alkyl as defined with respect to $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is a linear or branched alkyl group having 1 to 6 carbon atoms, and examples thereof include methyl, ethyl, n-propyl, n-butyl, isopropyl, isobutyl, 1-methyl-propyl, tert-butyl, n-pentyl, 1-ethylpropyl, isoamyl and n-hexyl. Further, the term "optionally halogenated" means "substituted with one or more halogen atoms at any carbon atom(s) constituting the above lower alkyl group". Examples of the halogenated a lower alkyl include trifluoromethyl group and a 2,2-dichloroethyl group. The most desirable examples of the optionally halogenated lower alkyl include a methyl group, an ethyl group or a trifluoromethyl group.

The hydroxyalkyl as defined with respect to $R^1$, $R^2$, $R^3$ and $R^4$ is a group composed of a lower alkyl group described above and a hydroxy group bonded to any carbon atom thereof.

The cycloalkyl group as defined with respect to $R^{11}$ and $R^{12}$ is one having 3 to 8 carbon atoms, preferably 5 or 6 carbon atoms.

The optionally halogenated lower alkoxy as defined with respect to $R^1$, $R^2$, $R^3$, $R^4$, $R^5$, $R^6$, $R^9$, $R^{10}$, $R^{11}$ and $R^{12}$ is one derived from the above optionally halogenated lower alkyl group, and examples thereof include lower alkoxy groups such as a methoxy group and an ethoxy group; a trifluoromethyloxy group and a 2,2-dichloroethyloxy group.

The substituent constituting the "optionally substituted tetrazolyl", "optionally substituted pyrazolyl" or "optionally substituted imidazolyl" as defined with respect to $R^1$, $R^2$, $R^3$ and $R^4$ includes lower alkyl groups such as methyl, ethyl and t-butyl; lower alkyl groups substituted with one or more optionally substituted phenyl groups such as p-methoxybenzyl, p-nitrobenzyl, 3,4-dimethoxybenzyl, diphenylmethyl, trityl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbohyloxymethyl, 1-butoxycarbonyl-oxyethyl and 1-(isopropoxycarbonyloxy) ethyl; carboxy lower alkyl groups such as carboxymethyl and 2-carboxyethyl; heterocyclic groups such as 3-phthalidyl; optionally substituted benzoyloxy lower alkyl groups such as 4-glycyloxybenzoyloxymethyl and 4-[N-(t-butoxycarbonyl)glycyloxy]benzoyloxymethyl; (substituted dioxolene) lower alkyl groups such as (5-methyl-2-oxo-1,3-dioxolen-4-yl)methyl; cycloalkyl-substituted lower alkanoyloxy lower alkyl groups such as 1-cyclohexylacetyloxyethyl; and cycloalkyloxycarbonyloxy lower alkyl groups such as 1-cyclohexyloxycarbonyloxyethyl.

The protecting group constituting the optionally protected carboxy as defined with respect to $R^1$, $R^2$, $R^3$, $R^4$, $R^{11}$, $R^{12}$ and Z includes lower alkyl groups such as methyl, ethyl and t-butyl; lower alkyl groups substituted with optionally substituted phenyl groups such as p-methoxybenzyl, p-nitrobenzyl, 3,4-dimethoxybenzyl, diphenylmethyl, trityl and phenethyl; halogenated lower alkyl groups such as 2,2,2-trichloroethyl and 2-iodoethyl; lower alkanoyloxy lower alkyl groups such as pivaloyloxymethyl, acetoxymethyl, propionyloxymethyl, butyryloxymethyl, valeryloxymethyl, 1-acetoxyethyl, 2-acetoxyethyl, 1-pivaloyloxyethyl and 2-pivaloyloxyethyl; higher alkanoyloxy lower alkyl groups such as palmitoyloxyethyl, heptadecanoyloxymethyl and 1-palmitoyloxyethyl; lower alkoxycarbonyloxy lower alkyl groups such as methoxycarbonyloxymethyl, 1-butoxycarbonyloxyethyl and 1-(isopropoxycarbonyloxy)ethyl; carboxy lower alkyl groups such as carboxymethyl and 2-carboxyethyl; heterocyclic groups such as 3-phthalidyl; optionally substituted benzoyloxy lower alkyl groups such as 4-glycyloxybenzoyloxymethyl and 4-[N-(t-butoxycarbonyl) glycyloxy]benzoyloxymethyl; (substituted dioxolene) lower alkyl groups such as (5-methyl-2-oxo-1,3-dioxolen-4-yl) methyl; cycloalkyl-substituted lower alkanoyloxy lower alkyl groups such as 1-cyclohexylacetyloxyethyl; and cycloalkyloxycarbonyloxy lower alkyl groups such as 1-cyclohexycoxylcarbonyloxyethyl.

Further, the protected group may be one of various acid amides, as far as it can be decomposed into a carboxyl group in vivo.

The acyl group as defined with respect to $R^1$, $R^2$, $R^3$, $R^4$, $R^5$, $R^9$, $R^{10}$, $R^{11}$ and $R^{12}$ includes those groups derived from aliphatic saturated monocarboxylic acids such as formyl, acetyl, propionyl and butyryl; those groups derived from aliphatic unsaturated carboxylic acids such as an acryloyl group, a propioloyl group, a methacryloyl group, a crotonoyl group, an isocrotonoyl group, an oleoyl group and an elaidoyl group; those groups derived from carbocyclic carboxylic acids such as a benzoyl group, a naphthoyl group, a toluoyl group, a hydratropoyl group and a cinnamoyl group; those groups derived from heterocyclic carboxylic acids such as furoyl, thenoyl, nicotinoyl and isonicotinoyl; and those groups derived from hydroxy carboxylic acids and alkoxy carboxylic acids such as a glycoloyl group, a lactoyl group, a glyceroyl group, a tropoyl group, a salicyloyl group, a veratroyl group, an anisoyl group and a galloyl group.

The above definition with respect to $R^9$ and $R^{10}$ or $R^{11}$ and $R^{12}$ that "$R^9$ and $R^{10}$ (or $R^{11}$ and $R^{12}$) together with the nitrogen atom to which they are bonded may form a ring" means that they may together form a piperidine ring or a pyrrolidine ring.

Further, the above definition with respect to $R^1$ and $R^7$ that "$R^1$ and $R^7$ together with the carbon atoms to which they are bonded respectively may form a ring which may contain nitrogen, oxygen or sulfur" means that $R^1$ and $R^7$ may together form a ring condensed with the benzene ring to which $R^1$ is bonded. Examples of the ring include piperidine, pyrrolidine, oxane, 1,3-dioxane and 1,4-dioxolane rings.

The optionally substituted aryl group as defined with respect to Z includes a phenyl group, a naphthyl group and an anthranyl group.

The optionally substituted heteroaryl group as defined with respect to Z includes a pyridyl group, a pyrrolyl group, an imidazolyl group, a pyrazolyl group, a pyridazyl group, a pyrimidyl group, a pydidazyl group, a furanyl group, a pyranyl group, a thienyl group, an isothiazolyl group, a furazanyl group, a quinazolyl group, an indolyl group, a quinolyl group and a pyrazolidinyl group, though it is not limited to them.

The aryl group constituting the optionally substituted arylalkyl as defined with respect to $R^9$, $R^{10}$, $R^{11}$, $R^{12}$, $R^{14}$ and Z is the same as defined above. Further, the alkyl group constituting it may be one derived from the above lower alkyl. In the arylalkyl group, one to three aryl groups may be bonded to any carbon atoms of the alkyl group.

The heteroaryl constituting the optionally substituted heteroarylalkyl group as defined with respect to $R^9$, $R^{10}$, $R^{11}$, $R^{12}$ and Z is the same as defined above. The alkyl constituting it is a group derived from the above lower alkyl group. In the heteroarylalkyl, one to three heteroaryls may be bonded to any carbon atoms of the alkyl group.

The optionally substituted aryloxy group as defined with respect to Z is one derived from the above aryl, for example, phenoxy or naphthyloxy.

The heteroaryloxy group as defined with respect to Z is one derived from the above heteroaryl group.

Further, "the substituent" constituting the "an optionally substituted aryl group", "an optionally substituted heteroaryl group", "an optionally substituted arylalkyl group", "an optionally substituted heteroarylalkyl group", "an optionally substituted aryloxy group", "an optionally substituted heteroaryloxy group", "an optionally substituted carbamoyl group", "the substituent" which ring which may be substituted that is formed by $R^9$, $R^{10}$ and the nitrogen atom to which they are bonded has, "the substituent" which ring which may be substituted that is formed by $R^{11}$, $R^{12}$ and the nitrogen atom to which they are bonded has, and "the substituent" which ring which may be substituted that is formed by $R^1$, $R^7$ and the carbon atoms to which they are bonded has respectively includes a hydroxy group; a cyano group; an amino group; a nitro group; halogen atoms such as a chlorine atom, a fluorine atom, a bromine atom and an iodine atom; lower alkyl groups such as methyl, ethyl and t-butyl; lower alkoxy groups such as methoxy, ethoxy and t-butoxy; an optionally protected carboxyl group; a hydroxyalkyl group; a carboxyalkyl group; a tetrazolyl group and so forth.

Further, as described above, "$R^4$ and $R^5$ together with the nitrogen atom to which they are bonded may form a ring which may be substituted", and the substituent represents the same as defined above.

The halogen atom as defined with respect to $R^6$, $R^7$ and Z includes a fluorine atom, a chlorine atom, a bromine atom and an iodine atom.

The pharmacologically acceptable salt according to the present invention includes inorganic acid salts such as hydrochloride, sulfate, hydrobromide and phosphate; and organic acid salts such as formate, acetate, trifluoroacetate, maleate, fumarate, tartrate, methanesulfonate, benzenesulfonate and toluenesulfonate.

Some compounds according to the present invention form hydrates and it is needless to say that these hydrates fall within the scope of the present invention.

Y is preferably an oxygen atom.

Main processes for the production of the compound of the present invention will now be described.

Preparation process 1

A compound represented by the general formula (I) wherein Y is an oxygen atom can be prepared by the following process:

(IIIa)

(V)

(Ia)

(wherein $R^1$ to $R^8$, A and n are each as defined above)

Accordingly, this process is a process that an anthranilic acid derivative represented by the general formula (Ia) can be prepared by condensing an anthranilic acid derivative represented by the general formula (IIIa) with an amine represented by the general formula (V) in a conventional manner.

Although this condensation can be conducted in a conventional manner, the use of a condensing agent is preferable.

The condensing agent to be used in this process may be any conventional one and examples thereof include N,N'-dicyclohexylcarbodiimlde, N-ethyl-N'-(3-dimethylaminopropyl)carbodiimide, and 2-ethoxy-1-ethoxycarbonyl-1,2-dihydroquinoline.

The condensation can be accelerated by the coexistence of N-hydroxysuccinimide or N-hydroxybenztriazole.

The solvent to be used in the above condensation may be any organic one inert to water and the condensation. Examples of such a solvent include ethers such as ether, tetrahydrofuran and 1,4-dioxane; hydrocarbons such as benzene, toluene and xylene; dichloromethene, chloroform, 1,2-dichloroethane, acetonitrile, N,N-dimethylformamide and pyridine.

The reaction temperature may range from about 0° C. to the refluxing temperature of the solvent.

Preparation process 2

A compound represented by the general formula (I) wherein A is a group of the formula: —CO—(CH$_2$)$_m$— Z (wherein Z and m are each as defined above) can be prepared also by the following process:

(VII)

Hal—X—(CH$_2$)$_m$—Z ⟶

(VI)

-continued

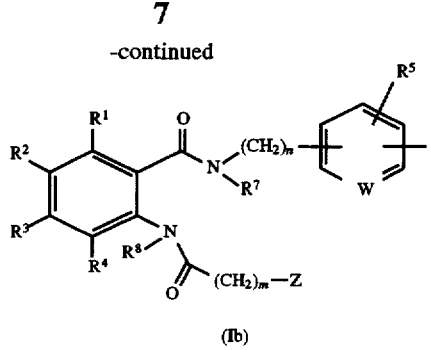

(Ib)

(wherein $R^1$ to $R^8$, m, n and Z are each as defined above).

Accordingly, this is a process that an objective compound represented by the general formula (Ib) can be prepared by reacting a compound represented by the general formula (VI) with an anthranilic acid derivative represented by the general formula (VII).

The solvent to be used in this reaction may be any organic one inert to the reaction, and examples thereof include ethers such as ether, tetrahydrofuran and 1,4-dioxane; hydrocarbons such as benzene, toluene and xylene; dichloromethane, chloroform, 1,2-dichloro-ethane, acetonitrile, N,N-dimethylformamide and pyridine.

The reaction temperature may range from about −20° C. to the refluxing temperature of the solvent.

The reaction can be accelerated by the use of an organic base such as triethylamine, diisopropyl-ethylamine or lutidine; or an inorganic base such as sodium hydrogencarconate, sodium carbonate, potassium carbonate or sodium hydroxide.

Preparation process 3

A compound represented by the general formula (I) wherein Z is a carboxyl group can be prepared by the following process:

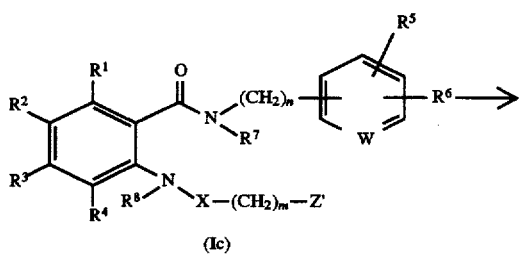

(Ic)

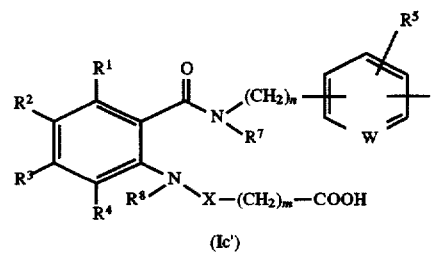

(Ic')

(wherein $R^1$ to $R^8$, m and n are each as defined above; and Z' represents a protected carboxyl group)

Accordingly, this is a process that an objective compound represented by the general formula (Ic') can be prepared by the hydrolysis of a compound represented by the general formula (Ic).

The solvent to be used in the hydrolysis may be any organic one inert to the hydrolysis, and examples thereof include alcohols such as methanol and ethanol; and ethers such as tetrahydrofuran and 1,4-dioxane.

The reaction temperature preferably ranges from about 0° C. to the refluxing temperature of the solvent.

Further, the existence of an inorganic base in the hydrolysis gives desirable results, and example of the base include lithium hydroxide, sodium hydroxide, potassium hydroxide and barium hydroxide.

Preparation process 4

A compound represented by the general formula (I) wherein Z is represented by the formula: —$NR^{11}R^{12}$ can be prepared also by the following process:

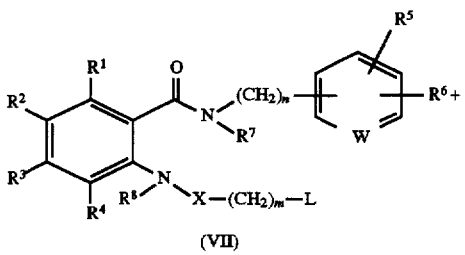

(VII)

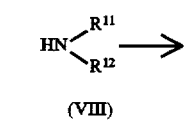

(VIII)

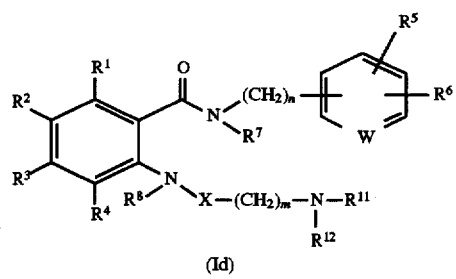

(Id)

(wherein $R^1$ to $R^8$, $R^{11}$, $R^{12}$, n and m are each as defined above; and L represents a leaving group such as a halogen atom, a p-toluenesulfonyloxy group or a methanesulfonyloxy group).

Accordingly, this is a process that an objective compound represented by the general formula (Id) can be prepared by reacting a compound represented by the general formula (VII) with an amine represented by the general formula (VIII).

The solvent to be used in the above reaction includes ethers such as ether, tetrahydrofuran and 1,4-dioxane; alcohols such as methanol and ethanol; dichloromethane; chloroform; 1,2-dichloroethane; acetonitrile; N,N-dimethylformamide; and dimethyl sulfoxide.

The reaction temperature preferably ranges from about 0° C. to the refluxing temperature of the solvent.

Preparation Process 5

A compound represented by the general formula (I) wherein $R^8$ is hydrogen and X is reprresented by the formula: —$CH_2$— can be prepared by the following process:

(IV)

(V)

(Ie)

(wherein R¹ to R⁷, m, n and Z are each as defined above).

Accordingly, this is a process that an objective compound represented by the general formula (Ie) can be prepared by reacting a compound represented by the general formula (IV) with a compound represented by the general formula (V).

The above reaction may be conducted in a solvent inert to the reaction, and examples of such a solvent include ethers such as ether, tetrahydrofuran and 1,4-dioxane; hydrocarbons such as benzene, toluene and xylene; acetonitrile; N,N-dimethylformamide; dimethyl sulfoxide; dichloromethane; chloroform; and 1,2-dichloroethane.

The reaction temperature preferably ranges from about 0° C. to the refluxing temperature of the solvent.

Further, the use of a catalytic amount of a base in the reaction gives desirable results and examples of the base include 4-dimethylaminopyridine and 4-pyrrolidinopyridine.

Preparation process 6

A compound represented by the general formula (I) wherein $R^8$ and A are each a hydrogen atom can be prepared also by the following process:

(If)

(If)

(wherein R¹ to R⁷ and n are each as defined above).

Accordingly, this is a process that an objective compound represented by the general formula (If) can be prepared by reducing a compound represented by the general formula (If') in a conventional manner.

This reduction can be conducted by any conventional process and examples of the process include catalytic reduction with palladium/carbon or platinum oxide, or reduction using a metal (such as iron, tin or zinc), reduction using an acid (such as hydrochloric or acetic acid) and reduction using stannic chloride.

The solvent to be used in the above reduction may be one inert to the reduction, for example, methanol or ethanol.

The reaction temperature preferably ranges from about 0° C. to the refluxing temperature of the solvent.

Preparation Process 7

A compound represented by the general formula (IIIa) which is the starting material of Preparation process 1 can be prepared by the following process:

(III)        (IIIa)

(wherein $R^1$ to $R^4$, $R^8$ and A are each as defined above; and $R^{14'}$ represents a group selected from among those defined with respect to $R^{14}$ except hydrogen atoms).

Accordingly, a compound represented by the general formula (IIIa) can be prepared by deblocking a compound represented by the general formula (III).

When $R^{14}$ is alkyl, it is preferable that a solvent inert to the deblocking (such as methanol, ethanol, tetrahydrofuran or 1,4-dioxane) be used in the presence of a base such as lithium hydroxide, sodium hydroxide, potassium hydroxide or barium hydroxide at a temperature ranging from about 0° C. to the refluxing temperature of the solvent.

When $R^{14}$ is benzyl, a compound represented by the general formula (IIIa) can be prepared by catalytic reduction using palladium/carbon or the like as the catalyst.

Further, when $R^{14}$ is 4-methoxybenzyl, benzhydryl or the like, the deblocking can be conducted by the use of trifluoroacetic acid in a solvent such as dichloromethane, chloroform or 1,2-dichloroethane in the presence of anisole. In this case, it is preferable that the reaction temperature range from about 0° C. to the refluxing temperature of the solvent.

Preparation process 8

A compound represented by the general formula (III) wherein X is represented by the formula: —CO—; m is 0; and $R^8$ is a hydrogen atom, which is the starting material of Preparation process 7, can be prepared by the following process:

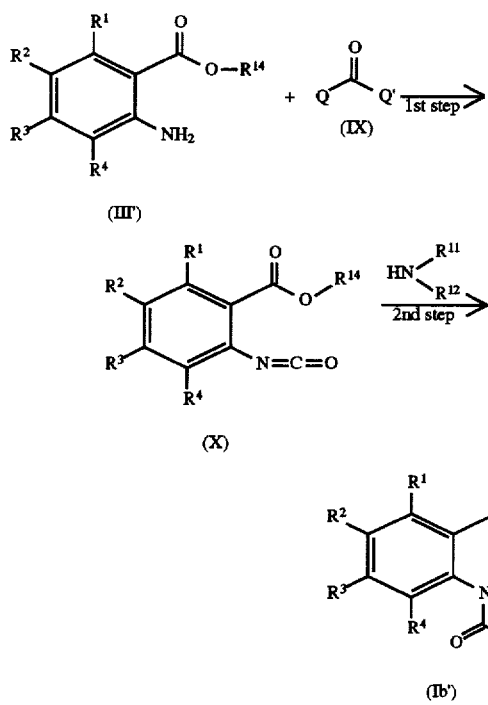

(III')

(X)

(Ib')

(wherein Q and Q' each represent a chlorine atom, a trichloromethoxy group or an imidazolyl group; and $R^1$ to $R^4$ and $R^{11}$ to $R^{13}$ are each as defined above).

(1st step)

Accordingly, this step is that a compound represented by the general formula (X) is prepared by reacting a compound represented by the general formula (III') with a compound represented by the general formula (IX).

In carrying out the above reaction, a solvent inert to the reaction may be used, and examples of the solvent include ether, tetrahydrofuran, 1,4-dioxane, dichloromethane, chloroform, 1,2-dichloroethane, benzene, toluene and xylene.

The reaction temperature preferably ranges from about 0° C. to the refluxing temperature of the solvent.

If necessary, a base such as triethylamine or diisopropylethylamine may be used in carrying out the above reaction to make the reaction proceed smoothly.

The compound (X) prepared in this step may be used in the following 2nd step without being isolated.

(2nd step)

This step is a step that a compound represented by the general formula (Ib) is prepared by reacting the compound (X) prepared in the above 1st step with a compound represented by the general formula (VIII). The reaction temperature preferably ranges from about 0° C. to the refluxing temperature of the solvent.

Preparation process 9

Among the anthranilic acid derivatives (III') as the starting material of Preparation process 8, an anthranilic derivative of free carboxyl group (IIa') can be prepared by the following process:

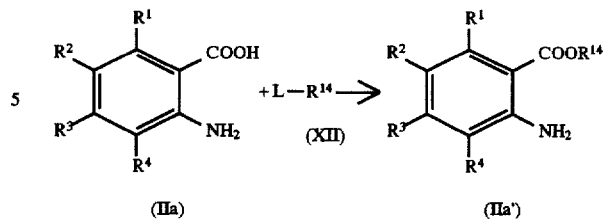

(IIa)  (IIa')

(wherein $R^1$ to $R^4$ and $R^{14}$ are each as defined above).

Accordingly, this process is that a compound represented by the general formula (IIa') can be prepared by reacting a compound represented by the general formula (IIa) with a compound represented by the general formula (XII).

The reaction is preferably conducted in a solvent such as N,N-dimethylformamide, acetonitrile, benzene, toluene, xylene, dichloromethane, chloroform, 1,2-dichloroethane, tetrahydrofuran or 1,4-dioxane in the presence of a base such as sodium hydrogen-carbonate, sodium carbonate, potassium carbonate or cesium carbonate at a temperature ranging from about 0° C. to the refluxing temperature of the solvent.

Preparation process 10

A compound represented by the general formula (VII) which is the starting material of Preparation process 4 can be prepared by the following process:

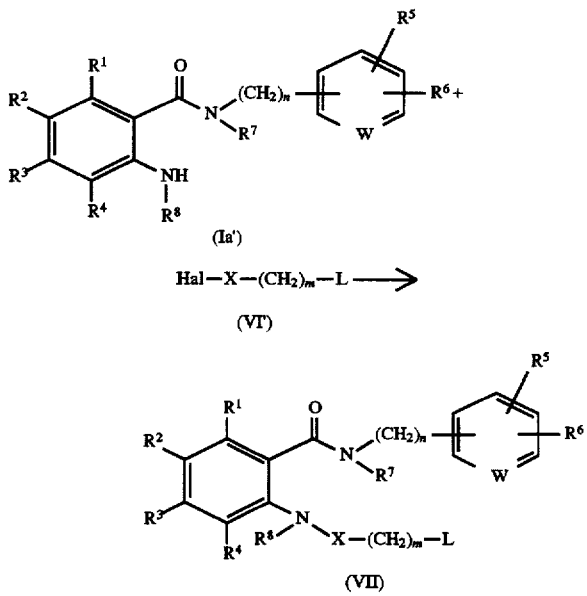

(Ia')

Hal—X—(CH₂)ₘ—L ⟶

(VI')

(VII)

(wherein Hal represents a halogen atom; L represents a leaving group such as a halogen atom, a p-toluenesulfonyloxy group or a methanesulfonyloxy group; and $R^1$ to $R^8$, m, n and X are each as defined above).

Accordingly, this is a process that a compound represented by the general formula (Id') can be prepared by reacting a compound represented by the general formula (Ia') with a compound represented by the general formula (VI').

The solvent to be used in the reaction may be any one inert to the reaction and examples of such a solvent include ether, tetrahydrofuran, 1,4-dioxane, benzene, toluene, xylene, dichloromethane, chloroform, 1,2-dichloroethane, acetonitrile, N,N-dimethylform-amide and pyridine.

The reaction temperature preferably ranges from –20° C. to the refluxing temperature of the solvent.

Further, the coexistence of a base in the reaction gives desirable results and examples of the base include organic ones such as triethylamine, diisopropylethylamine and lutidine; and inorganic ones such as sodium hydrogencarbonate, sodium carbonate, potassium carbonate and sodium hydroxide.

Preparation process 11

A compound represented by the general formula (IV) which is the starting material of Preparation process 5 can be prepared by the following process:

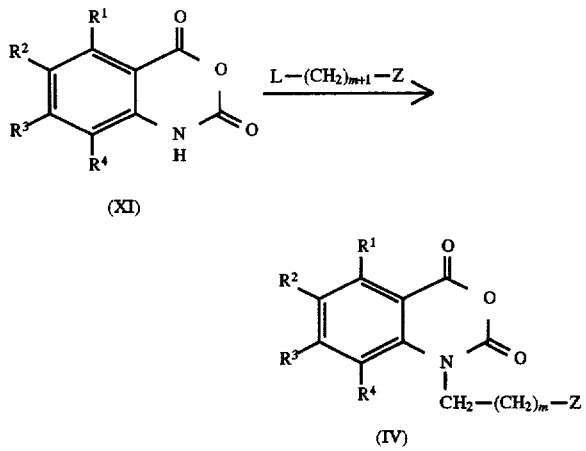

(wherein $R^1$ to $R^4$, m, X, Hal and Z are each as defined above).

Accordingly, this is a process that an objective compound (IV) can be prepared by reacting a compound represented by the general formula (XI) with sodium hydroxide, potassium hydride or the like, and reacting the resulting product with a compound represented by the general formula (VI).

In carrying out the reaction, a solvent inert to the reaction may be used, and examples of the solvent include N,N-dimethylformamide, N,N-dimethylacetamide and tetrahydrofuran.

The reaction temperature preferably ranges from about 0° C. to the refluxing temperature of the solvent.

Preparation process 12

A compound represented by the general formula (If) which is the starting material of Preparation process 6 can be prepared by the following process:

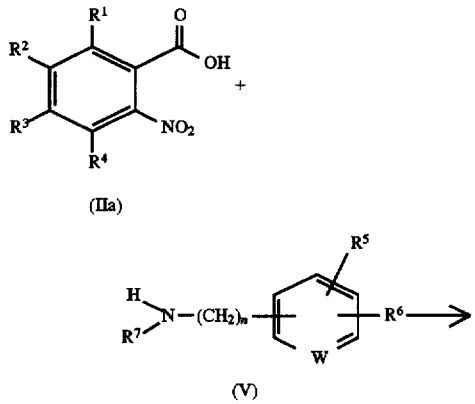

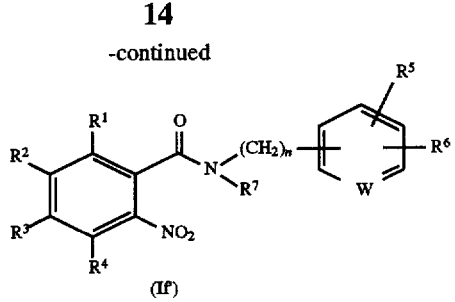

(wherein $R^1$ to $R^7$ and n are each as defined above).

Accordingly, this is a process that a compound represented by the general formula (If) can be prepared by reacting a carboxylic acid represented by the general formula (IIa) or a reactive derivative thereof with a compound represented by the general formula (V) through amidation. The reactive derivative of the compound (IIa) includes acid halides such as acid chloride and acid bromide; acid azides; active esters thereof with N-hydroxybenztriazole and N-hydroxysuccinimide; and mixed acid anhydrides thereof with p-toluenesulfonic acid and phosphoric acid ester.

When as a compound (IIa) free carboxylic acid is used, the reaction may be conducted in the presence of a condensing agent such as N,N'-dicyclohexylcarbodiimide, N-ethyl-N'-(3-dimethylaminopropyl)carbodiimide or 2-ethoxy-1-ethoxycarbonyl-1,2-dihydroquinoline.

In carrying out the reaction, an organic solvent inert to the reaction may be used, and examples of the solvent include ether, tetrahydrofuran, 1,4-dioxane, benzene, toluene, xylene, dichloromethane, chloroform, 1,2-dichloroethane, acetonitrile and N,N-dimethylformamide.

The reaction temperature preferably ranges from about 0° C. to the refluxing temperature of the solvent.

When a certain reactive derivative is used, the addition of a base to the reaction system gives desirable results, and examples of the base include triethylamine, diisopropylethylamine, pyridine, lutidine, sodium hydrogencarbonate, sodium carbonate and potassium carbonate.

Preparation process 13

A compound represented by the general formula (IIa) which is the starting material of Preparation process 12 can be prepared by the following process:

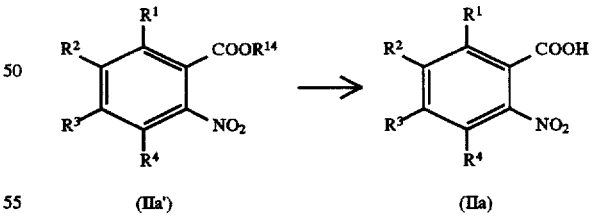

(wherein $R^1$ to $R^4$ and $R^{14}$ are each as defined above).

Accordingly, a compound represented by the general formula (IIa) can be prepared by deblocking a compound represented by the general formula (IIa').

The above reaction is preferably conducted in a solvent inert to the reaction (such as methanol, ethanol, tetrahydrofuran or 1,4-dioxane) in the presence of a base such as lithium hydroxide, sodium hydroxide, potassium hydroxide or barium hydroxide at a temperature ranging from about 0° C. to the refluxing temperature of the solvent.

Preparation process 14

A compound represented by the general formula (III') which is the starting material of Preparation process 8 can be prepared by the following process:

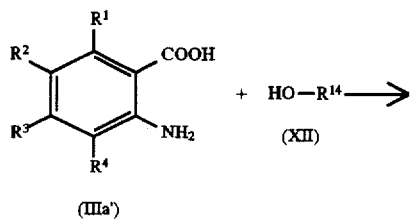

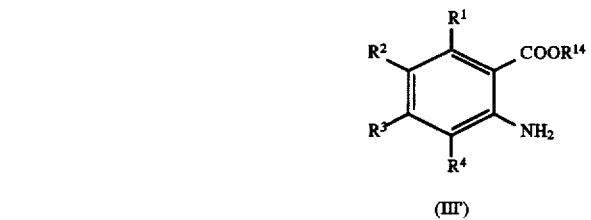

(wherein $R^1$ to $R^4$ and $R^{14}$ are each as defined above).

Accordingly, a compound represented by the general formula (III') can be prepared by condensing a compound represented by the general formula (IIIa') with a compound represented by the general formula (XII).

Although the condensation can be conducted by a conventional process the use of a condensing agent is preferable. Examples of the condensing agent include N,N'-dicyclohexylcarbodiimide, N-ethyl-N'-(3-dimethylaminopropyl)carbodiimide and 2-ethoxy-1-ethoxycarbonyl-1,2-dihydroquinoline, though any conventional condensing agent can be used.

The reaction can be accelerated by the coexistence of 4-dimethylaminopyridine or 4-pyrrolidinopyridine.

The reaction is preferably conducted in a solvent inert to the reaction such as acetonitrile, dichloromethane, chloroform or N,N-dimethylformamide at a temperature ranging from about 0° C. to the refluxing temperature of the solvent.

Preparation process 15

A compound represented by the general formula (III) wherein X is represented by the formula: —CO—; m is 0; $R^2$ is a cyano group; and $R^8$ is a hydrogen atom, which is the starting material of Preparation process 7, can be prepared by the following process:

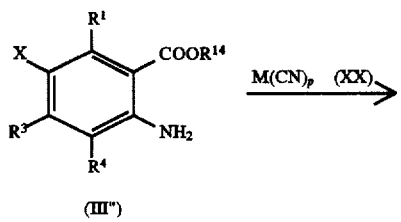

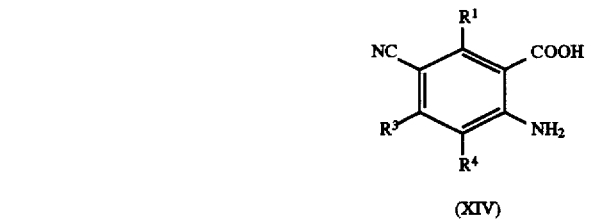

(wherein $R^1$, $R^3$, $R^4$ and $R^{14}$ are each as defined above; M represents a metal atom; and p is an integer of 1 to 3).

Accordingly, a compound represented by the general formula (XIV) can be prepared by reacting a compound represented by the general formula (III") with a transition metal cyanide represented by the general formula (XX).

The transition metal cyanide is preferably cuprous cyanide.

The reaction is preferably conducted either in the absence of any solvent or in the presence of an organic solvent inert to the reaction such as pyridine, quinoline, N,N-dimethylformamide, N-methyl-2-pyrrolidone or HMPA at a temperature ranging from about 0° C. to the refluxing temperature of the solvent.

Preparation process 16

A compound represented by the general formula (V) in Preparation process 1 wherein $R^7$ is a hydrogen atom, can be prepared by the following process:

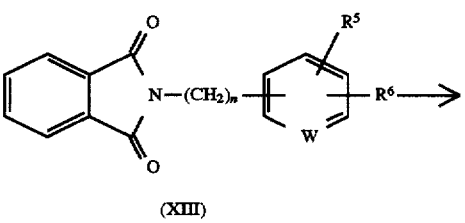

(wherein $R^5$, $R^6$ and n are each as defined above).

Accordingly, a compound represented by the general formula (V') can be prepared by deblocking a compound represented by the general formula (XIII). Although the deblocking may be conducted through acidic or alkaline hydrolysis, it is preferable to conduct the deblocking by the use of hydrazine.

The solvent to be used in the above reaction may be any solvent inert to the reaction, and examples of the solvent include methanol, ethanol, tetrahydrofuran and 1,4-dioxane.

The reaction temperature preferably ranges from about 0° C. to the refluxing temperature of the solvent.

Preparation process 17

A compound represented by the general formula (XIII) which is useful as the starting material of Preparation process 16 can be prepared by the following process:

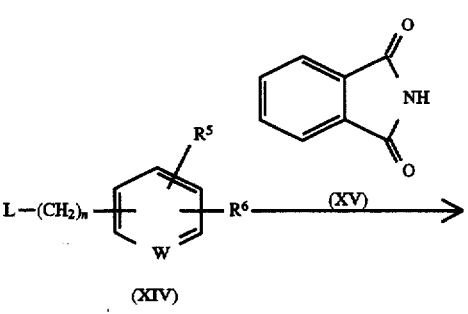

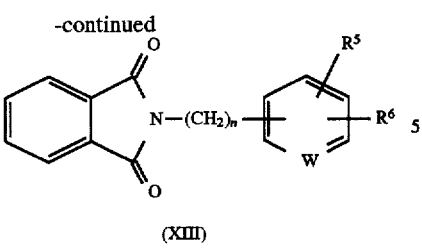

(XIII)

(wherein $R^5$, $R^6$, n and L are each as defined above).

Accordingly, a compound represented by the general formula (XIII) can be prepared by reacting a compound represented by the general formula (XIV) with phthalimide represented by the formula (XV).

When L is a hydroxy group, a compound represented by the general formula (XIII) can be prepared by condensing a compound represented by the general formula (XV) with phthalimide through the Mitsunobu reaction. Although this reaction can be conducted by a conventional process, it may be conducted by the use of a phosphine compound such as triphenylphosphine and tributylphosphine and diethyl azocarboxylate or an azocarboxylic acid diester such as diethyl azocarboxylate.

The above reaction is preferably conducted in a solvent inert to the reaction such as tetrahydrofuran, 1,4-dioxane or acetonitrile at a temperature ranging from about 0° C. to the refluxing temperature of the solvent.

When L is a leaving group such as a halogen atom, methanesulfonyloxy or p-toluenesulfonyloxy, a compound represented by the general formula (XIII) can be prepared by reacting a compound represented by the general formula (XIV) with phthalimide or an alkali metal salt thereof. The alkali metal salt of phthalimide includes sodium and potassium salts thereof.

The solvent to be used in the reaction may be one inert to the reaction, and examples of such a solvent include acetonitrile, N,N-dimethylformamide, methanol, ethanol, tetrahydrofuran and 1,4-dioxane.

When phthalimide is used, the reaction can be accelerated by the use of an inorganic base such as sodium carbonate, sodium hydrogencarbonate or potassium carbonate, or an organic base such as triethylamine, tributylamine or diazacycloundecene.

The reaction temperature preferably ranges from about 0° C. to the refluxing temperature of the solvent.

Preparation process 18

A compound represented by the general formula (I) wherein Y is an oxygen atom and $R^1$ and $R^7$ are combined together to form a ring can be prepared by the following process:

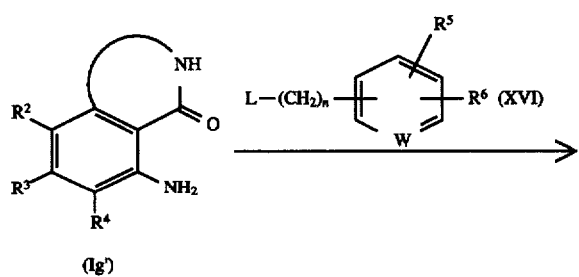

(Ig')

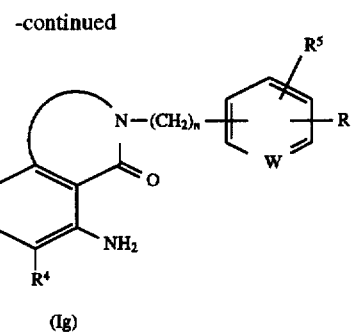

(Ig)

(wherein $R^2$ to $R^6$, n and L are each as defined above).

Accordingly, a compound represented by the general formula (Ig), can be prepared by reacting a compound represented by the general formula (Ig') with a compound represented by the general formula (XVI).

It is preferable that the reaction be conducted in the presence of a base such as sodium hydride, potassium hydride or potassium t-butoxide.

The reaction is preferably conducted in a solvent inert to the reaction such as tetrahydrofuran, 1,4-dioxane, N,N-dimethylformamide, dimethyl sulfoxide or N-methyl-2-pyrrolidone at a temperature ranging from about 0° C. to the refluxing temperature of the solvent.

Preparation process 19

A compound represented by the general formula (Ig') which is the starting material of Preparation process 18 can be prepared by the following process:

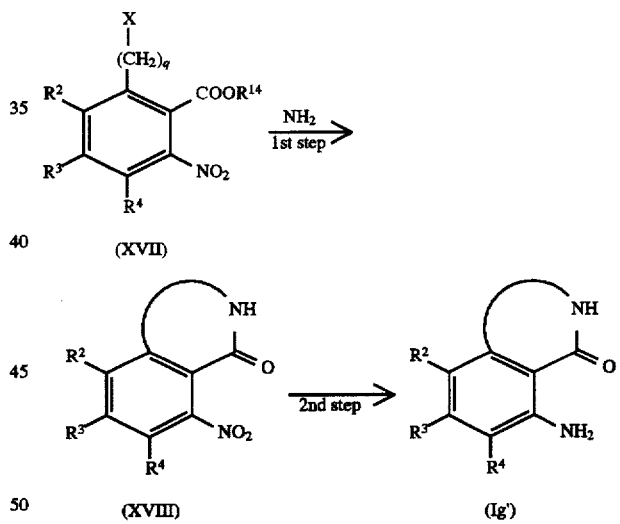

(wherein $R^2$ to $R^4$, $R^{14}$ and L are each as defined above; and q is an integer of 1 to 6).

(1st step)

Accordingly, a compound represented by the general formula (XVIII) is prepared by reacting a compound represented by the general formula (XVII) with ammonia.

In carrying out the reaction, a solvent inert to the reaction may be used, and examples of the solvent include methanol, ethanol, tetrahydrofuran and 1,4-dioxane.

The reaction temperature preferably ranges from about 0° C. to the refluxing temperature of the solvent.

(2nd step)

Accordingly, a compound represented by the general formula (Ig') is prepared by reducing a compound represented by the general formula (XVIII) in a conventional manner.

The reduction can be conducted by a conventional process, and examples of the process include catalytic reduction with palladium/carbon or platinum oxide; reduction using a metal such as iron, tin or zinc and an acid such as hydrochloric acid or acetic acid; and reduction using stannic chloride.

The solvent to be used in the reduction may be one inert to the reduction, for example, methanol or ethanol.

The reaction temperature preferably ranges from about 0° C. to the refluxing temperature of the solvent.

Preparation process 20

A compound represented by the general formula (Ig') which is the starting material of Preparation process 18 can be prepared also by the following process:

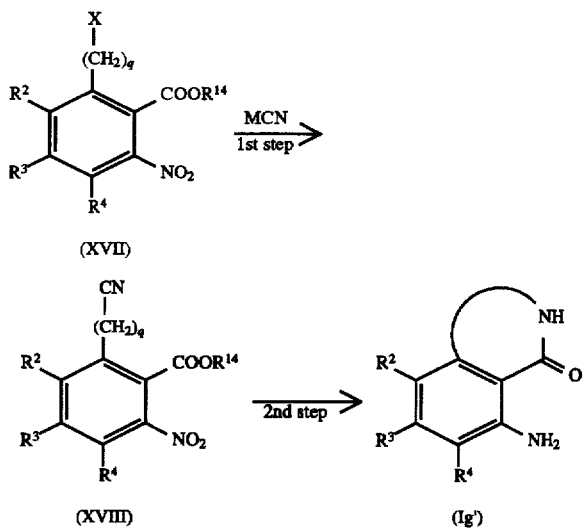

(wherein $R^2$ to $R^4$, $R^{14}$, L and q are each as defined above).
(1st step)

Accordingly, a compound represented by the general formula (XVIII) is prepared by reacting a compound represented by the general formula (XVII) with a metal cyanide.

In carrying out the above reaction, a solvent inert to the reaction may be used, and examples thereof include water, methanol, ethanol, tetrahydrofuran, 1,4-dioxane, acetonitrile, N,N-dimethylformamide and dimethyl sulfoxide.

The reaction temperature preferably ranges from about 0° C. to the refluxing temperature of the solvent.
(2nd step)

Accordingly, a compound represented by the general formula (Ig') is prepared by reducing a compound represented by the general formula (XVIII) in a conventional manner.

This reduction can be conducted by a conventional process, and examples thereof include catalytic reduction with palladium/carbon or platinum oxide; reduction using a metal such as iron, tin or zinc and an acid such as hydrochloric or acetic acid; and reduction using stannic chloride.

The solvent to be used in the reduction may be one inert to the reduction, for example, methanol or ethanol.

The reaction temperature preferably ranges from about 0° C. to the refluxing temperature of the solvent.

Preparation process 21

A compound represented by the general formula (Ig') wherein $R^2$ is a halogen atom, which is the starting material of Preparation process 18, can be prepared by the following process:

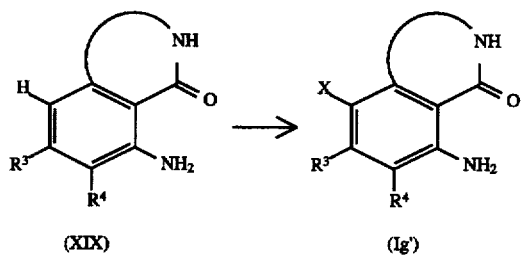

(wherein $R^3$, $R^4$ and X are each as defined above).

Accordingly, a compound represented by the general formula (Ig') can be prepared by halogenating a compound represented by the general formula (XIX) in a conventional manner.

This halogenation can be conducted by a conventional process, and examples of the process include those using chlorine, bromine, tetra-n-butylammonium tribromide and benzyltrimethylammonium tribromide, respectively. The solvent to be used in the halogenation may be one inert to the halogenation, for example, dichloromethane, chloroform or acetic acid.

The reaction temperature preferably ranges from about 0° C. to the refluxing temperature of the solvent.

The present invention also provides the following compounds:

those represented by the general formula (II) and pharmacologically acceptable salts thereof:

general formula (II)

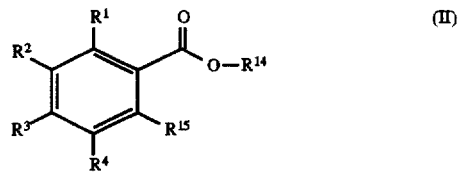

(wherein $R^1$, $R^2$, $R^3$ and $R^4$ are each as defined above; $R^{14}$ represents a hydrogen atom, an optionally halogenated lower alkyl group or an optionally substituted arylalkyl group; and $R^{15}$ represents a nitro group or an amino group);

those represented by the general formula (III) and pharmacologically acceptable salts thereof:

general formula (III)

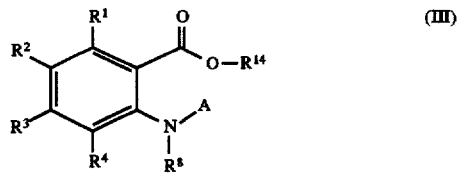

(wherein $R^1$, $R^2$, $R^3$, $R^4$, $R^8$, $R^{14}$ and A are each as defined above);

and those represented by the general formula (IV) and pharmacologically acceptable salts thereof:

general formula (IV)

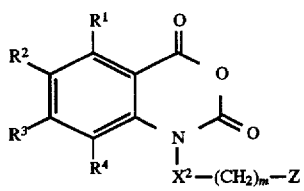

(wherein $R^1$, $R^2$, $R^3$, $R^4$, m and Z are each as defined above; and $X^2$ represents a group of the formula: —$CH_2$—).

These compounds (II), (III) and (IV) are useful as intermediates for preparing the compounds (I).

Pharmacological Experimental Example will now be described to illustrate the usefulness of the compounds of the present invention.

Pharmacological Experimental Example

Enzyme Inhibitory activity using cGMP-PDE prepared from porcine aorta

1. Experimental method

The enzyme activity of CGMP-PDE prepared from porcine aorta was determined according to the method of Thompson et al. This determination was conducted in the presence of 1 mM EGTA by the use of 1 μM cGMP as the substrate. Each compound according to the present invention was dissolved in DMSO and added to the reaction system to determine the inhibitory activity thereof. The final concentration of DMSO in the reaction system was adjusted to 4% or below.

The cGMP-PDE was prepared as follows:

Porcine aorta was cut into fine pieces, followed by the addition of 10 times by volume as much buffer A (20 mM Tris/HCl, 2 mM Mg acetate, 1 mM dithiothreitol, 5 mM EDTA, 1400TIU/1 aprotinin, 10 mg/1 leupeptin, 1 mM benzamidine, 0.2 mM PMSF, pH7.5). The obtained mixture was homogenized and centrifuged at 100,000×g for one hour. The obtained supernatant was placed on a column of DEAE-Toyopearl 650S (a product of Tosoh, Tokyo, Japan), followed by the washing of the column with buffer B (50 mM Tris/HCl, 0.1 mM EGTA, 2 mM Mg acetate, 1 mM Dithiothreitol, 0.2 mM PMSF, pH7.5). The resulting column was subjected to gradient elution with 0.05 to 0.4M sodium chloride to obtain CaM-independent cGMP-PDE fractions.

2. Experimental results

The cGMP-PDE inhibitory activities of compounds of the present invention thus determined are given in Table 1, wherein a lower $IC_{50}$ value exhibits a more remarkable effect.

TABLE 1

| Ex. No. | $IC_{50}$ (nM) |
|---|---|
| 9 | 28.8 |
| 19 | 16.6 |
| 33 | 20.5 |
| 38 | 6.7 |
| 39 | 3.2 |
| 41 | 1.4 |
| 43 | 0.9 |
| 44 | 79.8 |
| 45 | 0.7 |
| 47 | 5.3 |
| 74 | 2.4 |
| 80 | 11.9 |
| 81 | 14.5 |
| 83 | 12.6 |
| 85 | 21.7 |
| 109 | 4.4 |

TABLE 1-continued

| Ex. No. | $IC_{50}$ (nM) |
|---|---|
| 110 | 0.7 |
| 111 | 2.0 |
| 112 | 5.3 |
| 113 | 0.4 |
| 114 | 1.7 |
| 115 | 24.8 |
| 116 | 2.9 |
| 117 | 11.5 |
| 120 | 21.5 |
| 121 | 7.7 |
| 122 | 5.0 |
| 123 | 6.1 |
| 125 | 19.2 |
| 126 | 2.9 |
| 129 | 36.8 |
| 136 | 18.1 |
| 141 | 7.2 |

It can be understood from the results of the above Pharmacological Experimental Example that the compound of the present invention has an inhibitory activity against PDE, particularly cGMP-PDE. In other words, it can be understood that the compound of the present invention exhibits an effect of increasing the in vivo concentration of cGMP through its inhibitory activity against cGMP-PDE. Accordingly, the anthranilic acid derivative of the present invention is effective in the prevention and treatment of diseases wherein a cGMP-PDE inhibitory action is efficacious. Examples of such diseases include ischemic heart diseases such as angina pectoris, myocardial infarction, and chronic and acute heart failure; pulmonary hypertension accompanied and not accompanied by cot pulmonale; hypertension due to various causes; peripheral circulation failure; brain circulatory failure; cerebral dysfunction; and allergic diseases such as bronchial asthma, atopic dermatitis and allergic rhinitis.

Further, the compound of the present invention is less toxic and highly safe, thus being valuable also in this sense.

The present invention provides a preventive and therapeutic agent for diseases wherein a phosphodiesterase inhibitory action is efficacious, which comprises an anthranilic acid derivative or pharmacologically acceptable salt thereof as described above as an active ingredient; and a preventive and therapeutic agent for diseases wherein a cyclic GMP phosphodiesterase inhibitory action is efficacious, which comprises an anthranilic acid derivative or pharmacologically acceptable salt thereof as described above as an active ingredient.

The compound of the present invention is particularly efficacious against ischemic heart diseases, angina pectoris, hypertension, pulmonary hypertension, heart failure and asthma.

Further, the present invention provides a drug composition comprising a pharmacologically effective amount of an anthranilic acid derivative or pharmacologically acceptable salt thereof as described above and a pharmacologically acceptable carrier; and a method for the prevention and treatment of diseases which comprises administering a pharmacologically acceptable amount of an anthranilic acid derivative or pharmacologically acceptable salt thereof as described above to inhibit phosphodiesterase.

The compound of the present invention is administered as a drug orally or parenterally. The dose thereof varies depending upon the extent of sympton; the age, sex, weight and drug sensitivity of patient; dosage-regimen; dosing timing; dosing interval; the kind of preparation; the drug to be administered together therewith; the kind of the active ingredient and so on, being not particularly limited.

In the oral administration, the dose per adult a day is generally about 0.1 to 1000 mg, preferably about 5 to 500 mg, which may be administered in one to three portions a day.

In the administration as an injection, the dose a day is generally about 1 µg/kg to 3000 µg/kg, preferably about 3 µg/kg to 1000 µg/kg.

A solid preparation for oral administration according to the present invention is prepared by adding a filler and, if necessary, a binder, disintegrator, lubricant, color and/or corrigent to an active ingredient and shaping the obtained mixture into a tablet, coated tablet, granule, powder or capsule.

Examples of the filler include lactose, corn starch, sucrose, glucose, sorbitol, crystalline cellulose and silicon dioxide; those of the binder include polyvinyl alcohol, polyvinyl ether, ethylcellulose, methylcellulose, acacia, tragacanth, gelatin, shellac, hydroxypropylcellulose, hydroxypropylmethylcellulose, calcium citrate, dextrin and pectin; those of the lubricant include magnesium stearate, talc, polyethylene glycol, silica and hardened vegetable oil; those of the color include those authorized as pharmaceutical additives; and those of corrigent include cocoa powder, menthol, aromatic powder, mentha oil, borneol and powdered cinnamon bark. Of course, the tablet and granule may be suitably coated with sugar, gelatin or the like, if necessary.

When an injection according to the present invention is prepared, a pH regulator, buffer, suspending agent, solubilizing agent, stabilizer, isotonicity and/or preservative may be added to an active ingredient at need and formulating the mixture into an injection for intravenous, subcutaneous or intramuscular administration in a conventional manner. Further, the injection may be freeze-dried at need.

Examples of the suspending agent include methylcellulose, Polysorbate 80, hydroxyethylcellulose, acacia, tragacanth powder, carboxymethylcellulose sodium, and polyoxyethylene sorbitan monolaurate.

Examples of the solubilizing agent include polyoxyethylene hardened castor oil, Polysorbate 80, nicotinamide, polyoxyethylene sorbitan monolaurate, Macrogol, and ethyl ester of castor oil fatty acid.

Examples will now be described to facilitate the understanding of the present invention, though they are preceded by Preparative Examples as synthesis examples wherein starting material compounds to be used in the preparation of the compounds of the present invention are prepared.

Preparative Example 1
Ethyl 1-[(2-Carboxy-4-chlorophenyl-1)carbamoyl]-piperidine-4-carboxylate

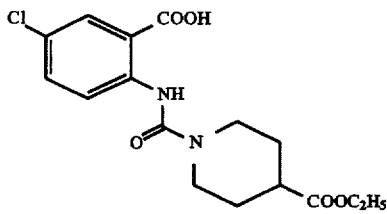

Anisole (4.7 ml) was added to 4.09 g of ethyl 1-[[4-chloro-2-[(4-methoxybenzyloxy)carbonyl]phenyl]-carbamoyl]piperidine-4-carboxylate, followed by the dropwise addition of 6.6 ml of trifluoroacetic acid. The obtained mixture was stirred at room temperature for one hour and concentrated, followed by the addition of ether. The resulting mixture was extracted with a saturated aqueous solution of sodium hydrogencarbonate. The pH of the aqueous phase was adjusted to about 2 with concentrated hydrochloric acid to precipitate crystals. The crystals were recovered by filtration and washed with water to give 2.09 g of the title compound as a white powder (yield: 69%).

M.P.: 159° to 160° C. (dec.) (white needle aq. EtOH)
NMR(400 MHz, δ, CDCl₃)
1.27(t, J=7.1Hz, 3H), 1.78(m, 2H), 2.02(m, 2H), 2.58(m, 1H), 3.10(m, 2H), 4.11(m, 2H), 4.18(q, J=7.1Hz, 2H), 7.47(dd, J=2.7, 9.2Hz, 1H), 8.01(d, J=2.7Hz, 1H), 8.47(d, J=9.2Hz, 1H), 10.70(s, 1H)

Preparative Example 2
Ethyl 1-[[4-chloro-2-(4-methoxybenzyloxy)-carbonylphenyl]carbamoyl]piperidine-4-carboxylate

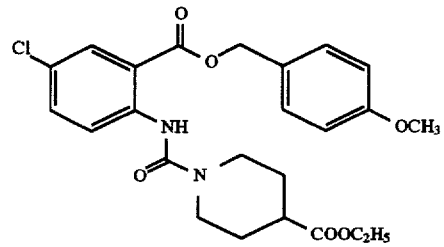

4-Methoxybenzyl 2-amino-5-chlorobenzoate (20.74 g) was dissolved in 180 ml of tetrahydrofuran, followed by the addition of 12.69 g of 1,1'-carbonyldiimidazole. The obtained mixture was heated under reflux for 43 hours and cooled by allowing to stand, followed by the addition of 12.06 ml of ethyl isonipecotate. The obtained mixture was allowed to stand at room temperature for one hour, followed by concentration. Water was added to the obtained concentrate, followed by the extraction with ethyl acetate. The organic phase was washed with 1N hydrochloric acid, a saturated aqueous solution of sodium hydrogencarbonate, and a saturated aqueous solution of common salt successively, dried over anhydrous magnesium sulfate, and distilled to remove the solvent. Benzene-insoluble matters were filtered out and the filtrate was purified by silica gel column chromatography (solvent: n-hexane/ethyl acetate (3:1)) to give 11.07 g of the title compound as a yellow oil (yield: 334).

NMR(400MHz, δ, CDCl₃)
1.27(t, J=7.1Hz, 3H), 1.76(m, 2H), 2.01(m, 2H), 2.54(m, 1H), 3.07(m, 2H), 3.83(s, 3H), 4.12(m, 2H), 4.32(q, 7.1Hz, 2H), 5.28(s, 2H), 6.91–6.96(m, 2H), 7.36–7.40 (m, 2H), 7.43(dd, J=2.6, 9.2Hz, 1H), 7.95(d, J=2.6Hz), 8.66(d, J=9.2Hz), 10.68(s, 1H)

Preparative Example 3
4-Methoxybenzyl 2-amino-5-chlorobenzoate

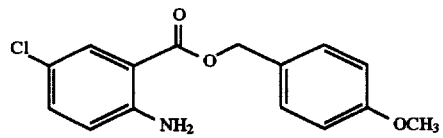

2-Amino-5-chlorobenzoic acid (15.00 g), methoxybenzyl chloride (13.1 ml) and potassium carbonate (13.3 g) were added to N,N-dimethylformamide (175 ml). The obtained mixture was stirred at room temperature for 43 hours, followed by the addition of ice-water. The resulting mixture was extracted with ethyl acetate. The organic phase was washed with water and a saturated aqueous solution of common salt, dried over anhydrous magnesium sulfate, and distilled to remove the solvent. The residue was purified by silica gel column chromatography (solvent: n-hexane/ethyl acetate (5:1)) to give 20.97 g of the title compound as a pale-yellow oil (yield: 82%).

NMR(400MHz, δ, CDCl₃)

3.82(s, 3H), 5.24(s, 2H), 5.74(br, 2H), 6.59(d, J=8.8Hz, 1H), 6.89–6.94(m, 2H), 7.18(dd, J=2.6, 8.8Hz, 1H), 7.34–7.39(m, 2H), 7.82(d, J=2.6Hz, 1H)

Preparative Example 4

Methyl 2-amino-5-dimethylaminomethylbenzoate

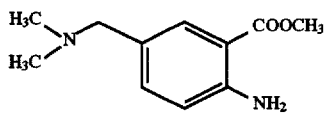

Methyl 5-dimethylaminomethyl-2-nitrobenzoate (12.92 g) and stannous chloride dihydrate (60.39 g) were added to 110 ml of ethanol. The obtained mixture was stirred at 70° C. for one hour, followed by the addition of ice-water. The resulting mixture was alkalified with sodium carbonate and extracted with ethyl acetate. The organic phase was dried over anhydrous magnesium sulfate and distilled to remove the solvent. The residue was purified by silica gel chromatography (solvent: dichloromethane/methanol (30:1 to 10:1)) to give 10.93 g of the title compound as a pale-yellow oil (yield: 97%).

NMR(400MHz, δ, CDCl₃)

2.20(s, 6H), 3.29(s, 2H), 3.85(s, 3H), 5.68(br, 2H), 6.63(d, J=8.4Hz, 1H), 7.22(dd, J=2.2, 8.4Hz, 1H), 7.74(d, J=2.2Hz, 1H)

Preparative Example 5

Methyl 5-dimethylaminomethyl-2-nitrobenzoate

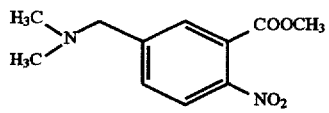

Methyl 5-methyl-2-nitrobenzoate (8.06 g) was dissolved in 140 ml of carbon tetrachloride, followed by the addition of 7.72 g of N-bromosuccinimide and 0.50 g of benzoyl peroxide. The obtained mixture was heated under reflux for 5 hours and filtered to remove insolubles. The filtrate was concentrated to give a yellow oil. This oil was dissolved in 80 ml of acetonitrile, followed by the addition of 4.04 g of dimethylamine hydrochloride and 6.86 g of potassium carbonate. The obtained mixture was stirred at room temperature for 5 hours and concentrated, followed by the addition of water. The resulting mixture was extracted with ethyl acetate. The organic phase was dried over anhydrous magnesium sulfate and distilled to remove the solvent. The residue was purified by silica gel column chromatography (solvent: dichloro-methane/methanol (30:1)) to give 3.17 g of the title compound as a yellow oil (yield: 32%).

NMR(400MHz, δ, CDCl₃)

2.26(s, 6H), 3.51(s, 2H), 3.93(s, 3H), 7.59(dd, J=1.8, 8.4Hz, 1H), 7.68(d, J=1.8Hz, 1H), 7.91(d, J=8.4Hz, 1H)

Preparative Example 6

6-Chloro-1-[4-(ethoxycarbonyl)butyl]-1,2-dihydro-4H-1,3-benzoxazine-2,4-dione

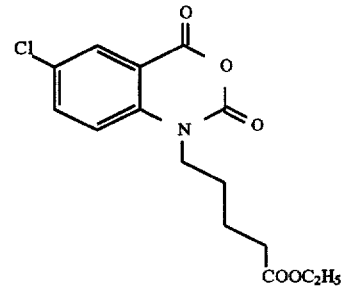

1.11 g of 60% sodium hydride (suspended in mineral oil) was suspended in 80 ml of N,N-dimethylacetamide, followed by the addition of 5.00 g of 6-chloro-1,2-dihydro-4H-3,1-benzoxazine-2,4-dione in portions. The obtained mixture was stirred at room temperature for one hour, followed by the addition of 4.81 ml of ethyl 5-bromovalerate. The obtained mixture was stirred at 50° C. for 24 hours and poured onto 200 ml of 1N hydrochloric acid/ice, followed by the extraction with ethyl acetate. The organic phase was washed with water and a saturated aqueous solution of common salt, dried over anhydrous magnesium sulfate, and distilled to remove the solvent. Ether was added to the obtained solid residue and the resulting mixture was filtered to give 4.89 g of the title compound as a pale-yellow powder (yield: 60%).

M.P.: 97° to 99° C.

(slightly yellow needle from n-Hex/EtOAc)

NMR(400MHz, δ, CDCl₃)

1.25(t, J=7.1Hz, 3H), 1.72–1.86(m, 4H), 2.40(t, J=7.0Hz, 2H), 4.07(t, J=7.3Hz, 2H), 4.13(q, J=7.1Hz, 2H), 7.17 (d, J=9.0Hz, 1H), 7.71(dd, J=2.6, 9.0Hz, 1H), 8.12(d, J=2.6Hz, 1H)

Preparative Example 7

6-Chloro-1-[3-(ethoxycarbonyl)propyl]-1,2-dihydro-4H-1,3-benzoxazine-2,4-dione

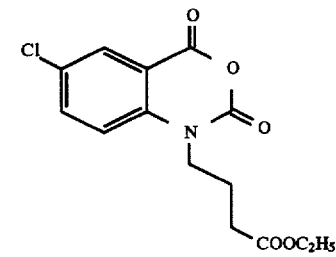

A pale-yellow powder was prepared (yield: 60%).

M.P.: 78° to 80° C.

(pale-yellow prism from n-Hex/EtOAc)

NMR(400MHz, δ, CDCl₃)

1.30(t, J=7.1Hz, 3H), 1.99–2.09(m, 2H), 2.51(t, J=6.2Hz, 2H), 4.12(t, J=8.1Hz, 2H), 4.19(q, J=7.1Hz, 2H), 7.52 (d, J=9.0Hz, 1H), 7.75(dd, J=2.4, 9.0Hz, 1H), 8.12(d, J=2.4Hz, 1H)

Preparative Example 8
6-Chloro-1-[4-(methoxycarbonyl)benzyl]-1,2-dihydro-4H-1,3-benzoxazine-2,4-dione

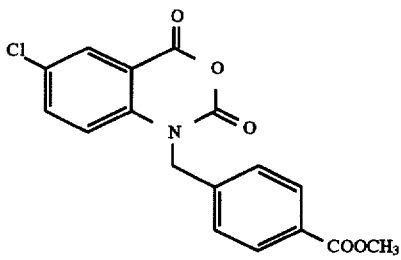

A slightly yellow powder was prepared (yield: 89%).
M.P.: 214° to 217° C. (white needle from EtOAc)
NMR(400NHz, δ, CDCl₃)

3.91(s, 3H), 6.97(d, J=9.0Hz, 1H), 7.33–7.38(m, 2H), 7.57(dd, J=2.6, 9.0Hz, 1H), 8.02–8.06(m, 2H), 8.14(d, J=2.6Hz)

Preparative Example 9
4-Methoxybenzyl 2-amino-5-bromobenzoate

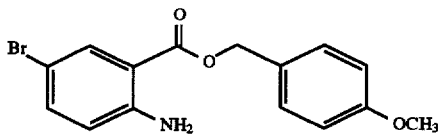

2-Amino-5-bromobenzoic acid (15.59 g), 4-methoxybenzyl alcohol (7.5 ml), 1,3-dicyclohexylcarbodiimide (14.89 g) and 4-dimethylaminopyridine (8.07 g) were added to 200 ml of acetonitrile. The obtained mixture was stirred at room temperature for 18 hours and filtered to remove insolubles. The filtrate was concentrated in a vacuum, followed by the addition of water. The resulting mixture was extracted with ethyl acetate. The ethyl acetate phase was washed with water, 1N hydrochloric acid, water, 1N sodium hydroxide, water, and a saturated aqueous solution of common salt successively, dried over anhydrous magnesium sulfate, and distilled in a vacuum to remove the solvent. The residue was purified by silica gel column chromatography (solvent: n-hexane/ethyl acetate (8:1 to 5:1)) to give 13.13 g of the title compound as a pale-yellow oil (yield: 65%).

¹H-NMR(400MHz, CDCl₃) δ:
3.82(3H, s), 5.24(2H, s), 5.76(2H, br s), 6.54(1H, d, J=8.8Hz), 6.92(2H, m), 7.30(1H, dd, J=8.8, 2.6Hz), 7.37(2H, m), 7.96(1H, d, J=2.6Hz)

Preparative Example 10
4-Methoxybenzyl 2-amino-5-cyanobenzoate

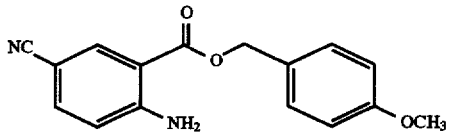

2-Amino-5-cyanobenzoic acid (32.18 g), 4-methoxybenzyl chloride (28.34 ml) and anhydrous potassium carbonate (28.89 g) were added to 400 ml of N,N-dimethylformamide. The obtained mixture was stirred at room temperature for 15 hours, followed by the addition of ice-water. The resulting mixture was extracted with ethyl acetate. The ethyl acetate phase was washed with water, 1N hydrochloric acid, water, a saturated aqueous solution of sodium hydrogencarbonate, water, and a saturated aqueous solution of common salt successively, dried over anhydrous magnesium sulfate, and distilled in a vacuum to remove the solvent. The residue was purified by silica gel column chromatography (solvent: n-hexane/ethyl acetate (4:1 to 3:1)). The obtained solid was washed with a n-hexane/ethyl acetate mixture to give 28.92 g of the title compound as a pale-yellow powder (yield: 52%).

M.P.: 120°–122° C.
MASS: 283(MH⁺)
¹H-NMR(400MHz, CDCl₃) δ:
3.83(3H, s), 5.26(2H, s), 6.30(2H, br s), 6.65(1H, d, J=8.6Hz), 6.91–6.98(2H, m), 7.35–7.40(2H, m), 7.43 (1H, dd, J=8.6, 2.0Hz), 8.19(1H, d, J=2.0Hz)

Preparative Example 11
Ethyl 1-[[4-bromo-2-[(4-methoxybenzyloxy)carbonyl]phenyl]carbamoyl]piperidine-4-carboxylate

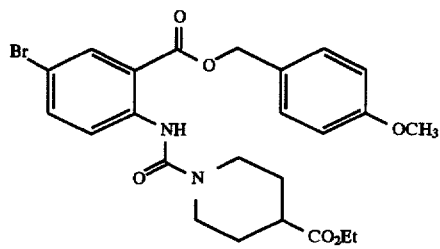

4-Methoxybenzyl 2-amino-5-bromobenzoate (13.13 g) and 1,1'-carbonyldiimidazole (6.97 g) were added to 100 ml of tetrahydrofuran. The obtained mixture was heated under reflux for 41 hours and cooled by allowing to stand, followed by the addition of 6.63 ml of ethyl isonipecotate. The obtained mixture was stirred at room temperature for one hour and concentrated in a vacuum. The residue was purified by silica gel column chromatography (solvent: n-hexane/ethyl acetate (3:1)) to give 4.40 g of the title compound as a pale-yellow solid (yield: 20%).

M.P.: 98° to 100° C.
MASS: 520(MH⁺)
¹H-NMR(400MHz, CDCl₃) δ:
1.27(3H, t, J=7.1Hz), 1.76(2H, m), 2.01(2H, m), 2.55(1H, m), 3.07(2H, m), 3.83(3H, s), 4.12(2H, m), 4.17(2H, q, J=7.1Hz), 5.28(2H, s), 6.94(2H, m), 7.38(2H, m), 7.56 (1H, dd, J=9.2, 2.6Hz), 8.09(1H, d, J=2.6Hz), 8.46(1H, d, J=9.2Hz), 10.69(1H, s)

Preparative Example 12
1-[[4-Chloro-2-[(4-methoxybenzyloxy)carbonyl]phenyl]carbamoyl]-4-hydroxypiperidine

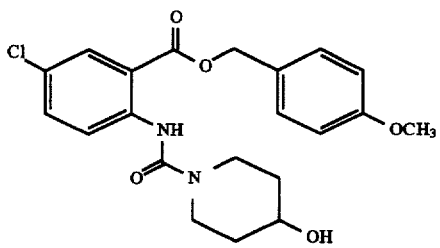

The title compound was prepared as a white solid in a similar manner to that of Preparative Example 3 (yield: 4%).
M.P.: 112° to 114° C.
MASS: 419(MH⁺)
¹H-NMR(400MHz, CDCl₃) δ:

1.55–1.65(3H, m), 1.98(2H, m), 3.27(2H, ddd, J=13.7, 9.2, 3.3Hz), 3.83(3H, s), 3.91–4.00(3H, m), 5.28(2H, s), 6.91–6.96(2H, m), 7.35–7.40(2H, m), 7.43(1H, dd, J=9.2, 2.6Hz), 7.95(1H, d, J=2.6Hz), 8.52(1H, d, J=9.2Hz), 10.69(1H, s)

Preparative Example 13

1-[[4-Cyano--2-[(4-methoxybenzyloxy)carbonyl]-phenyl]carbamoyl]-4-hydroxypiperidine

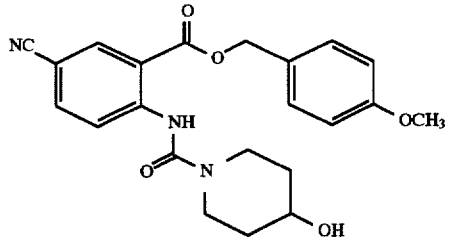

The title compound was prepared as a white solid in a similar manner to that of Preparative Example 3 (yield: 4%).

M.P.: 167° to 169° C.
MASS: 410(MH⁺)
¹H-NMR(400MHz, CDCl₃) δ:

1.56–1.67(3H, m), 1.99(2H, m), 3.33(2H, ddd, J=13.7, 9.0, 3.5Hz), 3.84(3H, s), 3.91–4.03(3H, m), 5.31(2H, s), 6.92–6.97(2H, m), 7.35–7.40(2H, m), 7.69(1H, dd, J=9.0, 2.2Hz), 8.30(1H, d, J=2.2Hz), 8.69(1H, d, J=9.0Hz), 11.04(1H, s)

Preparative Example 14

Ethyl 1-[(4-bromo-2-carboxyphenyl)carbamoyl]piperidine-4-carboxylate

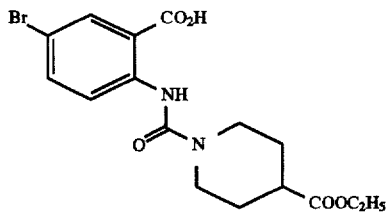

A mixture comprising 3.82 g of ethyl 1-[[4-bromo-2-[(4-methoxybenzyloxy)carbonyl]phenyl]carbamoyl]-piperidine-4-carboxylate, 4.02 ml of anisole and 5.7 ml of trifluoroacetic acid was stirred at room temperature for 2.5 hours and concentrated in a vacuum. An aqueous solution of sodium carbonate and ether were added to the residue to recover the aqueous phase. The ethereal phase was extracted with an aqueous solution of sodium carbonate. Both of the aqueous phases were combined and washed with ether. The resulting aqueous phase was acidified with concentrated hydrochloric acid to give precipitates. The precipitates were recovered by filtration to give 2.50 g of the title compound as a white powder (yield: 85%).

M.P.: 153° to 155° C. (dec.)
MASS: 399(MH⁺)
¹H-NMR(400MHz, CDCl₃) δ:

1.28(3H, t, J=7.1Hz), 1.77(2H, m), 2.02(2H, m), 2.58(1H, m), 3.09(2H, m), 4.11(2H, m), 4.18(2H, q, J=7.1Hz), 7.61(1H, dd, J=9.2, 2.6Hz), 8.16(1H, d, J=2.6Hz), 8.42(1H, d, J=9.2Hz), 10.67(1H, s)

Preparative Example 15

1-[(2Carboxy-4-chlorophenyl)carbamoyl]-4-hydroxypiperidine

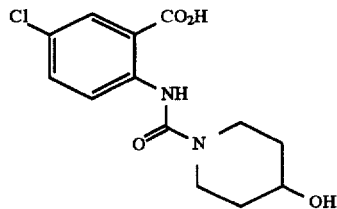

The title compound was obtained as a white solid in a similar manner to that of Preparative Example 6 (yield: 77%).

M.P.: 168° to 170° C. (dec.)
MASS: 299(MH⁺)
¹H-NMR(400MHz, DMSO-d₆) δ:

1.36(2H, m), 1.78(2H, m), 3.16(2H, ddd, J=13.5, 9.5, 3.1Hz), 3.67–3.83(3H, m), 7.57(1H, dd, J=9.2, 2.7Hz), 7.89(1H, d, J=2.7Hz), 8.43(1H, d, J=9.2Hz), 10.85(1H, s)

Preparative Example 16

1-[(2Carboxy-4-cyanophenyl)carbamoyl]-4-hydroxypiperidine

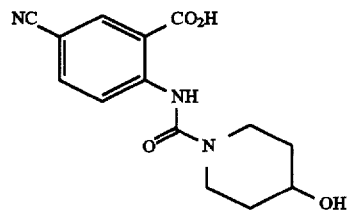

The title compound was obtained as a white solid in a similar manner to that of Preparative Example 6 (yield: 77%).

M.P.: 175° to 179° C. (dec.)
MASS: 290(MH⁺)
¹H-NMR(400MHz, DMSO-d₆) δ:

1.37(2H, m), 1.78(2H, m), 3.19(2H, ddd, J=13.2, 9.3, 3.5Hz), 3.68–3.82(3H, m), 7.93(1H, dd, J=9.0, 2.2Hz), 8.30(1H, d, J=2.2Hz), 8.55(1H, d, J=9.0Hz), 11.23(1H, s)

Preparative Example 17

Methyl 2-amino-5-bromo-4-methoxybenzoate

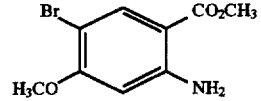

Methyl 2-amino-4-methoxybenzoate (8.44 g) and calcium carbonate (5.13 g) were dissolved in a solvent mixture comprising 250 ml of dichloromethane and 100 ml of methanol, followed by the addition of 19.09 g of benzyltrimethylammonium tribromide in portions. The obtained mixture was stirred at room temperature for one hour and filtered to remove insolubles. The filtrate was concentrated in a vacuum. Ethyl acetate was added to the residue and the obtained mixture was filtered through silica gel. The filtrate was concentrated in a vacuum and the residue was purified by silica gal column chromatography (solvent: n-hexane/ ethyl acetate (4:1)). The obtained solid was washed with n-hexane to give 10.37 g of the title compound as a pale-yellow solid (yield: 86%).

M.P.: 104° to 105° C.
MASS: 260 (MH⁺)
$^1$H-NMR(400MHz, CDCl$_3$) δ:
3.84(3H, s), 3.87(3H, s), 5.85(2H, br, s), 6.12(1H, s), 8.01(1H, s)

Preparative Example 18

7Nitroisoindoline-1-one

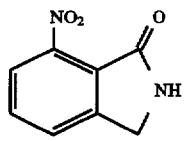

Methyl 2-bromomethyl-5-nitrobenzoate (6.59 g) was suspended in 180 ml of methanol. A large excess of ammonia was passed through the obtained suspension at room temperature. The resulting mixture was stirred at room temperature for 20 hours and concentrated in a vacuum. Water was added to the residue and the obtained mixture was filtered to recover an insoluble matter, which was washed with ether. The title compound (3.88 g) was obtained as a slightly yellow powder (yield: 90%).

M.P.: 218° to 221° C.
MASS: 179(MH⁺)
$^1$H-NMR(400MHz, DMSO-d$_6$) δ:
4.48(2H, s), 7.80(1H, dd, J=7.7, 7.3Hz), 7.87(1H, d, J=7.3Hz), 7.88(1H, d, J=7.7Hz), 8.98(1H, br s)

Preparative Example 19

7Aminoisoindoline-1-one

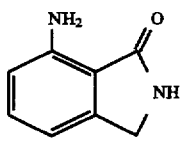

7-Nitroisoindoline (6.52 g) was suspended in 1000 ml of tetrahydrofuran, followed by the addition of 1 g of 10% palladium/carbon (water-containing one). The obtained mixture was subjected to catalytic reduction under the conditions of room temperature and one atm. After 18 hours, the catalyst was filtered out and the filtrate was concentrated in a vacuum. The obtained solid was washed with ether to give 5.13 g of the title compound as a slightly yellow powder (yield: 95%).

M.P.: 153° to 155° C.
MASS: 149(MH⁺)
$^1$H-NMR(400MHz, CDCl$_3$) δ:
4.36(2H, s), 5.21(2H, br s), 6.57(1H, d, J=8.1Hz), 6.70 (1H, d, J=7.3Hz), 6.72(1H, br s), 7.27(1H, dd, J=8.1, 7.3Hz)

Preparative Example 20

Methyl 2-cyanomethyl-6-nitrobenzoate

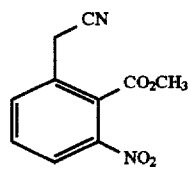

Methyl 2-bromomethyl-5-nitrobenzoate (11.64 g) was suspended in 200 ml of methanol, followed by the addition of a solution of 2.19 g of sodium cyanide in 20 ml of water. The obtained mixture was stirred at 50° C. for 3 hours and concentrated in a vacuum. Water was added to the residue and the resulting mixture was extracted with ethyl acetate. The organic phase was washed with water and a saturated aqueous solution of common salt, dried over anhydrous magnesium sulfate, and concentrated in a vacuum. The residue was purified by silica gel column chromatography (solvent: n-hexane/ethyl acetate (3:1 to 2:1)). The obtained solid was washed with n-hexane to give 5.43 g of the title compound as a white solid (yield: 58%).

M.P.: 103° to 105° C.
MASS: 221(MH⁺)
$^1$H-NMR(400MHz, CDCl$_3$) δ:
3.91(2H, s), 3.98(3H, s), 7.68(1H, t, J=8.1Hz), 7.87(1H, dd, J=8.1, 1.1Hz), 8.11(1H, dd, J=8.1, 1.1Hz)

Preparative Example 21

8-Amino-1,2,3,4-tetrahydro-1-isoquinolinone

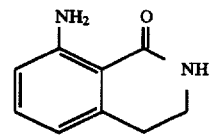

Methyl 2-cyanomethyl-5-nitrobenzoate (54.43 g) was suspended in 200 ml of methanol, followed by the addition of 4.5 ml of concentrated hydrochloric acid and 0.18 g of platinum oxide. The obtained mixture was subjected to catalytic reduction under the conditions of room temperature and 3 kg/cm². After 7 hours the catalyst was filtered out and the filtrate was concentrated in a vacuum.

The residue was dissolved in 50 ml of methanol, followed by the addition of 7.50 g of anhydrous potassium carbonate. The obtained mixture was heated under reflux for 9.5 hours and filtered to remove insolubles. The filtrate was concentrated in a vacuum, followed by the addition of water. The resulting mixture was extracted with ethyl acetate. The organic phase was washed with water and a saturated aqueous solution of common salt, dried over anhydrous magnesium sulfate, and concentrated in a vacuum. The residue was purified by silica gel column chromatography (solvent: dichloromethane/methanol (30:1)) to give 0.75 g of the title compound as a white solid (yield: 19%).

M.P.: 128° to 130° C.
MASS: 163 (MH⁺)
$^1$H-NMR(400MHz, CDCl$_3$) δ:
2.90(2H, t, J=6.6Hz), 3.47(1H, dt, J=6.6, 2.9Hz), 5.98(1H, br s), 6.05(2H, br s), 6.43(1H, dd, J=7.3, 1.1Hz), 6.52(1H, dd, J=8.3, 1.1Hz), 7.12(1H, dd, J=8.1, 7.3Hz)

Preparative Example 22

7Amino-4-bromoisoindoline-1-one

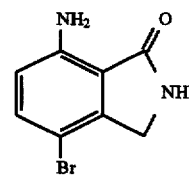

The title compound was obtained as a white powder in a similar manner to that of Preparative Example 9 (yield: 82%).

M.P.: 253° to 258° C. (dec.)
MASS: 227(MH⁺)
$^1$H-NMR(400MHz, DMSO-d$_6$) δ:
4.12(2H, s), 6.20(2H, br s), 6.56(1H, d, J=8.6Hz), 7.32 (1H, d, J=8.6Hz), 8.38(1H, br s)

Preparative Example 23
7-Amino-4-bromoispindoline-1-one

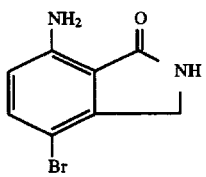

The title compound was obtained as a white powder in a similar manner to that of Preparative Example 9 (yield: 68%).
M.P.: 158° to 180° C. (dec.)
MASS: 241(MH⁺)
¹H-NMR(400MHz, CDCl₃) δ:
3.01(2H, t, J=6.6Hz), 3.48(2H, dt, J=6.6, 2.9Hz), 6.13(2H, br s), 6.19(1H, br s), 6.45(1H, d, J=8.8Hz), 7.32(1H, d, J=8.8Hz)

Preparative Example 24
Methyl 2-amino-5-cyanobenzoate

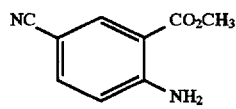

Methyl 2-amino-5-bromobenzoate (5.00 g) was dissolved in 10 ml of N-methyl-2-pyrrolidone, followed by the addition of 2.14 g of cuprous cyanide. The obtained mixture was stirred at 180° C. for 4 hours, followed by the addition of an aqueous solution of ethylenediamine. The resulting mixture was extracted with ethyl acetate. The organic phase was washed with water and a saturated aqueous solution of common salt, dried over anhydrous magnesium sulfate, and concentrated in a vacuum. The residue was purified by silica gel column chromatography (solvent: n-hexane/ethyl acetate (3:1 to 2:1)). The obtained solid was washed with n-hexane to give 2.84 g of the title compound as a slightly yellow powder (yield: 74%).
M.P.: 127° to 130° C.
MASS: 177(MH⁺)
¹H-NMR(400MHz, CDCl₃) δ:
3.90(3H, s), 6.30(2H, br s), 6.67(1H, d, J=8.8Hz), 7.45 (1H, dd, J=8.6, 2.0Hz), 8.20(1H, d, J=2.0Hz)

Preparative Example 25
2-Amino-5-cyanobenzoic acid

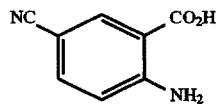

Methyl 2-amino-5-cyanobenzoate (2.84 g) was dissolved in 60 ml of ethanol, followed by the addition of 24 ml of 1N sodium hydroxide. The obtained mixture was stirred at room temperature for 6 hours and concentrated in a vacuum. Water and ether were added to the residue and the resulting aqueous phase was recovered. The ethereal phase was extracted with water. Both of the aqueous phases were combined and acidified with concentrated hydrochloric acid to give precipitates, which were recovered by filtration. The title compound (2.55 g) was obtained as a white powder (yield: 98%).
M.P.: 268° to 272° C.
MASS: 163(MH⁺)
¹H-NMR(400MHz, DMSO-d₆) δ:
6.85(1H, d, J=8.8HZ), 7.49(2H, br s), 7.55(1H, dd, J=8.8, 2.2Hz), 8.03(1H, d, J=2.2Hz)

Preparative Example 26
2-Amino-5-(1,2,4-triazol-1-yl)benzoic acid

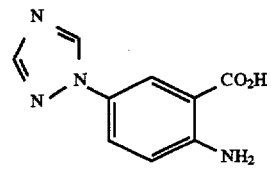

Ethyl 2-amino-5-(1,2,4-triazol-1-yl)benzoate (2.00 g) was suspended in 15 ml of ethanol, followed by the addition of 9.2 ml of 1N sodium hydroxide. The obtained mixture was stirred at 65° C. for one hour and concentrated in a vacuum. Water was added to the residue and the resulting mixture was acidified with concentrated hydrochloric acid to give precipitates. The precipitates were recovered by filtration to give 2.55 g of the title compound as a slightly yellow powder (yield: 100%).
M.P.: 229° to 231° C.
MASS: 235 (MH⁺)
¹H-NMR(400MHz, DMSO-d₆) δ:
8.24–8.27(2H, m), 8.34(1H, m), 8.36(1H, s), 9.57(1H, s)

Preparative Example 27
2-Amino-5-(1-pyrazolyl)benzoic acid

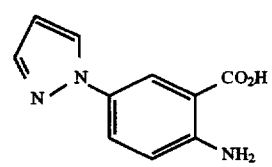

The title compound was obtained as a slightly yellow powder in a similar manner to that of Preparative Example 18 (yield: 100%).
M.P.: 246° to 248° C.
MASS: 234(MH⁺)
¹H-NMR(400MHz, DMSO-d₆) δ:
6.67(1H, dd, J=2.6, 1.8Hz), 7.90(1H, d, J=1.8Hz), 8.18–8.24(2H, m), 8.27(1H, m), 8.79(1H, d, J=2.6Hz)

Preparative Example 28
2-Amino-5-bromo-4-methoxybenzoic acid

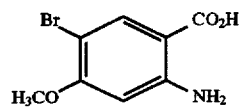

The title compound was obtained as a slightly yellow powder in a similar manner to that of Preparative Example 17 (yield: 97%).
M.P.: 198° C. (dec.)
MASS: 245(MH⁺)
¹H-NMR(400MHz, DMSO-d₆) δ:
3.80(3H, s), 6.42(1H, s), 7.71(1H, s)

Preparative Example 29
5-Chloro-2-chloroacetamido-N-(3-chloro-4-methoxybenzyl)benzamide

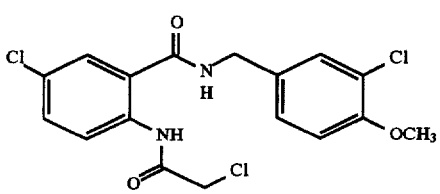

2-Amino-5-chloro-N-(3-chloro-4-methoxybenzyl) benzamide (1.74 g) was dissolved in 18 ml of tetrahydrofuran, followed by the addition of 0.82 ml of triethylamine. Chloroacetyl chloride (0.47 ml) was dropped into the resulting solution under cooling with ice. The obtained mixture was stirred at room temperature for 2 hours, followed by the addition of water. The precipitates formed were recovered by filtration and washed with water and ether to give 1.77 g of the title compound as a slightly cream powder (yield: 82%).

M.P.: 174° to 176° C.
MASS: 401(MH$^+$)
$^1$H-NMR(400MHz, CDCl$_3$) δ:
3.91(3H, s), 4.18(2H, s), 4.54(2H, d, J=5.9Hz), 6.55(1H, m), 6.92(1H, d, J=8.4Hz), 7.22(1H, dd, J=8.4, 2.2Hz), 7.38(1H, d, J=2.2Hz), 7.41(1H, dd, J=8.8, 2.4Hz), 7.44(1H, d, J=2.4Hz), 8.53(1H, d, J=8.8Hz), 11.71(1H, br s)

Preparative Example 30
2-(4-Bromopropionylamino)-5-chloro-N-(3,4-methylenedioxybenzyl)benzamide

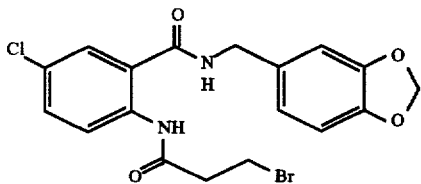

The title compound was obtained as a slightly orange powder in a similar manner to that of Preparative Example 21 (yield: 95%).

M.P.: 170° to 171° C.
MASS: 439(MH$^+$)
$^1$H-NMR(400MHz, CDCl$_3$) δ:
2.88, 3.00(total 2H, t, J=6.8Hz), 3.69, 3.87(total 2H, t, J=6.8Hz), 4.50(2H, d, J=5.5Hz), 5.97(2H, s), 6.49(1H, br m), 6.79(1H, d, J=7.9Hz), 6.81(1H, d, J=7.9Hz), 6.83(1H, s), 7.41(1H, d, J=2.4Hz), 7.41(1H, dd, J=9.5, 2.4Hz), 8.57(1H, d, J=9.8Hz), 11.12(1H, br s)

Preparative Example 31
2-(4-Bromobutyrylamino)-5-chloro-N-(3,4-methylenedioxybenzyl)benzamide

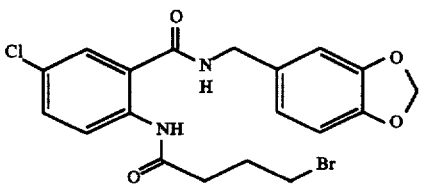

The title compound was obtained as a slightly ocherous powder in a similar manner to that of Preparative Example 21 (yield: 90%).

M.P.: 158° to 159° C.

MASS: 455(MH$^+$)
$^1$H-NMR(400MHz, CDCl$_3$) δ:
2.28(2H, tt, J=7.1, 6.4Hz), 2.61(2H, t, J=7.1Hz), 3.52(2H, t, J=6.4Hz), 4.51(2H, d, J=5.5Hz), 5.98(2H, s), 6.46 (1H, m), 6.78–6.86(3H, m), 7.40(1H, d, J=2.4Hz), 7.40(1H, dd, J=9.5, 2.4Hz), 8.56(1H, d, J=9.5Hz), 11.02(1H, br s)

Preparative Example 32
Ethyl trans-4-[(tert-butoxycarbonyl)amino]-cyclohexanecarboxylate

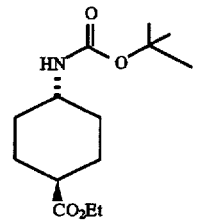

Monoethyl ester of trans-1,4-cyclohexanedicarboxylic acid (10.00 g) was dissolved in 200 ml of tert-butanol, followed by the addition of 7.67 ml of triethylamine and 11.85 ml of diphenylphosphoryl azide. The obtained mixture was heated under reflux for 7 hours and concentrated, followed by the addition of water. The resulting mixture was extracted with ethyl acetate. The organic phase was washed with 1N hydrochloric acid, water, 1N sodium hydroxide, and a saturated aqueous solution of common salt, dried over anhydrous magnesium sulfate, and concentrated in a vacuum. The residue was purified by silica gel column chromatography (solvent: n-hexane/ethyl acetate (8:1 to 4:1)) to give 5.36 g of the title compound as a white solid (yield: 40%).

M.P.: 89° to 91° C.
MASS: 270((M-H)$^+$)
$^1$H-NMR(400MHz, CDCl$_3$) δ:
1.11(2H, m), 1.25(3H, t, J=7.1Hz), 1.44(9H, s), 1.52(2H, m), 1.96–2.15(4H, m), 2.20(1H, dt, J=12.3, 3.5Hz), 3.41(1H, br s), 4.11(2H, q, J=7.1Hz), 4.39(1H, br s)

Preparative Example 33
Ethyl trans-4-[N-(5-bromobutyl)-N-(tert.-butoxycarbonyl)amino]cyclohexanecarboxylate

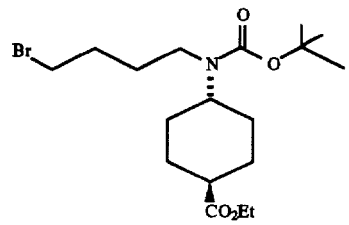

Ethyl trans-4-[(tert.-butoxycarbonyl)amino]-cyclohexanecarboxylate (5.36 g) and 1,5-dibromobutane (13.5 ml) were dissolved in 50 ml of N,N-dimethylformamide, followed by the addition of 0.87 g of 60% sodium hydride. The obtained mixture was stirred at 50° C. for 5 hours and poured onto ice-water. The resulting mixture was extracted with ethyl acetate. The organic phase was washed with 1N hydrochloric acid, water, a saturated aqueous solution of sodium hydrogencarbonate, water, and a saturated aqueous solution of common salt, dried over anhydrous magnesium sulfate, and concentrated in a vacuum. The residue was purified by silica gel column chromatography (solvent: n-hexane/ethyl acetate (10:1 to 5:1)) to give 4.32 g of the title compound as a colorless oil (yield: 52%).

MASS: 420(MH⁺)

¹H-NMR(400MHz, CDCl₃) δ:

1.25(3H, t, J=7.1Hz), 1.35–1.60(17H, m), 1.99–2.12(2H, m), 2.19(1H, m), 3.05(2H, br s), 3.41(2H, t, J=6.8Hz), 3.86(1H, br s), 4.12(2H, q, J=7.1Hz)

Preparative Example 34

Ethyl trans-4-piperidinocyclohexanecarboxylate

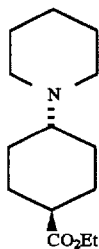

Ethyl trans-4-[N-(5-bromobutyl)-N-(tert.-butoxycarbonyl)amino]cyclohexanecarboxylate (5.92 g) was dissolved in 20 ml of chloroform, followed by the addition of 18 ml of 4N hydrochloric acid/ethyl acetate. The obtained mixture was stirred at room temperature for 14 hours and concentrated. The obtained residue was dissolved in 30 ml of ethanol, followed by the addition of 5.85 g of anhydrous potassium carbonate. The obtained mixture was stirred at room temperature for 3 hours, then at 80° C. for 6 hours, followed by the addition of Celite. The resulting mixture was freed from insolubles by filtration and concentrated in a vacuum. The residue was purified by silica gel column chromatography (solvent: dichloromethane/methanol/concentrated aqueous ammonia (1000:100:2)) to give 1.91 g of the title compound as a pale-yellow oil (yield: 57%).

MASS: 240(MH⁺)

¹H-NMR(400MHz, CDCl₃) δ:

1.25(3H, t, J=7.1Hz), 1.28(2H, m), 1.38–1.51(4H, m), 1.54–1.62(4H, m), 1.95(2H, m), 2.04(2H, m), 2.15–2.31(2H, m), 2.48–2.53(4H, m), 4.11(2H, q, J=7.1Hz)

Preparative Example 35 trans-4-Piperidinocyclohexanecarboxylic acid

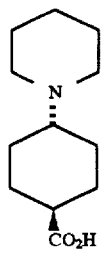

Ethyl trans-4-piperidinocyclohexanecarboxylate (1.91 g) was dissolved in 20 ml of ethanol. The obtained solution was stirred at room temperature for 3 days, adjusted to pH7 with 1N hydrochloric acid, concentrated in a vacuum, and purified with an ODS column (solvent: water), followed by the addition of water. The resulting mixture was freed from insolubles by filtration and concentrated in a vacuum, followed by the addition of methanol. The obtained mixture was freed from insolubles by filtration and concentrated in a vacuum. The obtained solid was washed with ether to give 1.54 g of the title compound as a slightly yellow powder (yield: 91%).

MASS: 212(MH⁺)

¹H-NMR(400MHz, CDCl₃) δ:

1.14–1.32(4H, m), 1.36(2H, m), 1.41–1.49(4H, m), 1.73 (2H, m), 1.88(2H, m), 1.96(1H, m), 2.19(1H, m), 2.36–2.48(4H, m)

Preparative Example 36

N-(3,4-Methylenedioxybenzyl)-2-nitro-5-(1-pyrazolyl) benzamide

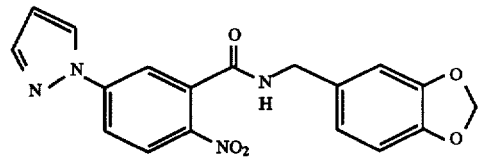

2-Nitro-5-(1-pyrazolyl)benzoic acid (1.40 g), piperonylamine (0.82 ml), 1-(3-dimethylaminopropyl)-3-ethylcarbodiimide hydrochloride (1.27 g), 1-hydroxybenzotriazole (0.89 g) and triethylamine (0.92 ml) were added to 20 ml of N,N-dimethylformamide. The obtained mixture was stirred at room temperature for 14 hours, followed by the addition of water. The precipitates formed were recovered by filtration to give 2.19 g of the title compound as a slightly yellow powder (Yield: 100%).

M.P.: 179° to 180° C.

MASS: 367(MH⁺)

¹H-NMR(400 MHz, CDCl₃) δ:

4.56(2H, d, J=5.5 Hz), 5.95(2H, s), 6.18(1H, m), 6.56(1H, dd, J=2.6, 1.8 Hz), 6.78(1H, d, J=7.9 Hz), 6.85(1H, dd, J=7.9, 1.6Hz), 6.91(1H, d, J=1.6 Hz), 7.78(1H, d, J=1.8 Hz), 7.83(1H, dd, J=9.0, 2.4 Hz), 7.86(1H, d, J=2.4 Hz), 8.01(1H, d, J=2.6 Hz), 8.19(1H, d, J=9.0 Hz)

Preparative Example 37

N-(3,4-Methylenedioxybenzyl)-2-nitro-5-(1,2,4-triazol-1-yl)benzamide

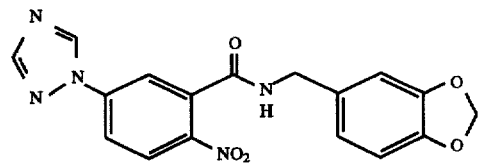

The title compound was obtained as a slightly ocherous powder in a similar manner to that of Preparative Example 28 (yield: 84%).

M.P.: 187° to 190° C.

MASS: 388(MH⁺)

¹H-NMR(400 MHz, CDCl₃) δ:

4.58(2H, d, J=5.5 Hz), 5.97(2H, s), 6.12(1H, br), 6.76(1H, d, J=7.9 Hz), 6.86(1H, dd, J=7.9, 1.7 Hz), 6.91(1H, d, J=1.7 Hz), 7.91(1H, dd, J=9.5, 2.6 Hz), 7.91(1H, d, J=2.6 Hz), 8.18(1H, s), 8.27(1H, d, J=9.5 Hz), 8.69(1H, s)

Preparative Example 38
N-(4-Chloro-3-methoxybenzyl)phthalimide

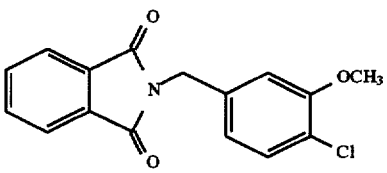

2-Chloro-5-methylanisole (8.00 g), N-bromo-succinimide (9.55 g) and benzoyl peroxide (0.62 g) were added to 170 ml of carbon tetrachloride. The obtained mixture was heated under reflux for one hour and cooled by allowing to stand. The resulting mixture was freed from insolubles by filtration and concentrated in a vacuum. The obtained residue was dissolved in 100 ml of N,N-dimethylformamide, followed by the addition of 10.41 g of potassium phthalimide. The obtained mixture was stirred at 50° C. for one hour, followed by the addition of ice-water. The precipitates formed were recovered by filtration and washed with water and ether to give 8.66 g of the title compound as a slightly yellow powder (yield: 52%).

M.P.: 156° to 159° C.
MASS: 301(MH$^+$)
$^1$H-NMR(400 MHz, CDCl$_3$) δ:
3.90(3H, s), 4.80(2H, s), 6.98(1H, dd, J=8.1, 1.8 Hz), 7.05(1H, d, J=1.8 Hz), 7.29(1H, d, J=8.1 Hz), 7.69–7.75(2H, m), 7.82–7.88(2H, m)

Preparative Example 39
N-[(2-Methoxy-5-pyridyl)methyl]phthalimide

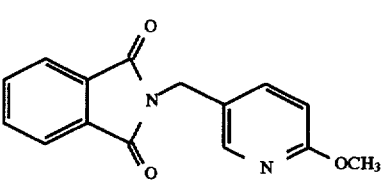

2-Methoxy-5-pyridinemethanol (2.79 g), phthalimide (2.92 g) and triphenylphosphine (5.71 g) were added to 35 ml of tetrahydrofuran. The obtained mixture was cooled with ice, followed by the dropwise addition of a solution of 3.43 ml of diethyl azodicarboxylate in 5 ml of tetrahydrofuran. The resulting mixture was stirred under cooling with ice for one hour, then at room temperature for 15 hours, and poured onto ice-water. The resulting mixture was extracted with ethyl acetate. The organic phase was washed with 1N hydrochloric acid, water, a saturated aqueous solution of sodium hydrogencarbonate, water, and a saturated aqueous solution of common salt, dried over anhydrous magnesium sulfate, and concentrated in a vacuum, followed by the addition of benzene. The resulting mixture was freed from insolubles by filtration and concentrated in a vacuum. The residue was purified by silica gel column chromatography (solvent: n-hexane/ethyl acetate (3:1)). The obtained solid was washed with n-hexane to give 4.07 g of the title compound as a white powder (yield: 77%).

M.P.: 122° to 124° C.
MASS: 269(MH$^+$)
$^1$H-NMR(400 MHz, CDCl$_3$) δ:
3.90(3H, s), 4.78(2H, s), 6.99(1H, d, J=8.6 Hz), 7.68(1H, dd, J=8.6, 2.6 Hz), 7.68–7.74(2H, m), 7.81–7.87(2H, m), 8.27(1H, d, J=2.6 Hz)

Preparative Example 40
N-(3-Formyl-4-methoxybenzyl)phthalimide

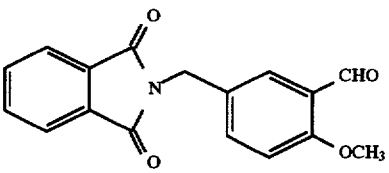

N-(4-Methoxybenzyl)phthalimide (14.00 g) was dissolved in 100 ml of trifluoroacetic acid, followed by the addition of 8.09 g of hexamethylenetetramine in portions. The resulting mixture was stirred at room temperature for one hour and heated under reflux for 3.5 hours, followed by the addition of ice-water. The obtained mixture was extracted with ethyl acetate. The organic phase was washed with 1N sodium hydroxide to give insolubles, which were recovered by filtration. The organic phase was washed with water and a saturated aqueous solution of common salt, dried over anhydrous magnesium sulfate, and vacuum-distilled to remove the solvent. The obtained solid and the above insolubles were combined and washed with ethyl acetate to give 13.13 g of the title compound as a slightly yellow powder (yield: 85%).

M.P.: 177° to 179° C.
MASS: 296 (MH$^+$)
$^1$H-NMR(400 MHz, CDCl$_3$) δ:
3.90(3H, s), 4.82(2H, s), 6.95(1H, d, J=8.6 Hz), 7.64(1H, dd, J=8.6, 2.4 Hz), 7.69–7.74(2H, m), 7.82–7.87(3H, m), 10.41(1H, s)

Preparative Example 41
N-(3-Hydroxyimino-4-methoxybenzyl)phthalimide

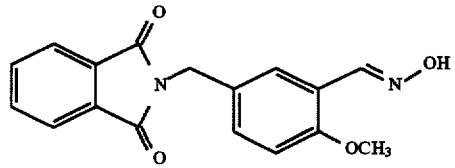

N-(3-Formyl-4-methoxybenzyl)phthalimide (12.50 g) was suspended in 200 ml of tetrahydrofuran, followed by the addition of 3.24 g of hydroxylamine hydrochloride, 7.64 g of sodium acetate and 30 ml of water. The obtained mixture was stirred at 60° C. for 30 minutes and concentrated in a vacuum. The precipitates formed were recovered by filtration and washed with ether to give 11.51 g of the title compound as a slightly yellow powder (yield: 88%).

M.P.: 214° to 217° C.
MASS: 311(MH$^+$)
$^1$H-NMR(400 MHz, CDCl$_3$) δ:
3.25(1H, br s), 3.82(3H, s), 4.79(2H, s), 6.85(1H, d, J=8.6 Hz), 7.44(1H, dd, J=8.6, 2.4 Hz), 7.66–7.72(2H, m), 7.78(1H, d, J=2.4 Hz), 7.80–7.86(2H, m), 8.42(1H, s)

Preparative Example 42
N-(3-Cyano-4-methoxybenzyl)phthalimide

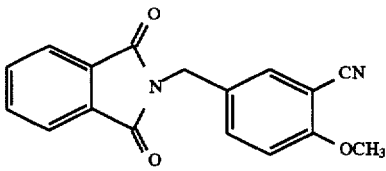

N-(3-Hydroxyimino-4-methoxybenzyl)phthalimide (11.00 g) was suspended in 120 ml of xylene, followed by the addition of 3.68 ml of acetic anhydride. The obtained mixture was heated under reflux for 14 hours and cooled by allowing to stand. The precipitates formed were recovered by filtration and washed with xylene to give 9.11 g of the title compound as a white powder (yield: 88%).
M.P.: 205° to 209° C.
MASS: 293(MH$^+$)
$^1$H-NMR(400 MHz, CDCl$_3$) δ:
3.90(3H, s), 4.78(2H, s), 6.92(1H, m), 7.62–7.66(2H, m), 7.70–7.76(2H, m), 7.83–7.88(2H, m)

Preparative Example 43
4-Chloro-3-methoxybenzylamine hydrochloride

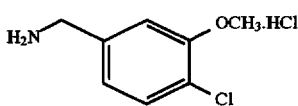

N-(4-Chloro-3-methoxybenzyl)phthalimide (8.40 g) and hydrazine monohydrate (1.49 ml) were added to 100 ml of ethanol. The obtained mixture was heated under reflux for 1.5 hours, freed from insolubles by filtration, and concentrated in a vacuum, followed by the addition of 1N hydrochloric acid. The resulting mixture was freed from insolubles by filtration. The aqueous phase was washed with ether, alkalified with concentrated aqueous ammonia and extracted with ether. The ethereal phase was dried over anhydrous sodium sulfate and concentrated in a vacuum. The residue was dissolved in ethyl acetate, followed by the addition of 4N hydrogen chloride/ethyl acetate. The precipitates formed were recovered by filtration and washed with ethyl acetate to give 4.83 g of the title compound as a white powder (yield: 83%).
M.P.: 237° to 242° C.
MASS: 172(MH$^+$)
$^1$H-NMR(400 MHz, DMSO-d$_6$) δ:
3.88(3H, s), 4.01(2H, s), 7.07(1H, dd, J=8.0, 1.8 Hz), 7.45(1H, d, J=8.0 Hz), 7.46(1H, d, J=1.8 Hz), 8.57(3H, br s)

Preparative Example 44
5-Aminomethyl-2-methoxypyridine dihydrochloride

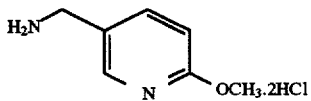

The title compound was obtained as a white powder in a similar manner to that of Preparative Example 36 (yield: 58%).
M.P.: 165° C. (dec.)
MASS: 139(MH$^+$)
$^1$H-NMR(400 MHz, DMSO-d$_6$) δ:
3.87(3H, s), 3.98(2H, q, J=5.9 Hz), 6.89(1H, d, J=8.4 Hz), 7.94(1H, dd, J=8.4, 2.4 Hz), 8.14(1H, m), 8.29(1H, d, J=2.4 Hz), 8.58(2H, br s)

Preparative Example 45
3-Cyano-4-methoxybenzylamine

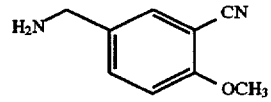

N-(3-Cyano-4-methoxybenzyl)phthalimide (8.60 g) and hydrazine monohydrate (1.71 ml) were dissolved in a solvent mixture comprising 100 ml of ethanol and 100 ml of 1,4-dioxane. The obtained solution was heated under reflux for 2 hours, freed from insolubles by filtration, and concentrated in a vacuum, followed by the addition of 1N sodium hydroxide. The resulting mixture was extracted with chloroform. The organic phase was dried over anhydrous potassium carbonate and concentrated in a vacuum. The residue was purified by silica gel column chromatography (solvent: dichloro-methane/methanol/concentrated aqueous ammonia (100:10:1)) to give 4.24 g of the title compound as a slightly yellow solid (yield: 89%).
MASS: 163(MH$^+$)
$^1$H-NMR(400 MHz, CDCl$_3$) δ:
1.40(2H, s), 3.84(2H, s), 3.92(3H, s), 6.94(1H, d, J=8.4 Hz), 7.49–7.54 (2H, m)

EXAMPLE 1

2-Amino-5-chloro-N-(3,4-methylenedioxybenzyl)benzamide hydrochloride

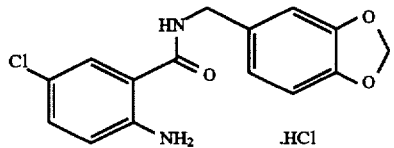

(1) 2-Nitro-5-chlorobenzoic acid (5.0 g) and thionyl chloride (3 ml) were heated together under reflux in 50 ml of benzene for 4 hours, cooled and concentrated to give an acid chloride. This acid chloride was added to a solution of 3.2 ml of piperonylamine and 5 ml of triethylamine in THF to conduct a reaction. The reaction mixture was post-treated in a conventional manner and recrystallized from ethyl acetate to give 5.8 g of 5-chloro-N-(3,4-methylenedioxybenzyl)-2-nitrobenzamide.
NMR(CDCl$_3$: δ)
4.56(2H, d, J=5.7 Hz), 5.97(2H, s+1H, br.s), 6.80(1H, d, J=7.9 Hz), 6.85(1H, dd, J=7.9 Hz, 1.8 Hz), 6.90(1H, d, J=1.8 Hz), 7.50(1H, d, J=2.2 Hz), 7.54(1H, dd, J=8.6 Hz, 2.2 Hz), 8.05(1H, d, J=8.6 Hz)

(2) 5-Chloro-N-(3,4-methylenedioxybenzyl)-2-nitrobenzamide (620 mg), acetic acid (1 ml), water (1 ml) and ethanol (20 ml) were mildly heated together under reflux, followed by the addition of 1.0 g of powdered iron in portions under stirring. The obtained mixture was refluxed for one hour and filtered under heating to remove brown insolubles. The filtrate was concentrated, followed by the addition of ethanol. The resulting mixture was dissolved by heating. Concentrated hydrochloric acid was added to the obtained solution in portions, by which the brown solution turned yellow and transparent. This yellow transparent solution was seeded to give crystals. The resulting mixture was cooled and filtered to recover the crystals. The crystals were washed with ethanol and ether and dried to give 520 mg of 2-amino-5-chloro-N-(3,4-methylenedioxybenzyl)benzamide.

M.P.: 225° to 228° C. (dec.)
MASS: 305(M-HCl.H⁺)
NMR(400 MHz, δ, DMSO-d₆)

4.32(2H, d, J=5.6 Hz), 5.07(3H, brs), 5.98(2H, s), 6.78 (1H, dd, J=8.0, 1.2 Hz), 6.84(1H, d, J=8.0 Hz), 6.85 (1H, d, J=8.8 Hz), 6.89(1H, d, J=1.2 Hz), 7.23(1H, dd, J=8.8, 2.4 Hz), 7.65(1H, d, J=2.4 Hz), 8.94(1H, t, J=5.6 Hz)

EXAMPLE 2

2-Amino-5-chloro-N-(3,4-methylendioxybenzyl)benzamide

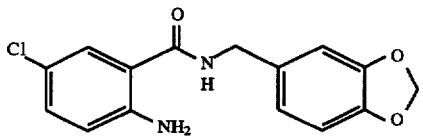

2-Amino-5-chlorobenzoic acid (10.0 g), 3,4-methylenedioxybenzyamine (7.62 ml), 1-(3-dimethylaminopropyl)-3-ethylcarbodiimide hydrochloride (11.74 g), N-hydroxybenzotriazole (8.27 g) and triethylamine (8.53 ml) were added to 200 ml of acetonitrile. The obtained mixture was stirred at room temperature for 20 hours and concentrated, followed by the addition of water. The resulting mixture was extracted with ethyl acetate. The organic phase was washed with 1N hydrochloric acid, a saturated aqueous solution of sodium hydrogencarbonate, and a saturated aqueous solution of common salt successively, dried over anhydrous magnesium sulfate, and concentrated. The obtained solid was washed with ethanol to give 14.13 g of the title compound as a slightly orange powder (yield: 80%).

M.P.: 142° to 145° C.
(white needle from EtOH)
NMR(400 MHz, δ, CDCl₃)

4.49(d, J=5.7 Hz, 2H), 5.48–5.58(br, 2H), 5.96(s, 2H), 6.22(br, 1H), 6.63(d, J=8.8 Hz, 1H), 6.78(d, J=7.9 Hz, 1H), 6.81(dd, J=0.5, 7.9 Hz, 1H), 6.84(d, J=0.5 Hz, 1H), 7.15(dd, J=2.4, 8.8 Hz, 1H), 7.26(d, J=2.4 Hz, 1H)

EXAMPLE 3

2-Amino-5-bromo-N-(3,4-methylenedioxybenzyl)benzamide

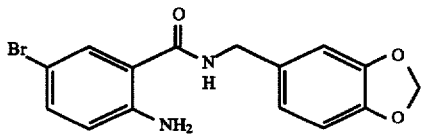

A pale-cream needle was obtained (yield: 92%).
M.P.: 157° to 158° C.
(palely orangish-yellow needle from EtOH)
NMR(400 MHz, δ, CDCl₃)

4.49(d, J=5.7 Hz, 2H), 5.57(br, 2H), 5.97(s, 2H), 6.20(br, 1H), 6.58(d, J=8.8 Hz, 1H), 6.78(dd, J=0.7, 7.9 Hz, 1H), 6.81(dd, J=1.3, 7.9 Hz, 1H), 6.84(dd, J=0.7, 1.3 Hz, 1H), 7.27(dd, J=2.2, 8.8 Hz, 1H), 7.39(d, J=2.2 Hz, 1H)

EXAMPLE 4

2-Amino-5-chloro-N-methyl-N-(3,4-methylenedioxybenzyl)benzamide

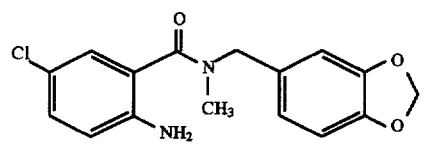

The title compound was obtained as a pale-yellow powder (yield: 91%).

M.P.: 122° to 124° C.
(slightly yellow needle, aq. EtOH).
NMR(400 MHz, δ, CDCl₃)

2.9(s, 3H), 4.34(s, 2H), 4.55(br, 2H), 5.96(s, 2H), 6.60–6.88(m, 4H), 6.66(d, J=8.6 Hz), 6.77(d, J=7.7 Hz), 7.06–7.13(m, 2H)

EXAMPLE 5

2-Amino-5-dimethylaminomethyl-N-(3,4-methylenedioxybenzyl)benzamide

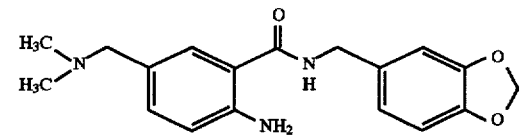

Methyl 2-amino-5-((dimethylamino)methyl)benzoate (10.98 g) was dissolved in 100 ml of ethanol, followed by the addition of 63.1 ml of 1N sodium hydroxide. The obtained mixture was stirred at room temperature for 14 hours, then at 100° C. for 4 hours, followed by the addition of 68.1 ml of 1N hydrochloric acid. The resulting mixture was concentrated to give a pale-yellow powder.

This powder was dissolved in 270 ml of acetonitrile containing 50% of water, followed by the addition of 7.19 ml of 3,4-methylenedioxybenzylamine, 11.93 g of 1,3-dicyclohexylcarbodiimide and 7.81 g of N-hydroxybenztriazole. The obtained mixture was stirred at 70° C. for 14 hours and filtered to remove insolubles. A saturated aqueous solution of sodium hydrogencarbonate was added to the filtrate, followed by the extraction with chloroform. The organic phase was dried over anhydrous magnesium sulfate and distilled to remove the solvent. The residue was purified by silica gel column chromatography (solvent: dichloromethane/methanol/concentrated aqueous ammonia (1000:100:3)) to give 15.45 g of the title compound as a pale-yellow solid (yield: 90%).

NMR(400 MHz, δ, CDCl₃)

2.26(s, 6H), 3.35(s, 2H), 4.49(d, J=5.9 Hz, 2H), 5.58(br, 2H), 5.95(s, 2H), 6.63(d, J=8.4 Hz, 1H), 6.70(br, 1H), 6.77(d, J=7.9 Hz, 1H), 6.82(dd, J=1.6, 7.9 Hz, 1H) 6.87(d, J=1.6 Hz, 1H), 7.10(dd, J=1.6, 8.4 Hz, 1H), 7.39(d, J=1.6 Hz, 1H)

EXAMPLE 6

Ethyl 1-[[4-chloro-2-(3,4-methylenedioxybenzyl)carbamoyl phenyl]carbamoyl]piperidine-4-carboxylate

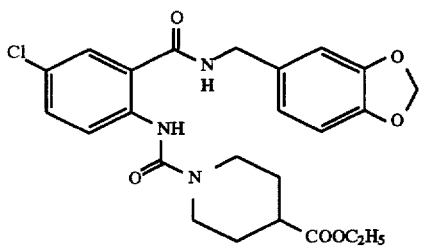

Ethyl 1-[(2-carboxy-4-chlorophenyl)carbamoyl]-piperidine-4-carboxylate (850 mg), 3,4-methylenedioxybenzylamine (0.45 ml), 1,3-dicyclohexylcarbodiimide (0.54 g), N-hydroxybenztriazole (0.36 g) and 4-dimethylaminopyridine (in a catalytic amount) were added to 10 ml of N,N-dimethylformamide. The obtained mixture was stirred at room temperature for 16 hours, followed by the addition of water and ethyl acetate. The resulting mixture was filtered to remove insolubles, followed by the recovery of the organic phase. The organic phase was washed with 1N hydrochloric acid, a saturated aqueous solution of sodium hydrogencarbonate, and a saturated aqueous solution of common salt, dried over anhydrous magnesium sulfate, and distilled to remove the solvent. The residue was purified by silica gel column chromatography (solvent: dichloromethane/methanol (30:1)) to give 1.10 g of the title compound as a white solid (yield: 99%).

M.P.: 153° to 155° C. (white needle from aq. EtOH)
NMR(400 MHz, δ, CDCl₃)

1.27(t, J=7.1 Hz, 3H), 1.75(m, 2H), 1.99(m, 2H), 2.52(m, 1H), 3.04(m, 2H), 4.08(m, 2H), 4.16(q, J=7.1 Hz, 2H), 4.47(d, J=5.7 Hz), 5.97(s, 2H), 6.79(dd, J=0.5, 7.9 Hz, 1H), 6.82(dd, J=1.5, 7.9 Hz, 1H), 6.86(dd, J=0.5, 1.5 Hz, 1H), 7.01(t, J=5.7 Hz, 1H), 7.24(dd, J=2.6, 9.0 Hz, 1H), 7.32(d, J=2.6 Hz, 1H), 8.22(d, J=9.0 Hz, 1H), 10.57(s, 1H)

EXAMPLE 7

Ethyl 1-[[4-chloro-2-(3-chloro-4-methoxybenzyl)carbamoyl]phenyl]carbamoylpiperidine-4-carboxylate

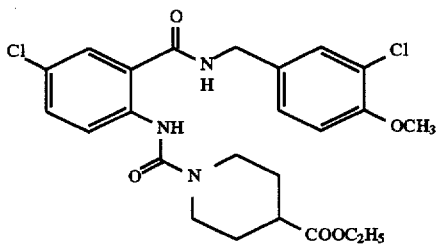

A white powder was obtained (yield: 96%).
M.P.: 131° to 132° C. (white needle from aq. EtOH)
NMR(400 MHz, δCDCl₃)

1.27(t, J=7.1 Hz, 3H), 1.75(m, 2H), 1.99(m, 2H), 2.52(m, 1H), 3.05(m, 1H), 3.91(s, 3H), 4.08(m, 2H), 4.16(q, J=7.1 Hz, 2H), 4.48(d, J=5.7 Hz, 2H), 6.93(d, J=8.4 Hz, 1H), 7.12(t, J=5.7 Hz, 1H), 7.22(dd, J=2.4, 9.0 Hz, 1H), 7.22(dd, J=2.2, 8.4 Hz, 1H), 7.32(d, J=2.4 Hz, 1H), 7.40(d, J=2.2 Hz, 1H), 8.19(d, J=9.0 Hz, 1H), 10.54(s, 1H)

EXAMPLE 8

Ethyl 1-[[4-chloro-2-[(2,3-dihydrobenzofuran-5-yl)methyl]carbamoyl]phenyl]piperidine-4-carboxylate

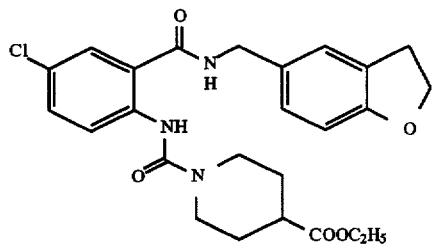

A white powder was obtained (yield: 96%).
M.P.: 120° to 122° C. (white needle from aq. EtOH)
NMR(400 MHz, δ, CDCl₃)

1.27(t, J=7.1 Hz, 3H), 1.75(m, 2H), 2.00(m, 2H), 2.52(m, 1H), 3.05(m, 2H), 3.22(t, J=8.8 Hz, 2H), 4.10(m, 2H), 4.16(q, J=7.1 Hz, 2H), 4.49(d, J=5.5 Hz, 2H), 4.59(t, J=8.8 Hz, 2H), 6.69(t, J=5.5 Hz, 1H), 6.77(d, J=8.1 Hz, 1H), 7.09(dd, J=1.8, 8.1 Hz, 1H), 7.19(d, J=1.8 Hz, 1H), 7.28(dd, J=2.4, 9.2 Hz, 1H), 7.33(d, J=2.4 Hz, 1H), 8.29(d, J=9.2 Hz, 1H), 10.68 (s, 1H)

EXAMPLE 9

5-Chloro-N-(3,4-methylenedioxybenzyl)-2-(isonicotinoylamino)benzamide

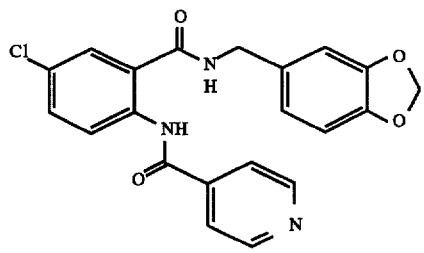

2-Amino-5-chloro-N-(3,4-methylenedioxybenzyl)benzamide (1.0 g) was dissolved in 10 ml of pyridine, followed by the addition of 0.64 g of isonicotinoyl chloride hydrochloride. The obtained mixture was stirred at room temperature for one hour, followed by the addition of ice-water. The resulting mixture was extracted with ethyl acetate. The organic phase was washed with 1N hydrochloric acid, a saturated aqueous solution of sodium hydrogencarbonate, and a saturated aqueous solution of common salt successively, dried over anhydrous magnesium sulfate, and distilled to remove the solvent. The residue was purified by silica gel column chromatography (solvent: dichloro-methane/methanol (50:1)) and recrystallized from ethyl acetate to give 630 mg of the title compound as a white needle (yield: 47%).

M.P.: 204° to 205° C. (EtOAc)
MASS: (FAB)410(MH⁺)
Elemental analysis:

calcd. C(%) H(%) N(%)
61.55 3.94 10.25
found C(%) H(%) N(%)
61.58 3.99 10.16

NMR(400 MHz, δ, DMSO-d₆)
4.44(d, J=5.9 Hz, 2H), 5.99(s, 2H), 6.85(dd, J=1.5, 8.1 Hz, 1H), 6.87(dd, J=0.5, 8.1 Hz, 1H), 6.96(dd, J=0.5, 1.5 Hz, 1H), 7.66(dd, J=2.4, 9.0 Hz, 1H), 7.78–7.82(m, 2H), 7.99(d, J=2.4 Hz, 1H), 8.60(d, J=9.0 Hz, 1H), 8.82–8.87(m, 2H), 9.49(t, J=5.9 Hz, 1H), 12.62(s, 1H)

EXAMPLE 10

5-Chloro-2-(nicotinoylamino)-N-(3,4-methylenedioxybenzyl)benzamide

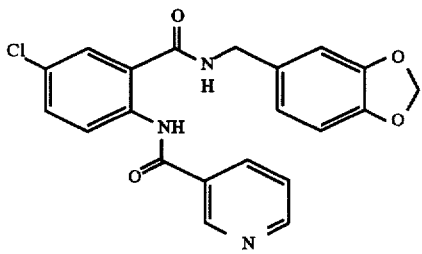

A white needle was obtained (yield: 81%).
M.P.: 152° to 154° C. (ethyl acetate)
MASS: (FAB)410(MH$^+$)
Elemental analysis:
calcd. C(%) H(%) N(%)
61.55 3.94 10.25
found C(%) H(%) N(%)
61.42 3.89 10.23
NMR(400 MHz, δ, CDCl$_3$)
4.54(d, J=5.5 Hz, 2H), 5.96(s, 2H), 6.79(dd, J=0.5, 7.9 Hz, 1H), 6.82(br, 1H), 6.82(dd, J=1.6, 7.9 Hz), 6.85(dd, J=0.5, 1.6 Hz, 1H), 7.43–7.48(m, 2H), 7.50(d, J=2.4 Hz, 1H), 8.28(ddd, J=1.6, 2.4, 8.1 Hz, 1H), 8.75(d, J=8.8 Hz, 1H), 8.78(dd, J=1.6, 4.8 Hz, 1H), 9.26(dd, J=0.4, 2.4 Hz, 1H), 12.28(s, 1H)

EXAMPLE 11

5-Chloro-2-chloroacetamido-N-(3,4-methylenedioxybenzyl)benzamide

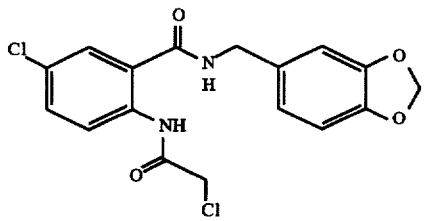

2-Amino-5-chloro-N-(3,4-methylenedioxybenzyl)benzamide (5.00 g) was dissolved in 60 ml of tetrahydrofuran, followed by the addition of 2.52 ml of triethylamine. The obtained mixture was stirred under cooling with ice. Chloroacetyl chloride (1.44 ml) was dropped into the resulting mixture in such a way that the temperature of the mixture did not exceed 10° C. After one hour, ice-water was added to the obtained mixture, followed by the extraction with ethyl acetate. The organic phase was washed with 1N hydrochloric acid, a saturated aqueous solution of sodium hydrogencarbonate, and a saturated aqueous solution of common salt successively, dried over anhydrous magnesium sulfate, and distilled to remove the solvent. The obtained solid was washed with a small amount of ethyl acetate to give 5.37 g of the title compound as a slightly yellow powder (yield: 86%).
M.P.: 186° to 187° C. (white needle from EtOH)
NMR(400 MHz, δ, CDCl$_3$)
4.18(s, 2H), 4.52(d, J=5.5 Hz, 2H), 5.98(s, 2H), 6.49(br, 1H), 6.79(dd, J=0.5, 7.9 Hz, 1H), 6.82(dd, J=1.6, 7.9 Hz, 1H), 6.85(dd, J=0.5, 1.6 Hz, 1H), 7.42(dd, J=2.6, 8.6 Hz, 1H), 7.44(d, J=2.6 Hz, 1H), 8.54(d, J=8.6 Hz, 1H), 11.75(br, 1H)

EXAMPLE 12

2-Acetamido-5-chloro-N-(3,4-methylenedioxybenzyl)benzamide

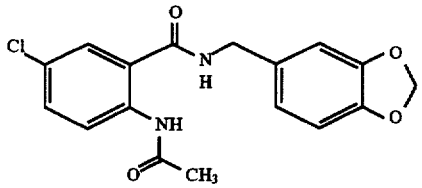

2-Amino-5-chloro-N-(3,4-methylenedioxybenzyl)benzamide hydrochloride (100 mg) was reacted with 40 μl of acetyl chloride in 5 ml of tetrahydrofuran in the presence of 150 μl of diisopropylethylamine. The reaction mixture was subjected to extraction with ethyl acetate and water and recrystallization from ethyl acetate/hexane to give 85 mg of 2-acetamido-5-chloro-N-( 3,4-methylenedioxybenzyl)benzamide (yield: 84%).

M.P.: 187° to 188° C. (dec.)

MASS: 347(MH$^+$)

NMR(400 MHz, δ, CDCl$_3$)

2.21(3H, s), 4.51(2H, d, J=5.5 Hz), 5.98(2H, s), 6.41(1H, brs), 6.81(2H, s), 6.84(1H, s), 7.38–7.42(2H, m), 8.57 (1H, d, J=8.8 Hz), 10.91(1H, brs)

EXAMPLE 13

5-Chloro-N-(3,4-methylenedioxybenzyl)-2-phenoxycarbonylaminobenzamide

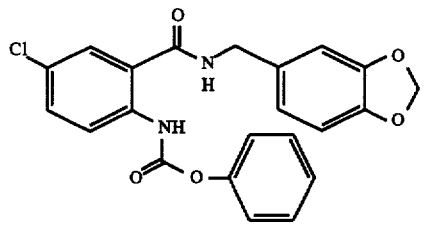

2-Amino-5-chloro-N-(3,4-methylenedioxybenzyl)benzamide hydrochloride (100 mg) was reacted with 50 μl of phenyl chlorocarbonate in 5 ml of tetrahydrofuran in the presence of 150 μl of diisopropylethylamine. The reaction mixture was subjected to extraction with ethyl acetate and water and recrystallization from ethyl acetate/hexane to give 110 mg of 5-chloro-N-(3,4-methylenedioxybenzyl)-2-phenoxycarbonylaminobenzamide (yield: 88%).

M.P.: 149° to 150° C.

NMR(400 MHz, δ, CDCl$_3$)

4.54(2H, d, J=5.6 Hz), 5.98(2H, s), 6.41(1H, brs), 6.80–6.87(3H, m), 7.17–7.28(2H, m), 7.37–7.46(5H, m), 8.38(1H, d, J=9.2 Hz), 10.82(1H, s)

EXAMPLE 14

5-Chloro-2-[[trans-4-(ethoxycarbonyl)cyclohexanecarbonyl]amino]-N-(3,4-methylenedioxybenzyl)benzamide

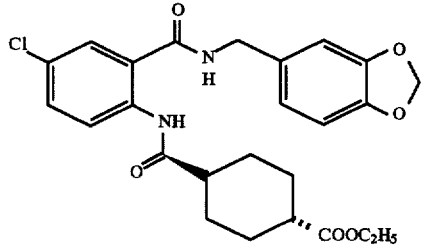

2-Amino-5-chloro-N-(3,4-methylenedioxybenzyl)benzamide (1.5 g) was dissolved in 15 ml of pyridine, followed by cooling with ice. A solution of 2.28 g of trans-4-(ethoxycarbonyl)cyclohexanecarbonyl chloride in 5 ml of dichloromethane was dropped into the solution prepared above in such a way that the reaction temperature did not exceed 10° C. The obtained mixture was stirred for 2 hours, followed by the addition of ice-water. The resulting mixture was extracted with ethyl acetate. The organic phase was washed with 1N hydrochloric acid, a saturated aqueous solution of sodium hydrogencarbonate, and a saturated aqueous solution of common salt successively, dried over anhydrous magnesium sulfate, and distilled to remove the solvent. The residue was purified by silica gel column chromatography (solvent: n-hexane/ethyl acetate (3:1)) and crystallized from ether to give 1.30 g of the title compound as a colorless prism (yield: 55%).

M.P.: 156° to 158° C. (white needle from aq. EtOH)
NMR(400 MHz, δ, CDCl₃)
1.26(t, J=7.1 Hz, 3H), 1.43–1.62(m, 4H), 2.06–2.14(m, 4H), 2.22–2.36(m, 2H), 4.13(q, J=7.1 Hz, 2H), 4.50(d, J=5.7 Hz, 2H), 5.97(s, 2H), 6.70(t, J=5.7 Hz, 1H), 6.76–6.85(m, 3H), 7.32(dd, J=2.4, 9.0 Hz, 1H), 7.41(d, J=2.4 Hz, 1H), 8.54(d, J=9.0, 1H), 11.02(s, 1H)

EXAMPLE 15

5-Bromo-2-[[trans-4-(ethoxycarbonyl)cyclohexanecarbonyl]amino]-N-(3,4-methylenedioxybenzyl)benzamide

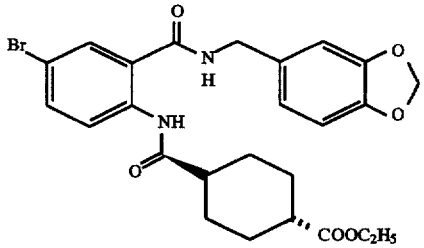

A white powder was obtained (yield: 79%).
M.P.: 147° to 149° C. (white needle from n-Hex/EtOAc)
NMR(400 MHz, δ, CDCl₃)
1.28(t, J=7.1 Hz, 3H), 1.44–1.53(m, 4H), 2.07–2.15(m, 4H), 2.25–2.37(m, 2H), 4.13(q, J=7.1 Hz, 2H), 4.51(d, J=5.7 Hz, 2H), 5.98(s, 2H), 6.51(t like, J=5 Hz, 1H), 6.78–8.83(m, 2H), 6.84(d, J=0.9 Hz, 1H), 7.53(dd, J=2.4, 8.4 Hz, 1H), 7.55(d, J=2.4 Hz, 1H), 8.53(d, J=8.4 Hz, 1H), 11.02(s, 1H)

EXAMPLE 16

5-Chloro-2-[[3-(ethoxycarbonyl)acryloyl]amino]-N-(3,4-methylenedioxybenzyl)benzamide

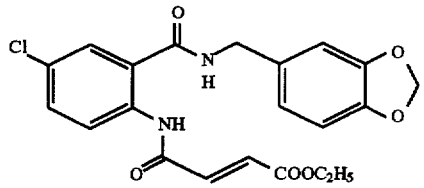

A slightly yellow needle was obtained (yield: 32%).
M.P.: 181° to 184° C. (ethyl acetate)
MASS: (FAB)431(MH⁺)
Elemental analysis:
calcd. C(%) H(%) N(%)
58.54 4.44 6.50
found C(%) H(%) N(%)
58.44 4.41 6.49
NMR(400 MHz, δ, CDCl₃)
1.35(t, J=7.1 Hz, 3H), 4.28(q, J=7.1 Hz, 2H), 4.52(d, J=5.7 Hz, 2H), 5.98(s, 2H), 6.53(m, 1H), 6.78–6.86(m, 3H), 6.90(d, J=15.4 Hz, 1H), 7.08(d, J=15.4 Hz, 1H), 7.42–7.48(m, 2H), 8.69(d, J=9.7 Hz, 1H), 11.57(s, 1H)

EXAMPLE 17

5-chloro-2-[[5-(ethoxycarbonyl)valeryl]amino]-N-(3,4-methylenedioxybenzyl)benzamide

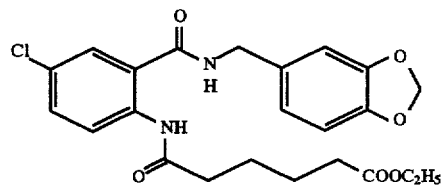

A white needle was obtained (yield: 54%).
M.P.: 154° to 158° C. (white needle from aq. EtOH)
NMR(400 MHz, δ, CDCl₃)
1.25(t, J=7.1 Hz, 3H), 1.67–1.81(m, 4H), 2.35(t, J=7.3 Hz, 2H), 2.43(t, J=7.0 Hz, 2H), 4.13(q, J=7.1 Hz, 2H), 4.50(d, J=5.7 Hz, 2H), 5.98(s, 2H), 6.52(t, J=5.7 Hz), 6.75–6.87(m, 3H), 7.37–7.42(m, 2H), 8.57(d, J=9.3 Hz, 1H), 10.96(s, 1H)

EXAMPLE 18

5-Chloro-2-[[4-(methoxycarbonyl)benzoyl]amino]-N-(3,4-methylenedioxybenzyl)benzamide

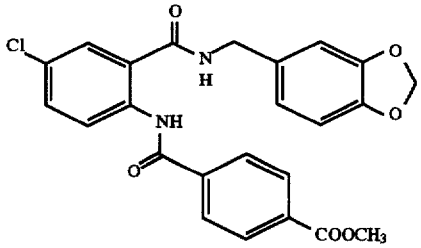

A slightly yellow powder was obtained (yield: 73%).
M.P.: 208° to 210° C. (white needle from aq. EtOH)
NMR(400 MHz, δ, DMSO-d$_6$)

3.90(s, 3H), 4.42(d, J=5.7 Hz, 2H), 5.98(s, 2H), 6.83(dd, J=1.5, 7.9 Hz, 1H), 6.86(dd, J=0.5, 7.9 Hz), 6.95(d, J=0.5 Hz, 1H), 7.66(dd, J=2.6, 9.0 Hz, 1H), 7.97(d, J=2.6 Hz, 1H), 7.99–8.05(m, 2H), 8.11–8.16(m, 2H), 8.61(d, J=9.0 Hz, 1H), 9.47(t, J=5.7 Hz), 12.50(s, 1H)

EXAMPLE 19

5-Chloro-2-[(cyclohexanecarbonyl)amino]-N-(3,4-methylenedioxybenzyl)benzamide

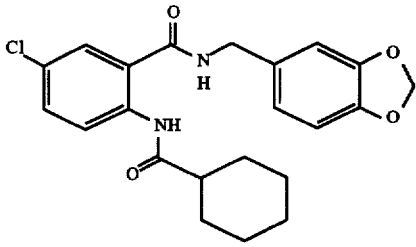

A white needle was obtained (yield: 44%).
M.P.: 141° to 142° C. (Et$_2$O)
MASS: (FAB)415(MH$^+$)
Elemental analysis:
calcd. C(%) H(%) N(%)
63.69 5.59 6.75
found C(%) H(%) N(%)
63.47 5.60 6.65
NMR(400 MHz, δ, CDCl$_3$)

1.18–1.39(m, 3H), 1.45–1.57(m, 2H), 1.70(m, 1H), 1.79–1.87(m, 2H), 1.95–2.03(m, 2H), 2.29(m, 1H), 4.51(d, J=5.5 Hz, 2H), 6.54(brt, 1H), 6.77–6.83(m, 2H), 6.84(m, 1H), 7.37(dd, J=2.2, 8.8 Hz, 1H), 7.40(d, J=2.2 Hz, 1H), 8.58(d, J=8.8 Hz, 1H), 10.91(s, 1H)

EXAMPLE 20

5-Chloro-2-[(1-methylpiperidine-4-carbonyl)-amino]-N-(3,4-methylenedioxybenzyl)benzamide

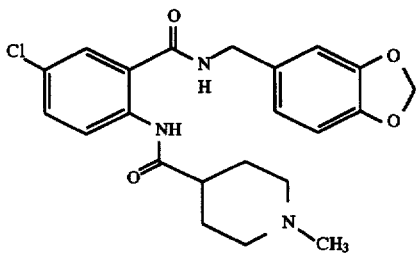

A slightly yellow needle was obtained (yield: 13%).
M.P.: 177° to 178° C. (EtOAc)
MASS (FAB)43((MH$^+$)
Elemental analysis:
calcd. C(%) H(%) N(%)
61.47 5.63 9.77
found C(%) H(%) N(%)
61.11 5.62 9.70
NMR(400 MHz, δ, CDCl$_3$)

1.80–1.92(m, 2H), 1.94–2.06(m, 4H), 2.70(m, 1H), 2.29(s, 3H), 2.88–2.98(m, 2H), 4.51(d, J=5.7 Hz, 2H), 5.98(s, 2H), 6.52(br, 1H), 6.77–6.86(m, 3H), 7.39(dd, J=2.4, 9.7 Hz, 1H), 7.40(d, J=2.4 Hz, 1H), 8.60(d, J=9.7 Hz, 1H), 11.05(s, 1H)

EXAMPLE 21

5-Dimethylaminomethyl-2-[[4-(methoxycarbonyl)benzoyl]amino]-N-(3,4-methylenedioxybenzyl)benzamide

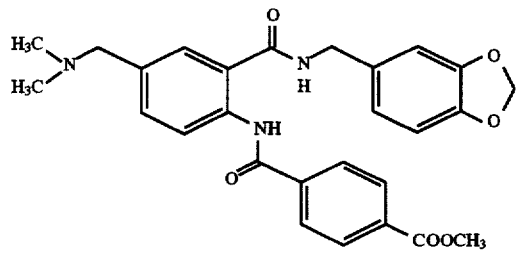

A white powder was obtained (yield: 50%).
M.P.: 171° to 174° C. (white needle from aq. EtOH)
NMR(400 MHz, δ, CDCl$_3$)

2.24(s, 6H), 3.40(s, 2H), 3.96(s, 3H), 4.54(d, J=5.7 Hz, 2H), 5.96(s, 2H), 6.79(d, J=7.9 Hz, 1H), 6.83(dd, J=1.5, 7.9 Hz, 1H), 6.87(d, J=1.5 Hz, 1H), 6.88(br, 1H), 7.42(dd, J=1.8, 8.4 Hz, 1H), 7.56(d, J=1.8 Hz, 1H), 8.08–8.13(m, 2H), 8.15–8.21(m, 2H), 8.76(d, J=8.4 Hz, 1H), 12.36(s, 1H)

EXAMPLE 22

5-Dimethylaminomethyl-2-[[trans-4-(ethoxycarbonyl)cyclohexanecarbonyl]amino]-N-(3,4-methylenedioxybenzyl)benzamide

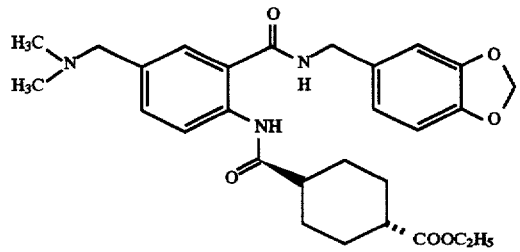

A white powder was obtained (yield: 32%).
M.P.: 144° to 145° C.
NMR(400 MHz, δ, CDCl$_3$)

1.25(t, J=7.1 Hz, 3H), 1.43–1.64(m, 4H), 2.05–2.13 (m, 4H), 2.20(s, 6H), 2.24–2.35(m, 2H), 3.35(s, 2H), 4.12 (q, J=7.1 Hz, 2H), 4.50(d, J=5.7 Hz, 2H), 5.95(s, 2H), 6.77(dd, J=0.5, 7.9 Hz, 1H), 6.80(dd, J=1.1, 7.9 Hz, 1H), 6.84(dd, J=0.5, 1.1 Hz), 6.86(t, J=5.7 Hz, 1H), 7.32(dd, J=1.8, 8.4 Hz, 1H), 7.48(d, J=1.8 Hz, 1H), 8.54(d, J=8.4 Hz, 1H), 11.18(s, 1H)

EXAMPLE 23

8-amino-5-bromoisoquinoline-1-one

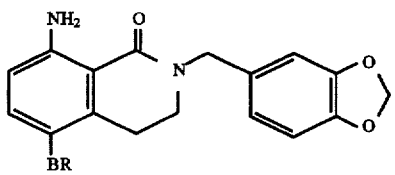

A white powder was obtained (yield: 82%).

M.P.: 153° to 155° C. (white needle from aq. EtOH)

NMR(400 MHz, δ, CDCl₃)

1.27(t, J=7.1 Hz, 3H), 1.41–1.62(m, 4H), 1.96–2.35(m, 6H), 2.88–3.08(br, 3H), 4.14(q, J=7.1 Hz, 2H), 4.45, 4.62(br, total 2H), 5.98(brs, 2H), 6.45–6.59, 6.71–6.93 (br, total 3H), 7.24(brm, 1H), 7.36(dd, J=2.4, 8.8 Hz, 1H), 8.13(d, J=8.8 Hz, 1H), 8.80–9.01(br, 1H)

EXAMPLE 24

5-Chloro-2-(4-hydroxypiperidino)acetamido-N-(3,4-methylenedioxybenzyl)benzamide

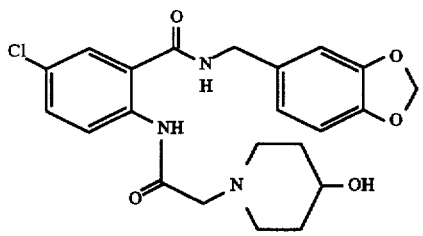

5-Chloro-2-chloroacetamido-N-(3,4-methylenedioxybenzyl)benzamide (570 mg) was dissolved in 5 ml of N,N-dimethylformamide, followed by the addition of 450 mg of 4-hydroxypiperidine, 620 mg of potassium carbonate and a catalytic amount of tetra(n-butyl) ammonium iodide. The obtained mixture was stirred at room temperature for one hour, followed by the addition of water. The resulting mixture was extracted with ethyl acetate. The organic phase was washed with water and a saturated aqueous solution of common salt, dried over anhydrous magnesium sulfate, and distilled to remove the solvent. The residue was purified by silica gel column chromatography (solvent: dichloromethane/methanol (30:1)) and recrystallized from ethyl acetate/n-hexane to give 560 mg of the title compound as a white powder (yield: 84%).

M.P.: 149° to 152° C. (ethyl acetate/n-hexane)

MASS: (FAB)446(MH⁺)

Elemental analysis:

calcd. C(%) H(%) N(%)

59.26 5.43 9.42 found C(%) H(%) N(%)

59.28 5.51 9.37

NMR(400 MHz, δ, DMSO-d₆)

1.55–1.65(m, 2H), 1.68–1.78(m, 2H), 2.19–2.28(m, 2H), 2.64–2.73 (m, 2H), 3.06 (s, 2H), 3.50 (m, 1H), 4.39(d, J=5.9 Hz, 2H), 4.58(d, J=3.7 Hz, 1H), 5.99(s, 2H), 6.83(dd, J=1.3, 8.1 Hz, 1H), 6.87(d, J=8.1 Hz, 1H), 6.92(d, J=1.3 Hz, 1H), 7.54(dd, J=2.6, 9.0 Hz, 1H), 7.73(d, 2.6 Hz, 1H), 8.52(d, J=9.0 Hz, 1H), 9.23(t, J=5.9 Hz, 1H), 11.69(s, 1H)

EXAMPLE 25

5-Chloro-N-(3,4-methylenedioxybenzyl)-2-(piperidinoacetamido)benzamide

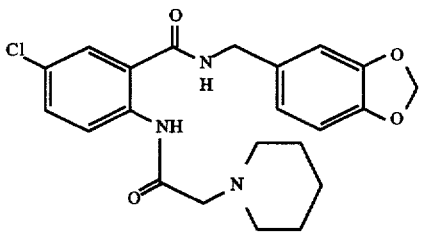

A white powder was obtained (yield: 45%).

M.P.: 155° to 156° C. (ethyl acetate/n-hexane)

MASS: (FAB)430(MH⁺)

Elemental analysis:

calcd. (C%) H(%) N(%)

61.47 5.63 9.77 found C(%) H(%) N(%)

61.38 5.61 9.75

NMR(400 MHz, δ, DMSO-d₆)

1.32–1.42(m, 2H), 1.52–1.51(m, 4H), 2.35–2.45(m, 4H), 3.03(s, 2H), 4.38(d, J=5.9 Hz, 2H), 5.98(s, 3H), 6.81 (dd, J=1.3, 7.9 Hz, 1H), 6.86(d, J=7.9 Hz, 1H), 6.92(d, J=1.3 Hz, 1H), 7.54(dd, J=2.6, 9.0 Hz, 1H), 7.74(d, J=2.6 Hz, 1H), 8.54(d, J=9.0 Hz, 1H), 9.25(t, J=5.9 Hz, 1H), 11.70(s, 1H)

EXAMPLE 26

5-Chloro-2-[4-(ethoxycarbonyl)piperidino]-acetamido-N-(3,4-methylenedioxybenzyl)benzamide

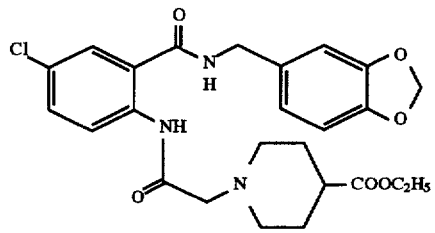

A white amorphous substance was obtained (yield: 99%).

NMR(400 MHz, δ, CDCl₃)

1.24(t, J=7.1 Hz, 3H), 1.90–1.98(m, 2H), 1.98–2.10(m, 2H), 2.26–2.36(m, 3H), 2.81–2.90(m, 2H), 3.10(s, 2H), 4.13(q, J=7.1 Hz, 2H), 4.50(d, J=5.9 Hz, 2H), 5.96(s, 2H), 6.71(t, J=5.9 Hz, 1H), 6.77(dd, J=0.4, 7.9 Hz, 1H), 6.81(dd, J=1.8, 7.9 Hz, 1H), 6.85(dd, J=0.4, 1.8 Hz, 1H), 7.30(dd, J=2.4, 9.0 Hz, 1H), 7.40(d, J=2.4 Hz, 1H), 8.49(d, J=9.0 Hz, 1H), 11.61(s, 1H)

EXAMPLE 27

5-Chloro-N-(3,4-methylenedioxybenzyl)-2-[(4-methylpiperazino)acetamido]benzamide

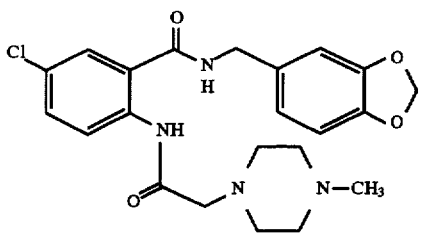

A white powder was obtained (yield: 70%).
M.P.: 162° to 164° C. (EtOAc/n-Hex)
MASS: (FAB)445(MH⁺)
Elemental analysis:

|  | C (%) | H (%) | N (%) |
|---|---|---|---|
| calcd. | 59.39 | 5.66 | 12.59 |
| found | 58.80 | 5.66 | 12.45 |

NMR(400 MHz, δ, CDCl$_3$)

2.35(s, 3H), 2.50–2.75(m, 8H), 3.17(s, 2H), 4.53(d, J=5.7 Hz, 2H), 5.97(s, 2H), 6.40(br, 1H), 6.77–6.82(m, 2H), 6.85(m, 1H), 7.39(dd, J=2.0, 8.8 Hz, 1H), 7.41(d, J=2.0 Hz, 1H), 8.57(d, J=8.8 Hz, 1H), 11.56 (br, 1H)

EXAMPLE 28

5-chloro-N-(3,4-methylenedioxybenzyl)-2-[(3-oxopiperazino)acetamido]benzamide

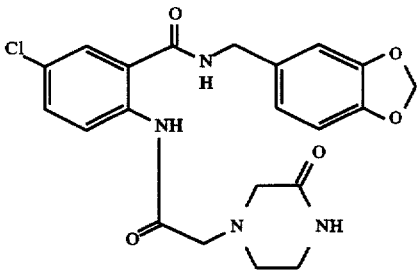

A white flake was obtained (yield: 52%).
M.P.: 202° to 203° C. (aq. EtOH)
MASS: (FAB)445(MH⁺)
Elemental analysis:

|  | C (%) | H (%) | N (%) |
|---|---|---|---|
| calcd. | 56.70 | 4.76 | 12.59 |
| found | 56.6580 | 4.78 | 12.56 |

NMR(400 MHz, δ, DMSO-d$_6$)

2.65(t, J=5.3 Hz, 2H), 3.10(s, 2H), 3.21(s, 2H), 3.23–3.30 (m, 2H), 4.36(d, J=5.7 Hz, 2H), 5.99(s, 2), 6.81(dd, J=1.6, 8.0 Hz, 1H), 6.88(d, J=8.0 Hz, 1H), 6.90(d, J=1.6 Hz, 1H), 7.56(dd, J=2.6, 9.0 Hz, 1H), 7.77(d, J=2.6 Hz, 1H), 7.83(brs, 1H), 8.52(d, J=9.0 Hz, 1H), 9.26(t, J=5.7 Hz, 1H) 11.72(s, 1H)

EXAMPLE 29

5-Chloro-2-[4-(ethoxycarbonyl)butylamino]-N-(3,4-methylenedioxybenzyl)benzamide

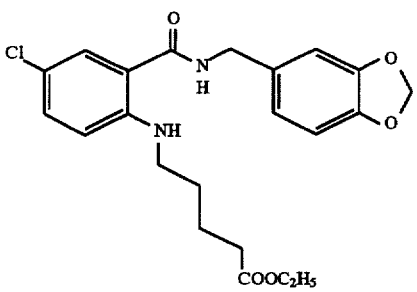

6-Chloro-1-[4-(ethoxycarbonyl)butyl]-1,2-dihydro-4H-1,3-benzoxazine-2,4-dione (3.50 g) was dissolved in 35 ml of N,N-dimethylformamide, followed by the addition of 0.13 g of 4-dimethylaminopyridine and 1.47 ml of 3,4-methylenedioxybenzylamine. The obtained mixture was stirred at room temperature for one hour, followed by the addition of ice-water. The resulting mixture was extracted with ethyl acetate. The organic phase was washed with 1N hydrochloric acid, a saturated aqueous solution of sodium hydrogen-carbonate, and a saturated aqueous solution of common salt successively, dried over anhydrous magnesium sulfate, and distilled to remove the solvent. The obtained solid was washed with ethanol to give 3.35 g of the title compound as a slightly yellow powder (yield: 72%).

M.P.: 89° to 91° C. (white needle from aq. EtOH)

NMR(400 MHz, δ, CDCl$_3$)

1.25(t, J=7.1 Hz, 3H), 1.65–1.80(m, 4H), 2.35(t, J=7.0 Hz, 2H), 3.13(m, 2H), 4.13(q, J=7.1 Hz, 2H), 4.46(d, J=5.7 Hz, 2H), 5.96(s, 2H), 6.26(brt, 1H), 6.60(d, J=9.0 Hz, 1H), 6.76–6.81(m, 2H), 6.83(m, 1H), 7.22(dd, J=2.4, 9.0 Hz, 1H), 7.26(d, J=2.4 Hz, 1H), 7.52(brt, 1H)

EXAMPLE 30

5-Chloro-2-[3-(thoxycarbonyl)propylamino]-N-(3,4-methylenedioxybenzyl)benzamide

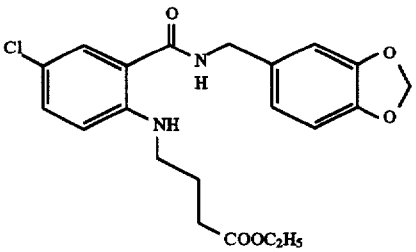

A pale-yellow solid was obtained (yield: 88%).

NMR(400 MHz, δ, CDCl$_3$)

1.26(t, J=7.1 Hz, 3H), 1.97(m, 2H), 2.42(t, J=7.3 Hz, 2H), 3.19(m, 2H), 4.14(q, J=7.1 Hz, 2H), 4.47(d, J=5.5 Hz, 2H), 5.96(s, 2H), 6.26(m, 1H), 6.64(d, J=8.8 Hz, 1H), 6.76–6.82(m, 2H), 6.83(m, 1H), 7.22(dd, J=2.4, 8.8 Hz, 1H), 7.27(d, J=2.4 Hz, 1H), 7.57(m, 1H)

EXAMPLE 31

5-Chloro-2-methylamino-N-(3,4-methylenedioxybenzyl) benzamide

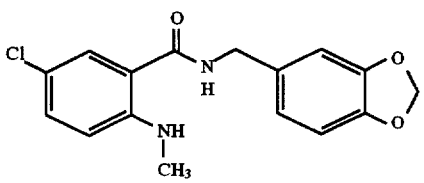

A slightly gray powder was obtained (yield: 94%).

M.P.: 152° to 154° C. (white needle from aq. EtOH)

NMR(400 MHz, δ, DMSO-$d_6$)

2.76(d, J=5.1 Hz, 3H), 4.31(d, J=5.9 Hz, 2H), 5.98(s, 2H), 6.64(d, J=9.0 Hz, 1H), 6.73(dd, J=1.5, 7.9 Hz, 1H), 6.85(d, J=7.9 Hz, 1H), 6.88(d, J=1.5 Hz, 1H), 7.31(dd, J=2.6, 9.0 Hz, 1H), 7.64(d, J=2.6 Hz, 1H), 7.74(q, J=5.1 Hz, 1H), 8.93(t, J=5.9 Hz, 1H)

EXAMPLE 32

5-Chloro-2-[4-(methoxycarbonyl)benzyl]-N-(3,4-methylenedioxybenzyl)benzamide

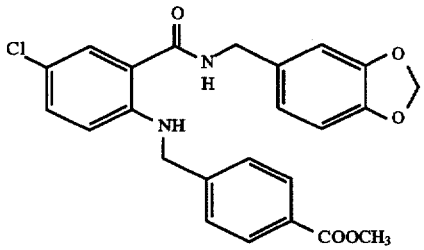

A slightly yellow powder was obtained (yield: 89%).

M.P.: 156° to 158° C. (white needle from aq. EtOH)

NMR(400 MHz, δ, CDCl$_3$)

3.91(s, 3H), 4.46(d, J=5.5 Hz, 2H), 4.50(d, J=5.5 Hz, 2H), 5.97(s, 2H), 6.29(brt, J=5 Hz, 1H, 6.46(d, J=9.0 Hz, 1H), 6.79(dd, J=0.7, 7.9 Hz, 1H), 6.82(dd, J=1.5, 7.9 Hz), 6.85(dd, J=0.7, 1.5 Hz), 7.14(dd, J=2.6, 9.0 Hz), 7.31(d, J=2.6 Hz, 1H), 7.38-7.43(m, 2H), 7.97-8.02(m, 2H), 8.16(brt, J=5 Hz, 1H)

EXAMPLE 33

5-Chloro-N-(3,4-methylenedioxybenzyl)-2-(4-picolyl) aminobenzamide

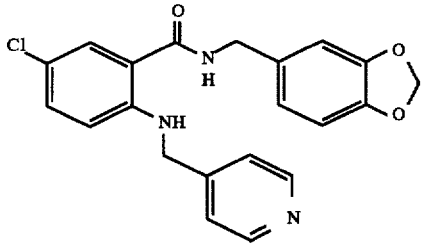

A suspension of 60% sodium hydride in mineral oil (1.34 g) was suspended in 50 ml of N,N-dimethyl-acetamide, followed by the addition of 3.0 g of 6-chloro-1,2-dihydro-4H-1,3-benzoxazine in portions. The obtained mixture was stirred at room temperature for one hour, followed by the addition of 4-picolyl chloride hydrochloride in portions. After 1.5 hours, the resulting mixture was heated to 50° C., stirred for 24 hours and cooled by allowing to stand. 3,4-Methylenedioxybenzylamine (2.1 ml) and 4-dimethylaminopyridine (0.19 g) were added to the mixture. The obtained mixture was stirred at room temperature for one hour, followed by the addition of ice-water. The resulting mixture was extracted with ethyl acetate. The organic phase was washed with water and a saturated aqueous solution of common salt, dried over anhydrous magnesium sulfate, and distilled to remove the solvent. The residue was purified by silica gel column chromatography (solvent: n-hexane/ethyl acetate (1:1 to 1:2)) and recrystallized from ethanol to give 870 mg of the title compound as a white needle (yield: 14%).

M.P.: 163° to 166° C.

MASS: (FAB)396(MH$^+$)

Elemental analysis:

|  | C (%) | H (%) | N (%) |
|---|---|---|---|
| calcd. | 63.72 | 4.58 | 10.62 |
| found | 63.79 | 4.57 | 10.62 |

NMR(400 MHz, δ, CDCl$_3$)

4.43(d, J=5.9 Hz, 2H), 4.51(d, J=5.7 Hz, 2H), 5.97(s, 2H), 6.40(m, 1H), 6.40(d, J=9.0 Hz, 1H), 6.79(dd, J=0.5, 7.9 Hz, 1H), 6.82(dd, J=1.5, 7.9 Hz, 1H), 6.85(dd, J=0.5, 1.5 Hz, 1H), 7.15(dd, J=2.4, 9.0 Hz, 1H), 7.24-7.27(m, 2H), 7.33(d, J=2.4 Hz, 1H), 8.21(t, J=5.9 Hz, 1H), 8.52-8.55(m, 2H)

EXAMPLE 34

5-Chloro-2-[[trans-4-(ethoxycarbonyl)cyclohexyl] methyl]amino-N-(3,4-methylenedioxybenzyl)benzamide

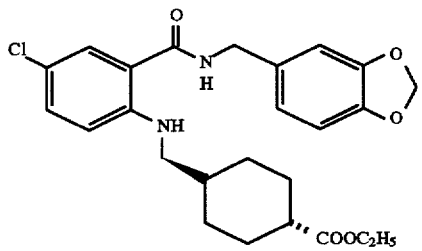

A pale-yellow powder was obtained (yield: 11%).

M.P.: 128° to 129° C.

(pale-yellow needle from aq. EtOH)

NMR(400 MHz, δ, CDCl$_3$)

0.9-1.11(m, 2H), 1.25(t, J=7.1 Hz, 3H), 1.38-1.51(m, 2H), 1.63(m, 1H), 1.90-1.99(m, 2H), 1.99-2.06(m, 2H), 2.25(m, 1H), 2.95-3.02(m, 2H), 4.12(q, J=7.1 Hz, 2H), 4.48(q, J=5.7 Hz, 2H), 5.96(s, 2H), 6.21(brt, 1H), 6.60(d, J=9.0 Hz, 1H), 6.76-6.82(m, 2H), 6.83(m, 1H), 7.21(dd, J=2.6, 9.0 Hz, 1H), 7.26(d, J=2.6 Hz, 1H), 7.65(br, t, 1H)

EXAMPLE 35

2-[(4-Carboxybutyryl)amino]-5-chloro-N-(3,4-methylenedioxybenzyl)benzamide

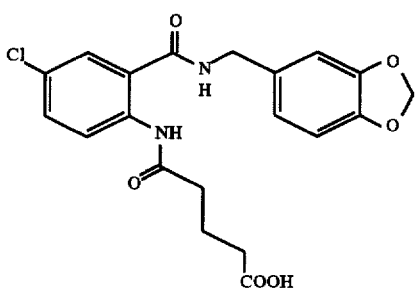

2-Amino-5-chloro-N-(3,4-methylenedioxybenzyl) benzamide (1.0 g) was dissolved in 10 ml of pyridine, followed by the addition of 0.41 g of glutaric anhydride. The obtained mixture was stirred at room temperature for 20 hours and concentrated, followed by the addition of ethyl acetate. The resulting mixture was extracted with 1N sodium hydroxide. The pH of the aqueous phase was adjusted to about 2. The precipitates formed were recovered by filtration and recrystallized from aqueous ethanol to give 500 mg of the title compound as a white powder (yield: 36%).

M.P.: 154° to 155° C. (aq. EtOH)

MASS: (FAB)419(NH⁺)

Elemental analysis:

|   | C (%) | H (%) | N (%) |
|---|---|---|---|
| calcd. | 57.35 | 4.57 | 6.69 |
| found | 57.17 | 4.56 | 6.64 |

NMR(400 MHz, δ, DMSO-d₆)

1.80(dt, J=7.3, 7.5 Hz, 2H), 2.28(t, J=7.3 Hz, 2H), 2.38(t, 7.5 Hz, 2H), 4.37(d, J=5.9 Hz, 2H), 5.99(s, 2H), 6.82(dd, J=1.6, 7.9 Hz, 1H), 6.87(dd, J=0.4, 7.9 Hz, 1H), 6.93(dd, J=0.4, 1.6 Hz, 1H), 7.55(dd, J=2.6, 9.0 Hz, 1H), 7.82(d, J=2.6 Hz, 1H), 8.38(d, J=9.0 Hz, 1H), 9.30(t, J=5.9 Hz, 1H), 11.17(s, 1H)

EXAMPLE 36

2-[(3-Carboxypropionyl)amino]-5-chloro-N-(3,4-methylenedioxybenzyl)benzamide

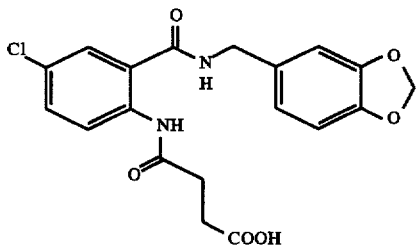

A white needle was obtained (yield: 38%).

M.P.: 217° to 220° C. (EtOH)

MASS: (FAB)405(MH⁺)

Elemental analysis:

|   | C (%) | H (%) | N (%) |
|---|---|---|---|
| calcd. | 56.37 | 4.23 | 6.92 |
| found | 56.24 | 4.25 | 6.88 |

NMR(400 MHz, δ, DMSO-d₆)

2.48–2.60(m, 4H), 4.38(d, J=5.9 Hz, 2H), 5.99(s, 2H), 6.82(ddd, J=0.4, 1.7, 7.9 Hz, 1H), 6.87(dd, J=1.7, 7.9 Hz, 1H), 6.93(dd, J=0.4, 1.7 Hz, 1H), 7.55(dd, J=2.4, 9.0 Hz, 1H), 7.83(d, J=2.4 Hz, 1H), 8.38(d, J=9.0 Hz, 1H), 9.31(t, J=5.9 Hz, 1H), 11.24(s, 1H)

EXAMPLE 37

2-[N-(4-Carboxybutyryl)-N-methyl]amino-5-chloro-N'-(3,4-methylenedioxybenzyl)benzamide

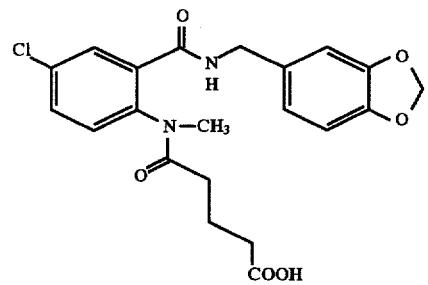

A white amorphous substance was obtained (yield: 39%).

MASS: (FAB)433(MH⁺)

NMR(400 MHz, δ, CDCl₃)

1.75–1.86(m, 2H), 1.99–2.48(m, 4H), 3.15, 3.22(s, total 3H), 4.41(dd, J=5.7, 14.5 Hz, 1H), 4.46(dd, J=5.7, 14.5 Hz, 1H), 5.94(s, 2H), 6.69, 7.04(m, total 1H), 6.73–6.82(m, 3H), 7.05, 7.12(d, J=8.4 Hz, total 1H), 7.40, 7.44(dd, J=2.4, 8.4 Hz, 1H), 7.47, 7.60(d, J=2.4 Hz, 1H)

EXAMPLE 38

1-[[4-Chloro-2-[(3,4-methylenedioxybenzyl)carbamoyl]phenyl]carbamoyl]piperidine-4-carboxylic acid

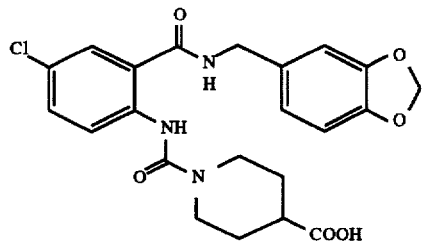

Ethanol (100 ml), tetrahydrofuran (100 ml) and 1N sodium hydroxide (65 ml) were added to 10.09 g of ethyl 1-[[4-chloro-2-[(3,4-methylenedioxybenzyl)carbamoyl]phenyl]carbamoyl]piperidine-4-carboxylate. The obtained mixture was stirred at room temperature for 2 hours, followed by the addition of 100 ml of water. The resulting mixture was concentrated, followed by the addition of water and ethyl acetate. The aqueous phase formed was recovered and the organic phase was extracted with 1N sodium hydroxide. The aqueous phase thus formed and the above aqueous phase were combined and adjusted to about pH 2 with concentrated hydrochloric acid. The precipitates formed were recovered by filtration and recrystallized from aqueous ethanol to give 6.84 g of the title compound as a white needle (yield: 72%).

M.P.: 263° to 264° C. (EtOH)

MASS: (FAB)460(MH⁺)

Elemental analysis:

|  | C (%) | H (%) | N (%) |
|---|---|---|---|
| calcd. | 57.46 | 4.82 | 9.14 |
| found | 57.39 | 4.73 | 9.09 |

NMR(400 MHz, δ, DMSO-$d_6$)

1.46(m, 2H), 1.86(m, 2H), 2.49(m, 1H), 2.98(m, 2H), 3.91(m, 2H), 4.38(d, J=5.7 Hz, 2H), 5.98(s, 2H), 6.81 (dd, J=1.5, 8.1 Hz, 1H), 6.86(d, J=8.1 Hz, 1H), 6.91(d, J=1.5 Hz, 1H), 7.49(dd, J=2.6, 9.0 Hz, 1H), 7.82(d, J=2.6 Hz, 1H), 8.31(d, J=9.0 Hz, 1H), 9.35(t, J=5.7 Hz), 11.06(s, 1H)

EXAMPLE 39

2-(trans-4-Carboxycyclohexanecarbonyl)amino-5-chloro-N-(3,4-methylenedioxybenzyl)benzamide

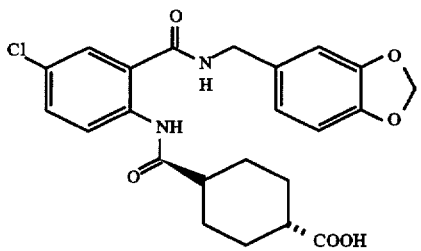

Ethanol (100 ml), tetrahydrofuran (100 ml) and 1N sodium hydroxide (65 ml) were added to 10.0 g of 5-chloro-2-[trans-4-(ethoxycarbonyl)cyclohexanecarbonyl]amino-N-(3,4-methylenedioxybenzyl)benzamide. The obtained mixture was stirred at room temperature for 8 hours and concentrated. The residue was dissolved in water and subjected to reversed phase silica gel chromatography (solvent: water to methanol containing 30% of water). The fractions were combined and concentrated to remove the methanol. The resulting solution was acidified with 1N hydrochloric acid. The precipitates formed were recovered by filtration and recrystallized from aqueous ethanol to give 7.10 g of the title compound as a white needle (yield: 75%).

M.P.: 228° to 230° C. (EtOH)

MASS: (FAB)459(MH⁺)

Elemental analysis:

|  | C (%) | H (%) | N (%) |
|---|---|---|---|
| calcd. | 60.20 | 5.05 | 6.10 |
| found | 59.95 | 5.11 | 6.08 |

NMR(400 MHz, δ, DMSO-$d_6$)

1.31–1.48(m, 4H), 1.87–2.03(m, 4H), 2.13–2.29(m, 2H), 4.38(d, J=5.7 Hz, 2H), 5.99(s, 2H), 6.82(dd, J=1.6, 7.9 Hz, 1H), 6.87(d, J=7.9 Hz, 1H), 6.93(d, J=1.6 Hz, 1H), 7.54(dd, J=2.6, 9.0 Hz, 1H), 7.83(d, J=2.6 Hz, 1H), 8.40(d, J=9.0 Hz,1H), 9.32(t, J=5.7 Hz, 1H), 11.19(s, 1H)

EXAMPLE 40

2-(5-Carboxyvaleryl)amino-5-chloro-N-(3,4-methylenedioxybenzyl)benzamide

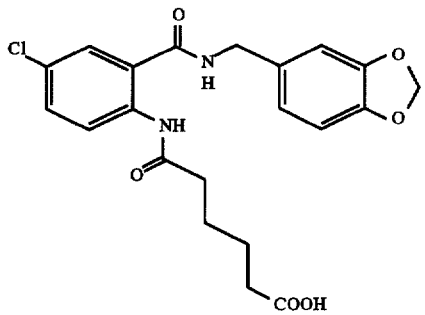

A white needle was obtained (yield: 30%).

M.P.: 197° to 199° C. (EtOH)

MASS: (FAB)433(MH⁺)

Elemental analysis:

|  | C (%) | H (%) | N (%) |
|---|---|---|---|
| calcd. | 58.27 | 4.89 | 6.47 |
| found | 58.03 | 4.96 | 6.38 |

NMR(400 MHz, δ, DMSO-$d_6$)

1.49–1.63(m, 4H), 2.23(t, J=7.3 Hz, 2H), 2.34(t, J=6.8 Hz, 2H), 4.37(d, 5.7 Hz, 2H), 5.99(s, 2H), 6.82(dd, J=1.6, 7.9 Hz, 1H), 6.87(dd, J=0.4, 7.9 Hz, 1H), 6.93(dd, J=0.4, 1.6 Hz, 1H), 7.55(dd, J=2.6, 9.0 Hz, 1H), 7.82(d, J=2.6 Hz, 1H), 8.39(d, J=9.0 Hz, 1H), 9.30(t, J=5.7 Hz, 1H), 11.15(s, 1H)

EXAMPLE 41

2-(4-Carboxybenzoyl)amino-5-chloro-N-(3,4-methylenedioxybenzyl)benzamide

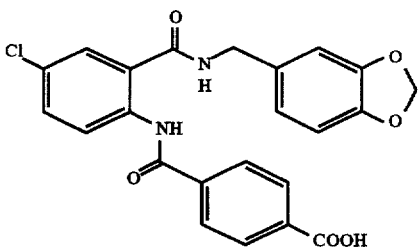

A white needle was obtained (yield: 74%).

M.P.: 260° to 262° C. (aq. EtOH)

MASS: (FAB)453(MH⁺)

Elemental analysis:

|  | C (%) | H (%) | N (%) |
|---|---|---|---|
| calcd. | 61.00 | 3.78 | 6.19 |
| found | 60.83 | 3.98 | 6.09 |

NMR(400 MHz, δ, DMSO-$d_6$)

4.42(d, J=5.7 Hz, 2H), 5.98(s, 2H), 6.83(dd, J=1.5, 7.9 Hz, 1H), 6.86(dd, J=0.5, 7.9 Hz, 1H), 6.95(dd, J=0.5, 1.5

Hz, 1H), 7.66(dd, J=2.4, 9.0 Hz, 1H), 7.97(d, J=2.4 Hz, 1H), 7.98–8.03(m, 2H), 8.09–8.15(m, 2H), 8.62(d, J=9.0 Hz, 1H), 9.47(t, J=5.7 Hz, 1H), 12.50(s, 1H)

EXAMPLE 42

1-[[4-chloro-2-[[(2,3-dihydrobenzofuran-5-yl)methyl]carbamoyl]phenyl]carbamoyl]piperidine-4-carboxylic acid

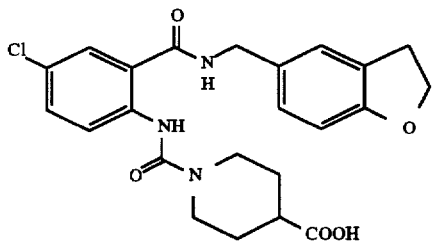

A white needle was obtained (yield: 26%).
M.P.: 258° to 259° C. (aq. EtOH)
MASS: (FAB)458(MH$^+$)
Elemental analysis:

|  | C (%) | H (%) | N (%) |
|---|---|---|---|
| calcd. | 60.33 | 5.28 | 9.18 |
| found | 60.18 | 5.25 | 9.16 |

NMR(400 MHz, δ, DMSO-d$_6$)
1.47(m, 2H), 1.86(m, 2H), 2.47(m, 1H), 2.99(m, 2H), 3.15(t, J=8.8 Hz, 2H), 3.91(m, 2H), 4.38(d, J=5.9 Hz, 2H), 4.50(t, J=8.8 Hz, 2H), 6.70(d, J=8.2 Hz, 1H), 7.05(dd, J=1.8, 8.2 Hz, 1H), 7.20(d, J=1.8 Hz, 1H), 7.48(dd, J=2.6, 9.2 Hz, 1H), 7.82(d, J=2.6 Hz, 1H), 8.32(d, J=9.2 Hz, 1H), 9.34(t, J=5.9 Hz, 1H), 11.12(s, 1H)

EXAMPLE 43

1-[[4-Chloro-2-(3-chloro-4-methoxybenzyl)carbamoyl]phenyl]carbamoyl]piperidine-4-carboxylic acid

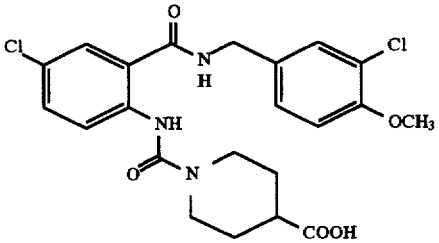

A white needle was obtained (yield: 63%).
M.P.: 288° to 291° C. (aq. EtOH)
MASS: (FAB)480(MH$^+$)
Elemental analysis:

|  | C (%) | H (%) | N (%) |
|---|---|---|---|
| calcd. | 55.01 | 4.83 | 8.75 |
| found | 54.80 | 4.81 | 8.64 |

NMR(400 MHz, δ, DMSO-d$_6$)
1.47(m, 2H), 1.86(m, 2H), 2.46(m, 1H), 2.99(m, 2H), 3.83(s, 3H), 3.91(m, 2H), 4.40(d, J=5.7 Hz, 2H), 7.11 (d, J=8.6 Hz, 1H), 7.28(dd, J=2.0, 8.6 Hz, 1H), 7.40(d, J=2.0 Hz, 1H), 7.49(dd, J=2.6, 9.0 Hz, 1H), 7.82(d, J=2.6 Hz, 1H), 8.31(d, J=9.0 Hz, 1H), 9.37(t, J=5.7 Hz), 11.02(s, 1H)

EXAMPLE 44

2-(3-Carboxyacryoyl)amino-5-chloro-N-(3,4-methylenedioxybenzyl)benzamide

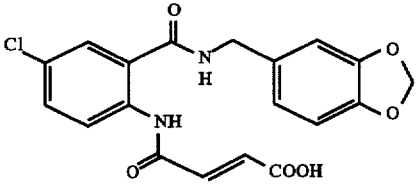

A white needle was obtained (yield: 9%)
M.P.: 256° to 258° C. (dec.) (ethanol)
MASS: (FAB)403(MH$^+$)
Elemental analysis:

|  | C (%) | H (%) | N (%) |
|---|---|---|---|
| calcd. | 56.66 | 3.75 | 6.95 |
| found | 56.17 | 3.68 | 6.75 |

NMR(400 MHz, δ, DMSO-d$_6$)
4.38(d, J=5.7 Hz, 2H), 5.98(s, 2H), 6.64(d, J=15.4 Hz, 1H), 6.82(dd, J=1.5, 7.9 Hz, 1H), 6.86(d, J=7.9 Hz, 1H), 6.93(d, J=1.5 Hz, 1H), 7.00(d, J=15.4 Hz, 1H), 7.60(dd, J=2.4, 8.8 Hz, 1H), 7.83(d, J=2.4 Hz, 1H), 8.29(d, J=8.8 Hz, 1H), 9.29(t, J=5.7 Hz, 1H), 11.49(s, 1H)

EXAMPLE 45

5-Bromo-2-(trans-4-carboxycyclohexanecarbonyl)amino-N-(3,4-methylenedioxybenzyl)benzamide

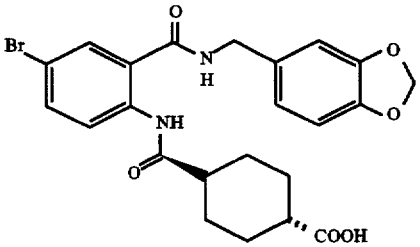

A white needle was obtained (yield: 74%).
M.P.: 236° to 238° C. (white needle from aq. EtOH)
NMR(400 MHz, δ, DMSO-d$_6$)
1.31–1.47(m, 4H), 1.85–2.03(m, 4H), 2.14–2.30(m, 2H), 4.38(d, J=5.9 Hz, 2H), 5.99(s, 2H), 6.81(dd, J=1.5, 7.9 Hz, 1H), 6.87(d, J=7.9 Hz, 1H), 6.93(d, J=1.5 Hz, 1H), 7.67(dd, J=2.4, 9.0 Hz, 1H), 7.94(d, J=2.4 Hz, 1H), 8.35(d, J=9.0 Hz, 1H), 9.33(t, J=5.9 Hz, 1H), 11.20(s, 1H), 12.09(br, 1H)

EXAMPLE 46

2-(trans-4-Carboxycyclohexanecarbonyl)amino-5-chloro-N-methyl-N-(3,4-methylenedioxybenzyl)benzamide

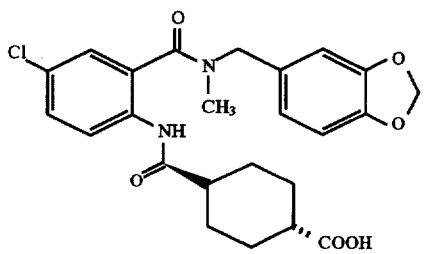

A white prism was obtained (yield: 78%).

M.P.: 202° to 204° C. (white prism from aq. EtOH)

NMR(400 MHz, δ, DMSO-d₆)

1.24–1.50(m, 4H), 1.66–2.01(m, 4H), 2.10–2.42(m, 2H), 2.67, 2.83(s, total 3H), 4.22, 4.51(s, total 2H), 6.00, 6.01(s, total 2H), 6.62–6.67, 6.80–6.89(m, total 2H), 6.77, 7.02(s, total 1H), 7.35–7.57(m, 3H), 9.57, 9.62(s, total 1H), 12.08(br, 1H)

EXAMPLE 47

Sodium trans-4-[4-chloro-2-(3,4-methylenedioxybenzyl)carbamoyl]phenyl]aminomethylcyclohexanecarboxylate

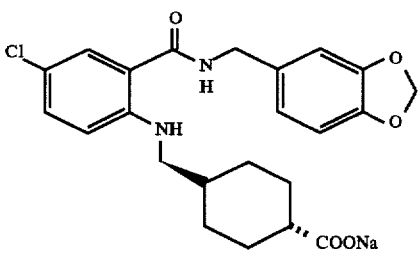

Ethanol (7 ml), tetrahydrofuran (7 ml) and 1N sodium hydroxide (7 ml) were added to 800 mg of 5-chloro-2-[[trans-4-(ethoxycarbonyl)cyclohexyl]-methyl]amino-N-(3,4-methylenedioxybenzyl)benzamide. The obtained mixture was stirred at room temperature for 17 hours.

The reaction mixture was concentrated and purified by reversed phase silica gel column chromatography (solvent: water to 40% methanol). The fractions were combined and concentrated to dryness. The solid was washed with 2-propanol to give 780 mg of the title compound as a slightly yellow powder (yield: 98%).

M.P.: 266° to 271° C. (dec.)

MASS: (FAB)489((M+Na)⁺), 467(MH⁺)

NMR(400 MHz, δ, DMSO-d₆)

0.85–1.00(m, 2H), 1.13–1.28(m, 2H), 1.44(m, 1H), 1.69–1.80(m, 2H), 1.80–1.92(m, 2H), 2.85–2.97(m, 2H), 4.32(d, J=5.5 Hz, 2H), 5.98(s, 2H), 6.67(d, J=9.3 Hz, 1H), 6.78(dd, J=1.5, 7.8 Hz, 1H), 6.85(d, J=7.8 Hz, 1H), 6.88(d, J=1.5 Hz, 1H), 7.26(dd, J=2.4, 9.3 Hz, 1H), 7.66(d, J=2.4 Hz, 1H), 7.97(t, J=5.5 Hz, 1H), 9.03(t, J=5.7 Hz, 1H)

EXAMPLE 48

Sodium 4-[[4-chloro-2-(3,4-methylenedioxybenzyl)carbamoyl]phenyl]aminomethylbenzoate

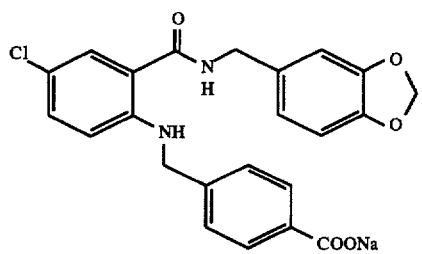

A slightly yellow powder was obtained (yield: 88%).

M.P: >300° C.

MASS: (FAB)461(MH⁺), 483((M+Na)⁺)

NMR(400 MHz, δ, DMSO-d₆)

4.33(d, J=5.7 Hz, 2H), 4.36(d, J=5.5 Hz, 2H), 5.99(s, 2H), 6.63(d, J=9.0 Hz, 1H), 6.80(dd, J=1.5, 7.9 Hz, 1H), 6.88(d, J=7.9 Hz, 1H), 6.90(d, J=1.5 Hz, 1H), 7.20(d, J=8.1 Hz, 2H), 7.23(dd, J=2.6, 8.1 Hz, 1H), 7.67(d, J=2.6 Hz, 1H), 7.81(d, J=8.1 Hz, 2H), 8.29(t, J=5.7 Hz, 1H), 9.03(t, J=5.5 Hz, 1H)

EXAMPLE 49

Sodium 4-[[4-chloro-2-(3,4-methylenedioxybenzyl)carbamoyl]phenyl]aminobutyrate

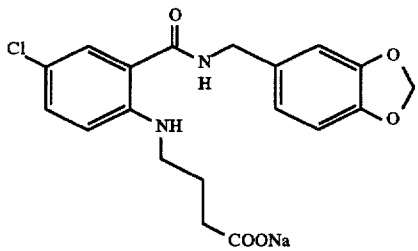

A slightly yellow powder was obtained (yield: 35%).

MASS: (FAB)435(MH+Na⁺)

NMR(400 MHz, δ, DMSO-d₆)

1.71(m, 2H), 1.98(m, 2H), 3.06(m, 2H), 4.32(d, J=4.4 Hz, 2H), 5.98(s, 2H), 6.72(d, J=9.0 Hz, 1H), 6.79(dd, J=1.1, 7.9 Hz, 1H), 6.85(d, J=7.9 Hz, 1H), 6.89(d, J=1.1 Hz, 1H), 7.25(dd, J=2.4, 9.0 Hz, 1H), 7.64(d, J=2.4 Hz, 1H), 7.86(t, J=4.4 Hz, 1H), 9.00(t, J=5.5 Hz)

EXAMPLE 50

Sodium 5-[[4-chloro-2-(3,4-methylenedioxybenzyl)carbamoyl]phenyl]aminovalerate

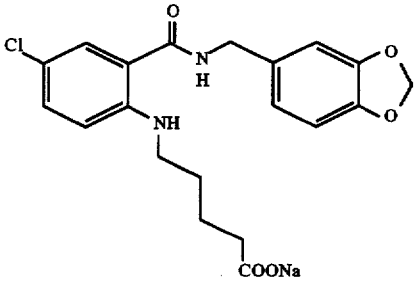

A slightly yellow powder was obtained (yield: 41%).

MASS: (FAB)449((M+Na]⁺)

NMR(400 MHz, δ, DMSO-d₆)

1.48–1.60(m, 4H), 1.88–1.98(m, 2H), 2.99–3.08(m, 2H), 4.32(d, J=5.3 Hz, 2H), 5.97(s, 2H), 6.66(d, J=9.0 Hz, 1H), 6.79(dd, J=1.5, 7.9 Hz, 1H), 6.85(d, J=7.9 Hz), 6.89(d, J=1.5 Hz, 1H), 7.27(dd, J=2.4, 9.0 Hz), 7.67(d, J=2.4 Hz, 1H), 7.87(t, J=5.3 Hz, 1H), 9.04(t, J=8.3 Hz, 1H)

EXAMPLE 51

Sodium 1-[[[4-chloro-2-(3,4-methylenedioxybenzyl) carbamoyl]phenyl]carbamoylmethyl]piperidine-4-carboxylate

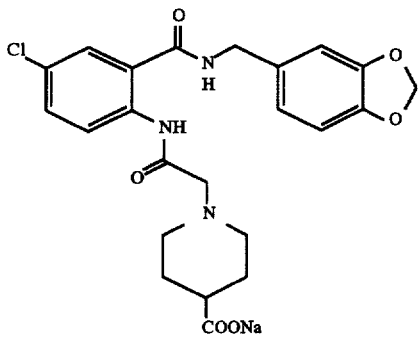

A white powder was obtained (yield: 76%).

M.P.: 244° to 249° C. (dec.)

MASS: (FAB)518((M+Na)⁺), 496(MH⁺)

NMR(400 MHz, δ, DMSO-d₆)

1.68–1.85(m, 4H), 2.05–2.16(m, 2H), 2.67–2.77(m, 2H), 3.01(s, 2H), 3.42(br, 1H), 4.38(br, s, 2H), 5.98(s, 2H), 6.85(dd, J=1.3, 8.1 Hz, 1H), 6.87(dd, J=0.7, 8.1 Hz, 1H), 6.93(d, J=0.7 Hz, 1H), 7.52(dd, J=2.6, 9.0 Hz, 1H), 7.74(d, J=2.6 Hz, 1H), 8.48(d, J=9.0 Hz, 1H), 9.38 (br, 1H), 11.59 (br, 1H)

EXAMPLE 52

Sodium 4-[[[4-dimethylaminomethyl-2-(3,4-methylenedioxybenzyl)carbamoyl]phenyl]carbamoyl]benzoate

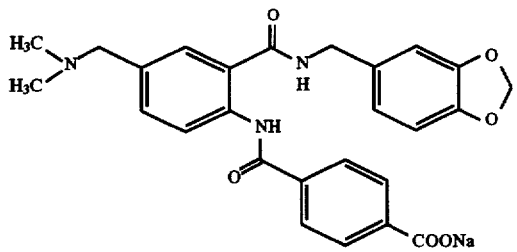

A white powder was obtained (yield: 48%).

M.P.: 280° C. (dec.)

NMR(400 MHz, δ, DMSO-d₆)

2.16(s, 6H), 3.38(s, 2H), 4.33(d, J=4.9 Hz, 2H), 5.98(s, 2H), 6.82–6.88(m, 2H), 6.95(s, 1H), 7.48(dd, J=0.5, 8.4 Hz, 1H), 7.92(d, J=0.5 Hz, 1H), 7.82(d, J=8.1 Hz, 2H), 7.99(d, J=8.1 Hz, 1H), 8.59(d, J=8.4 Hz, 1H), 9.45(br, 1H), 12.42(s, 1H)

EXAMPLE 53

2-Amino-5-bromo-4-methoxy-N-(3,4-methylenedioxybenzyl)benzamide

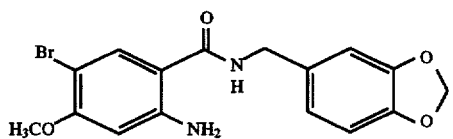

2-Amino-5-bromo-4-methoxybenzoic acid (1.50 g), piperonylamine (0.84 ml), 1-(3-dimethylaminopropyl)-3-ethylcarbodiimide hydrochloride (1.29 g), 1-hydroxybenztriazole (0.91 g) and triethylamine (0.93 ml) were added to 20 ml of N,N-dimethylformamide. The obtained mixture was stirred at room temperature for 20 hours, followed by the addition of water. The precipitates formed were recovered by filtration to give 2.19 g of the title compound as a slightly orange powder (yield: 100%).

M.P.: 143° to 144° C.

MASS: 378(M⁺)

¹H-NMR(400 MHz, CDCl₃) δ:

3.85(3H, s), 4.46(2H, d, J=5.7 Hz), 5.81(2H, s), 5.95(2H, s), 6.15(1H, s), 6.15(1H, m), 6.77(1H, dd, J=7.9, 0.5 Hz), 6.79(1H, dd, J=7.9, 2.2 Hz), 6.83(1H, dd, J=2.2, 0.5 Hz), 7.44(1H, s)

EXAMPLE 54

2-Amino-5-bromo-N-(3-chloro-4-methoxybenzyl)-4-methoxybenzamide

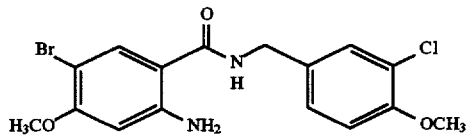

The title compound was obtained as a slightly orange powder in a similar manner to that of Example 53 (yield: 100%).

M.P.: 146° to 148° C.

MASS: 400(M⁺)

¹H-NMR(400 MHz, CDCl₃) δ:

3.85(3H, s), 3.89(3H, s), 4.47(2H, d, J=5.7 Hz), 5.81(2H, s), 6.15(1H, s), 6.23(1H, t, J=5.7 Hz), 6.89(1H, d, J=8.4 Hz), 7.19(1H, dd, J=8.4, 2.2 Hz), 7.34(1H, d, J=2.2 Hz), 7.45(1H, s)

EXAMPLE 55

2-Amino-5-chloro-N-(3-chloro-4-methoxybenzyl)benzamide

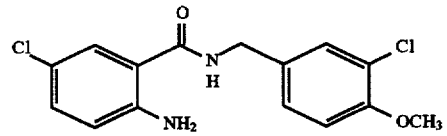

The title compound was obtained as a slightly ocherous powder in a similar manner to that of Example 53 (yield: 93%).

M.P.: 176° to 178° C.

MASS: 324(M⁺)

¹H-NMR(400 MHz, CDCl₃) δ:

3.90(3H, s), 4.50(2H, d, J=5.7 Hz), 5.54(2H, s), 6.28(1H, s), 6.63(1H, d, J=8.8 Hz), 6.90(1H, d, J=8.4 Hz), 7.15(1H, dd, J=8.4, 2.4 Hz), 7.21(1H, dd, J=8.4, 2.2 Hz), 7.27(1H, d, J=2.4 Hz), 7.36(1H, d, J=2.2 Hz)

EXAMPLE 56

2-Amino-5-chloro-N-[(2-methoxy-5-pyridyl)methyl]benzamide

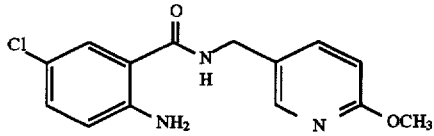

The title compound was obtained as a white powder in a similar manner to that of Example 53 (yield: 73%).
M.P.: 156° to 159° C.
MASS: 292(MH$^+$)
$^1$H-NMR(400 MHz, CDCl$_3$) δ:
3.94(3H, s), 4.52(2H, d, J=5.7 Hz), 5.54(2H, s), 6.22(1H, s), 6.63(1H, d, J=8.8 Hz), 6.75(1H, d, J=8.4 Hz), 7.15(1H, dd, J=8.8, 2.4 Hz), 7.25(1H, dd, J=2.4 Hz), 7.60(1H, dd, J=8.4, 2.6 Hz), 8.14(1H, d, J=2.6 Hz)

EXAMPLE 57

2-Amino-N-(3,4-methylenedioxybenzyl)-5-trifluoromethoxybenzamide

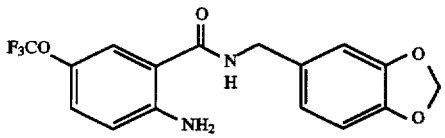

The title compound was obtained as a slightly yellow powder in a similar manner to that of Example 53 (yield: 100%).
M.P.: 150° to 153° C.
MASS: 354(M$^+$)
$^1$H-NMR(400 MHz, CDCl$_3$) δ:
4.50(2H, d, J=5.7 Hz), 5.59(2H, s), 5.96(2H, s), 6.19(1H, s), 6.66(1H, d, J=8.8 Hz), 6.78(1H, dd, J=7.9, 0.5 Hz), 6.81(1H, dd, J=7.9, 1.5 Hz), 6.85(1H, dd, J=1.5, 0.5 Hz), 7.09(1H, m), 7.14(1H, d, J=2.6 Hz)

EXAMPLE 58

2-Amino-5-chloro-N-(3-cyano-4-methoxybenzyl)benzamide

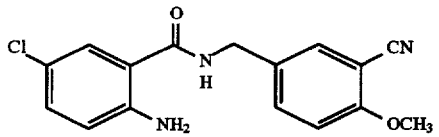

The title compound was obtained as a white powder in a similar manner to that of Example 53 (yield: 100%).
M.P.: 174° to 177° C.
MASS: 315(M$^+$)
$^1$H-NMR(400 MHz, CDCl$_3$) δ:
3.89(3H, s), 4.36(2H, d, J=5.7 Hz), 6.59(2H, s, 6.73(1H, d, J=8.8 Hz), 7.17(1H, dd, J=8.8, 2.6 Hz), 7.22(1H, d, J=8.6 Hz), 7.58–7.66(3H, m), 8.89(1H, t, J=5.7 Hz)

EXAMPLE 59

2-Amino-5-bromo-N-(3-chloro-4-methoxybenzyl)benzamide

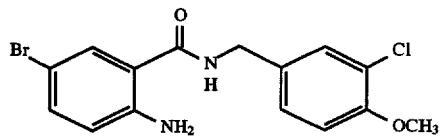

The title compound was obtained as a slightly orange powder in a similar manner to that of Example 53 (yield: 98%).
M.P.: 168° to 170° C.
MASS: 370(M$^+$)
$^1$H-NMR(400 MHz, CDCl$_3$) δ:
3.90(3H, s), 4.49(2H, d, J=5.7 Hz), 5.56(2H, s), 6.30(1H, s), 6.58(1H, d, J=8.8 Hz), 6.90(1H, d, J=8.4 Hz), 7.20(1H, dd, J=8.4, 2.2 Hz), 7.27(1H, dd, J=8.8, 2.2 Hz), 7.35(1H, d, J=2.2 Hz), 7.40(1H, d, J=2.2 Hz)

EXAMPLE 60

2-Amino-5-chloro-N-(4-chloro-3-methoxybenzyl)benzamide

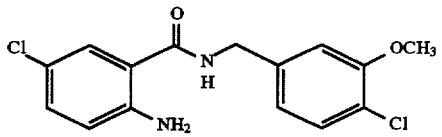

The title compound was obtained as a slightly ocherous powder in a similar manner to that of Example 53 (yield: 99%).
M.P.: 162° to 163° C.
MASS: 324 (M$^+$)
$^1$H-NMR(400 MHz, CDCl$_3$) δ:
3.91(3H, s), 4.55(2H, d, J=5.7 Hz), 5.54(2H, s), 6.31(1H, s), 6.46(1H, d, J=8.8 Hz), 6.87(1H, dd, J=8.1, 1.8 Hz), 6.92(1H, d, J=1.8 Hz), 7.16(1H, dd, J=8.8, 2.4 Hz), 7.28(1H, d, J=2.4 Hz), 7.34(1H, d, J=8.1 Hz)

EXAMPLE 61

2-Amino-5-cyano-N-(3,4-methylenedioxybenzyl)benzamide

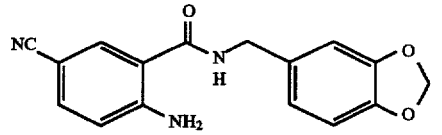

The title compound was obtained as a slightly yellow powder in a similar manner to that of Example 1 (yield: 88%).
M.P.: 163° to 166° C.
MASS: 295(M$^+$)
$^1$H-NMR(400 MHz, CDCl$_3$) δ:
4.49(2H, d, J=5.5 Hz), 5.96(2H, s), 6.22(1H, s), 6.40(1H, m), 6.63(1H, d, J=8.6 Hz), 6.79(1H, d, J=8.1 Hz), 6.81(1H, dd, J=8.1, 1.3 Hz), 6.84(1H, d, J=1.3 Hz), 7.40(1H, dd, J=8.1, 1.8 Hz), 7.65(1H, d, J=1.8 Hz)

EXAMPLE 62

2-Amino-N-(3-chloro-4-methoxybenzyl)-5-cyanobenzamide

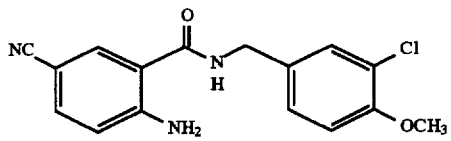

The title compound was obtained as a pale-yellow powder in a similar manner to that of Example 53 (yield: 100%).
M.P.: 184° to 186° C.
MASS: 316(MH$^+$)
$^1$H-NMR(400 MHz, CDCl$_3$) δ:
3.90(3H, s), 4.50(2H, d, J=5.7 Hz), 6.23(2H, s), 6.47(1H, m), 6.67(1H, d, J=8.6 Hz), 6.92(1H, d, J=8.4 Hz), 7.22(1H, dd, J=8.4, 2.2 Hz), 7.37(1H, d, J=2.2 Hz), 7.41(1H, dd, J=8.6, 2.0 Hz), 7.67(1H, d, J=2.0 Hz)

EXAMPLE 63

2-Amino-N-(3-chloro-4-methoxybenzyl)-5-nitrobenzamide

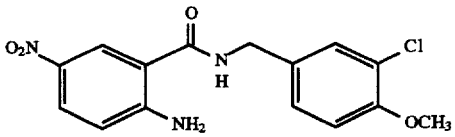

The title compound was obtained as a yellow powder in a similar manner to that of Example 53 (yield: 79%).
M.P.: 194° to 198° C.
MASS: 336 (M$^+$)
$^1$H-NMR(400 MHz, CDCl$_3$) δ:
3.90(3H, s), 4.53(2H, d, J=5.7 Hz), 6.50–6.64(3H, m), 6.66(1H, d, J=9.2 Hz), 6.91(1H, d, J=8.4 Hz), 7.23(1H, dd, J=8.4, 2.2 Hz), 7.38(1H, d, J=2.6 Hz), 8.08(1H, dd, J=9.2, 2.6 Hz), 8.34(1H, d, J=2.4 Hz)

EXAMPLE 64

2-Amino-N-(3-chloro-4-methoxybenzyl)-5-dimethylsulfamoylbenzamide

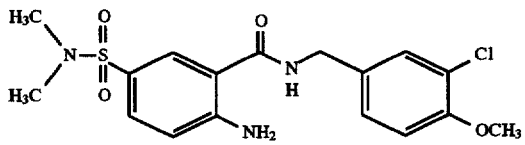

The title compound was obtained as a slightly yellow powder in a similar manner to that of Example 53 (yield: 93%).
M.P.: 195° to 199° C.
MASS: 398(MH$^+$)
$^1$H-NMR(400 MHz, CDCl$_3$) δ:
2.66(6H, s), 3.89(3H, s), 4.51(2H, d, J=5.9 Hz), 6.26(2H, s), 6.72(1H, d, J=8.8 Hz), 6.89(1H, d, J=8.4 Hz), 6.89(1H, t, J=5.9 Hz), 7.24(1H, dd, J=8.4, 2.2 Hz), 7.39(1H, d, J=2.2 Hz), 7.54(1H, dd, J=8.8, 2.0 Hz), 7.84(1H, d, J=2.0 Hz)

EXAMPLE 65

2-Amino-N-(3-chloro-4-methoxybenzyl)-5-methylsulfamoylbenzamide

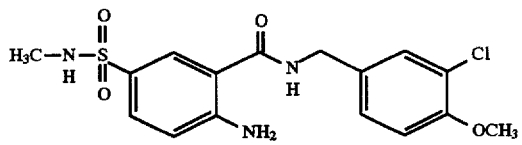

The title compound was obtained as a slightly yellow powder in a similar manner to that of Example 53 (yield: 78%).
M.P.: 154° to 155° C.
MASS: 873(M$^+$)
$^1$H-NMR(400 MHz, CDCl$_3$) δ:
2.57(3H, d, J=5.5 Hz), 3.87(3H, s), 4.47(2H, d, J=5.9 Hz), 4.66(1H, q, J=5.5 Hz), 6.26(2H, s), 6.68(1H, d, J=8.6 Hz), 6.86(1H, d, J=8.6 Hz), 7.01(1H, t, J=5.9 Hz), 7.20(1H, dd, J=8.6, 2.2 Hz), 7.36(1H, d, J=2.2 Hz), 7.57(1H, dd, J=8.6, 2.2 Hz), 7.93(1H, d, J=2.2 Hz)

EXAMPLE 66

2-Amino-N-(3,4-methylenedioxybenzyl)-5-(1-pyrazolyl)benzamide

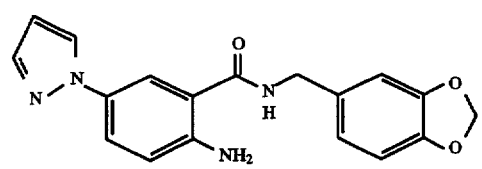

N-(3,4-Methylenedioxybenzyl)-2-nitro-5-(1-pyrazolyl)benzamide (1.80 g) was dissolved in 120 ml of tetrahydrofuran, followed by the addition of 1.8 g of 10% palladium/carbon (water-containing one). The obtained mixture was subjected to catalytic reduction under the conditions of room temperature and one atm. After 13 hours, the reaction mixture was freed from the catalyst by filtration and concentrated in a vacuum. Ether was added to the obtained residue to conduct crystallization. The formed crystals were recovered by filtration to give 1.50 g of the title compound as a white powder (yield: 91%).
M.P.: 146° to 147° C.
MASS: 336(M$^+$)
$^1$H-NMR(400 MHz, CDCl$_3$) δ:
4.50(2H, d, J=5.7 Hz), 5.65(2H, s), 5.95(2H, s), 6.42(1H, dd, J=2.4, 1.8 Hz), 6.75(1H, d, J=8.8 Hz), 6.77(1H, d, J=8.2 Hz), 6.81(1H, dd, J=8.2, 1.6 Hz), 6.85(1H, d, J=1.6 Hz), 7.41(1H, dd, J=8.8, 2.4 Hz), 7.65(1H, d, J=1.8 Hz), 7.69(1H, d, J=2.4 Hz), 7.76(1H, d, J=2.4 Hz)

EXAMPLE 67

2-Amino-N-(3,4-methylenedioxybenzyl)-5-(1,2,4-triazol-1-yl)benzamide

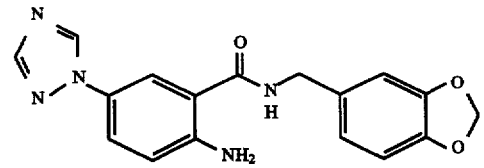

The title compound was obtained as a white powder in a similar manner to that of Example 66 (yield: 94%).

M.P.: 163° to 164° C.

MASS: 338(MH⁺)

$^1$H-NMR(400 MHz, CDCl$_3$) δ:

4.51(2H, d, J=5.5 Hz), 5.79(2H, s), 5.96(2H, s), 6.48(1H, s), 6.78(1H, d, J=8.2 Hz), 6.78(1H, d, J=8.9 Hz), 6.81(1H, dd, J=8.2, 1.6 Hz), 6.85(1H, d, J=1.6 Hz), 7.41(1H, dd, J=8.9, 2.4 Hz), 7.62(1H, d, J=2.4 Hz), 8.03(1H, s), 8.37(1H, s)

EXAMPLE 68

2-Amino-N-(3-chloro-4-methoxybenzyl)-5-cyano-4-methoxybenzamide

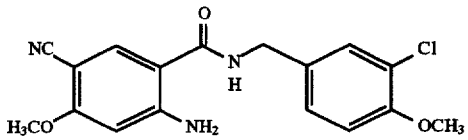

2-Amino-5-bromo-N-(3-chloro-4-methoxybenzyl)-4-methoxybenzamide (4.67 g) was dissolved in 10 ml of N-methyl-2-pyrrolidone, followed by the addition of 1.15 g of cuprous cyanide. The obtained mixture was stirred at 180° C. for 4 hours, followed by the addition of an aqueous solution of ethylenediamine. The obtained mixture was extracted with ethyl acetate. The organic phase was washed with water and a saturated aqueous solution of common salt, dried over anhydrous magnesium sulfate, and concentrated in a vacuum. The residue was purified by silica gel column chromatography (solvent: n-hexane/ethyl acetate (3:2)). The obtained solid was washed with ether to give 1.58 g of the title compound as a slightly yellow powder (yield: 39%).

M.P.: 184° to 185° C.

MASS: 346(MH⁺)

$^1$H-NMR(400 MHz, CDCl$_3$) δ:

3.88(3H, s), 3.90(3H, s), 4.48(2H, d, J=5.9 Hz), 6.08(1H, s), 6.32–6.42(3H, m), 6.91(1H, d, J=8.4 Hz), 7.21(1H, dd, J=8.4, 2.2 Hz), 7.36(1H, d, J=2.2 Hz), 7.59(1H, s)

EXAMPLE 69

7-Amino-4-bromo-N-(3,4-methylenedioxybenzyl)isoindoline-1-one

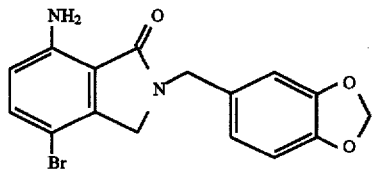

7-Amino-4-bromoisoindoline (0.35 g) was suspended in 50 ml of N,N-dimethylformamide, followed by the addition of 0.29 g of 60% sodium hydride. The obtained mixture was stirred at room temperature for 45 minutes, followed by the addition of 0.29 g of piperonyl chloride. The obtained mixture was stirred at room temperature for 4 hours, followed by the addition of ice-water. The resulting mixture was extracted with ethyl acetate. The organic phase was washed with 1N hydrochloric acid, water, a saturated aqueous solution of sodium hydrogencarbonate, water and a saturated aqueous solution of common salt, dried over anhydrous magnesium sulfate, and concentrated in a vacuum. The residue was purified by silica gel column chromatography (solvent: n-hexane/ethyl acetate (3:1)). The obtained solid was washed with n-hexane to give 0.25 g of the title compound as a pale-yellow powder (yield: 46%).

M.P.: 151° to 153° C.

MASS: 361(MH⁺)

$^1$H-NMR(400 MHz, CDCl$_3$) δ:

4.08(2H, s), 4.63(2H, s), 5.26(2H, s), 5.95(2H, s), 6.50 (1H, d, J=8.6 Hz), 6.76–6.79(3H, m), 7.28(1H, d, J=8.6 Hz)

EXAMPLE 70

8-Amino-5-bromo-N-(3,4-methylenedioxybenzyl)

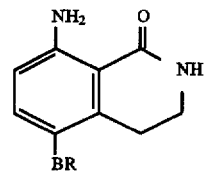

The title compound was obtained as a slightly yellow powder in a similar manner to that of Example 69 (yield: 84%).

$^1$H-NMR(400 MHz, CDCl$_3$) δ:

2.94(2H, t, J=6.6 Hz), 3.40(2H, t, J=6.6 Hz), 4.63(2H, s), 5.94(2H, s), 6.18(2H, s), 6.46(1H, d, J=8.8 Hz), 6.75 (1H, dd, J=7.9, 0.5 Hz), 6.78(1H, dd, J=7.9, 1.2 Hz), 6.82(1H, dd, J=1.2, 0.7 Hz), 7.30(1H, d, J=8.8 Hz)

EXAMPLE 71

1-[[4-Chloro-2-[(3,4-methylenedioxybenzyl)carbamoyl]phenyl]carbamoyl]-4-hydroxypiperidine

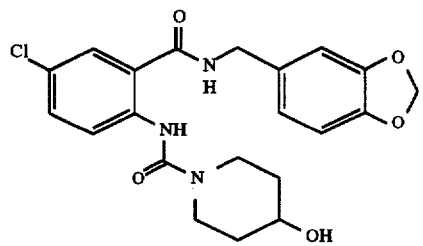

1-[(2-Carboxy-4-chlorophenyl)carbamoyl]-4-hydroxypiperidine (0.5 g), piperonylamine (0.42 ml), 1,3-dicyclohexylcarbodiimide (0.38 g), 1-hydroxybenztriazole (0.25 g) and 4-dimethylaminopyridine (25 mg) were added to 8 ml of N,N-dimethylformamide. The obtained mixture was stirred at room temperature for 61 hours, followed by the addition of water and ethyl acetate. The resulting mixture was filtered to remove insolubles. The organic phase was recovered, washed with 1N hydrochloric acid, water, a saturated aqueous solution of sodium hydrogencarbonate, water, and a saturated aqueous solution of common salt, dried over anhydrous magnesium sulfate, and concentrated in a vacuum. The residue was purified by silica gel column chromatography (solvent: dichloromethane/methanol (30:1) ). The obtained residue was crystallized from n-hexane/ethyl acetate and recrystallized from aqueous ethanol to give 0.39 g of the title compound as a white powder (yield: 53%).

M.P.: 151° to 155° C. (dec.)

MASS: 432(MH⁺)

$^1$H-NMR(400 MHz, CDCl$_3$) δ:

0.56(2H, m), 1.74(1H, m), 1.95(2H, m), 3.21(2H, ddd, J=13.6, 9.3, 3.3 Hz), 3.83–3.97(3H, m), 4.47(2H, d, J=5.7 Hz), 5.96(2H, s), 6.87(1H, dd, J=7.9, 0.5 Hz), 6.81(1H, dd, J=7.9, 1.6 Hz), 6.85(1H, dd, J=1.6, 0.5 Hz), 7.03(1H, t, J=5.7 Hz), 7.25(1H, dd, J=9.2, 2.4 Hz), 7.33(1H, d, J=2.4 Hz), 8.21(1H, d, J=9.2 Hz), 10.57 (1H, s)

EXAMPLE 72

Ethyl 1-[[4-bromo-2-[(3,4-methylenedioxybenzyl)carbamoyl]phenyl]carbamoyl]piperidine-4-carboxylate

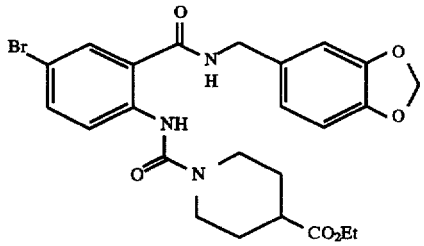

Ethyl 1-[(4-bromo-2-carboxyphenyl)carbamoyl]-piperidine-4-carboxylate (1.2 g), piperonylamine (0.56 ml), 1,3-dicyclohexylcarbodiimide (0.68 g), 1-hydroxybenztriazole (0.45 g) and 4-dimethylaminopyridine (catalytic amount) were added to 10 ml of N,N-dimethylformamide. The obtained mixture was stirred at room temperature for 20 hours, followed by the addition of water and ethyl acetate. The resulting mixture was filtered to remove insolubles. The organic phase was recovered, washed with 1N hydrochloric acid, water, a saturated aqueous solution of sodium hydrogencarbonate, water, and a saturated aqueous solution of common salt, dried over anhydrous magnesium sulfate, and concentrated in a vacuum. The obtained residue was purified by silica gel column chromatography (solvent: n-hexane/ethyl acetate (2:1)). The obtained solid was washed with ether to give 1.27 g of the title compound as a white powder (yield: 77%).

M.P.: 156° to 159° C.

MASS: 532(MH⁺)

¹H-NMR(400 MHz, CDCl₃) δ:

1.27(3H, t, J=7.1 Hz), 1.75(2H, m), 1.99(2H, m), 2.52(1H, m), 3.05(2H, m), 4.09(2H, m), 4.16(2H, q, J=7.1 Hz), 4.47(2H, d, J=5.7 Hz), 5.97(2H, s), 6.79(1H, dd, J=8.1, 0.5 Hz), 6.82(1H, dd, J=8.1, 1.5 Hz), 6.85(1H, dd, J=1.5, 0.5 Hz), 6.89(1H, t, J=5.7 Hz), 7.39(1H, dd, J=9.0, 2.4 Hz), 7.46(1H, d, J=2.4 Hz), 8.19(1H, d, J=9.0 Hz), 10.57(1H, s)

EXAMPLE 73

1-[[4-Chloro-2-[(3-chloro-4-methoxybenzyl)carbamoyl]phenyl]carbamoyl]-4-hydroxypiperidine

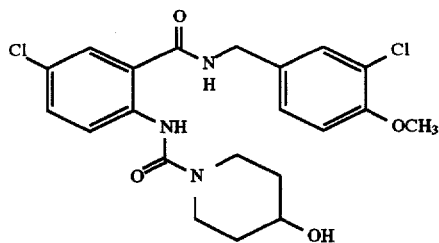

1-[(2-Carboxy-4-Chlorophenyl)carbamoyl]-4-hydroxypiperidine (0.5 g), 3-chloro-4-methoxybenzylamine hydrochloride (0.7 g), 1,3-dicyclohexylcarbodiimide (0.38 g), 1-hydroxybenztriazole (0.25 g), 4-dimethylaminopyridine (25 mg) and triethylamine (0.47 ml) were added to 8 ml of N,N-dimethylformamide. The obtained mixture was stirred at room temperature for 61 hours, followed by the addition of water and ethyl acetate. The obtained mixture was filtered to remove insolubles. The organic phase was recovered, washed with 1N hydrochloric acid, water, a saturated aqueous solution of sodium hydrogencarbonate, water, and a saturated aqueous solution of common salt, dried over anhydrous magnesium sulfate, and concentrated in a vacuum. The residue was purified by silica gel column chromatography (solvent: dichloromethane/methanol (30:1)). The obtained residue was crystallized from n-hexane/ethyl acetate and recrystallized from aqueous ethanol to give 0.51 g of the title compound as a white powder (yield: 66%).

M.P.: 173° to 174° C. (dec.)

MASS: 452(MH⁺)

¹H-NMR(400 MHz, DMSO-d₆) δ:

1.33(2H, m), 1.76(2H, m), 3.11(2H, ddd, J=13., 9.5, 3.1 Hz), 3.64–3.78(3H, m), 3.84(3H, s), 4.40(2H, d, J=5.7 Hz), 4.46(1H, d, J=4.2 Hz), 7.11(1H, d, J=8.6 Hz), 7.28(1H, dd, J=8.6, 2.2 Hz), 7.41(1H, d, J=2.2 Hz), 7.50(1H, dd, J=9.2, 2.6 Hz), 7.82(1H, d, J=2.6 Hz), 8.32(1H, d, J=9.2 Hz), 9.37(1H, t, J=5.7 Hz), 11.02(1H, s)

EXAMPLE 74

1-[[2-[(3-Chloro-4-methoxybenzyl)carbamoyl]-4-cyanophenyl]carbamoyl]-4-hydroxypiperidine

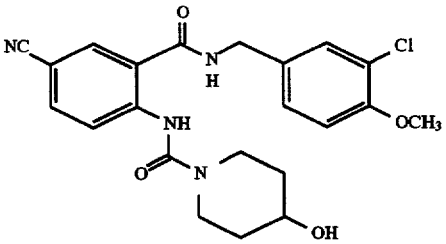

The title compound was obtained as a white powder in a similar manner to that of Example 73 (yield: 13%).

M.P.: 194° to 196° C.

MASS: 443(MH⁺)

¹H-NMR(400 MHz, DMSO-d₆) δ:

1.35(2H, m), 1.77(2H, m), 3.16(2H, m), 3.64–3.80(3H, m), 3.84(3H, s), 4.42(2H, d, J=5.5 Hz), 4.77(1H, d, J=4.2 Hz), 7.11(1H, d, J=8.4 Hz), 7.29(1H, dd, J=8.9, 2.0 Hz), 7.43(1H, d, J=2.0 Hz), 7.86(1H, dd, J=9.0, 1.6

Hz), 8.24(1H, d, J=1.6 Hz), 8.49(1H, d, J=9.0 Hz), 9.42(1H, m), 11.47(1H, s)

EXAMPLE 75

Ethyl 1-[[4-bromo-2-[(3-chloro-4-methoxybenzyl)carbamoyl]phenyl]carbamoyl]piperidine-4-carboxylate

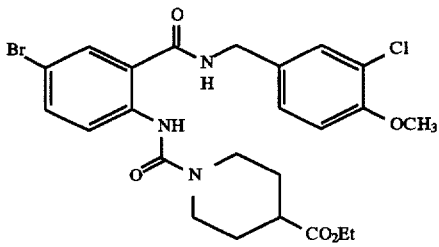

Ethyl 1-[(4-bromo-2-carboxyphenyl]carbamoyl]-piperidine-4-carboxylate (1.0 g), 3-chloro-4-methoxy benzylamine (0.78 g), 1.3-dicyclohexylcarbodiimide (0.57 g), 1-hydroxybenztriazole (0.37 g), 4-dimethyl-aminopyriding (catalytic amount), and triethyiamine (0.52 ml) were added to 8 ml of N,N-dimethylformamide. The obtained mixture was stirred at room temperature for 66 hours, followed by the addition of water and ethyl acetate. The resulting mixture was filtered to remove insolubles. The organic phase was recovered, washed with 1N hydrochloric acid, water, a saturated aqueous solution of sodium hydrogencarbonate, water, and a saturated aqueous solution of common salt, dried over anhydrous magnesium sulfate, and concentrated in a vacuum. The residue was purified by silica gel column chromatography (solvent: n-hexane/ethyl acetate (2:1)). The obtained solid was washed with ether to give 1.00 g of the title compound as a white powder (yield: 72%).

M.P.: 172° to 174° C.

MASS: 554(MH$^+$)

$^1$H-NMR(400 MHz, CDCl$_3$) δ:

1.27(3H, t, J=7.1 Hz), 1.75(2H, m), 1.99(2H, m), 2.52(1H, m), 3.05(2H, m), 3.91(3H, s), 4.08(2H, m), 4.16(2H, q, J=7.1 Hz), 4.47(2H, d, J=5.7 Hz), 6.92(1H, d, J=8.4 Hz), 7.22(1H, m), 7.22(1H, dd, J=8.4, 2.2 Hz), 7.33 (1H, dd, J=9.2, 2.4 Hz), 7.41(1H, d, J=2.2 Hz), 7.45 (1H, d, J=2.4 Hz), 8.10(1H, d, J=9.2 Hz), 10.53(1H, s)

EXAMPLE 76

5-Chloro-N-(3-chloro-4-methoxybenzyl)-2-(piperidineoacetamido)benzamide

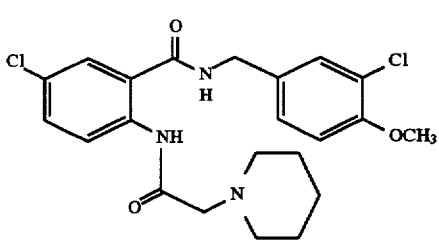

5-Chloro-2-chloroacetamido-N-(3-chloro-4-methoxybenzyl)benzamide (0.7 g), piperidine (0.51 ml), anhydrous potassium carbonate (0.72 g) and tetra(n-butyl) ammonium iodide (catalytic amount) were added to 6 ml of N,N-dimethylformamide. The obtained mixture was stirred at room temperature for 1.5 hours, followed by the addition of water. The resulting mixture was extracted with ethyl acetate. The organic phase was washed with water and a saturated aqueous solution of common salt, dried over anhydrous magnesium sulfate, and concentrated in a vacuum. The residue was purified by silica gel column chromatography (solvent: n-hexane/ethyl acetate (3:1)) and recrystallized from aqueous ethanol to give 0.37 g of the title compound as a white needle (yield: 48%).

M.P.: 126° to 129° C.

MASS: 450(MH$^+$)

$^1$H-NMR(400 MHz, CDCl$_3$) δ:

1.42-1.50(2H, m), 1.66-1.74(4H, m), 2.46-2.56(4H, m), 3.07(2H, s), 3.90(3H, s), 4.53(2H, d, J=5.7 Hz), 6.62 (1H, t, J=5.9 Hz), 6.89(1H, d, J=8.4 Hz), 7.20(1H, dd, J=8.4, 2.2 Hz), 7.32(1H, dd, J=9.0, 2.0 Hz), 7.36(1H, d, J=2.2 Hz), 7.40(1H, d, J=2.4 Hz), 8.49(1H, d, J=9.0 Hz), 11.52(1H, s)

EXAMPLE 77

5-Chloro-N-(3-chloro-4-methoxybenzyl)-2-(pyrrolidinoacetamido)benzamide

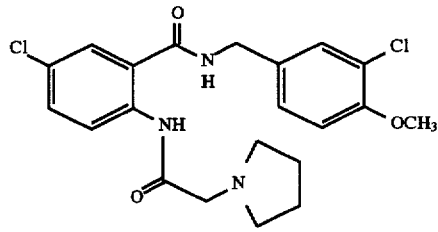

The title compound was obtained as a slightly yellow prism in a similar manner to that of Example 24 (yield: 86%).

M.P.: 98° to 100° C.

MASS: 436(MH$^+$)

$^1$H-NMR(400 MHz, CDCl$_3$) δ:

1.81-1.92(4H, m), 2.61-2.72(4H, m), 3.28(2H, s), 3.89 (3H, s), 4.49(2H, d, J=5.9 Hz), 6.88(1H, d, J=8.4 Hz), 6.89(1H, t, J=5.9 Hz), 7.19(1H, dd, J=8.4, 2.2 Hz), 7.27(1H, dd, J=9.0, 2.4 Hz), 7.35(1H, d, J=2.2 Hz), 7.41(1H, d, J=2.4 Hz), 8.42(1H, d, J=9.0 Hz), 11.49 (1H, s)

EXAMPLE 78

5-Chloro-N-(3,1-methylenedioxybenzyl)-2-(pyrrolidinoacetamido)benzamide

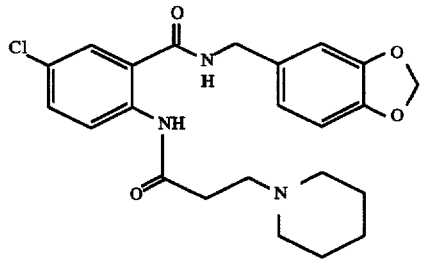

The title compound was obtained as a slightly yellow needle in a similar manner to that of Example (yield: 60%).

M.P.: 136° to 141° C.

MASS: 444(MH$^+$)

$^1$H-NMR(400 MHz, CDCl$_3$) δ:

1.40–1.48(2H m); 1.56–1.64(4H, m), 2.44(4H, s), 2.56(2H, t, J=7.0 Hz), 2.70(2H, t, J=7.0 Hz), 4.48(2H, d, J=5.7 Hz), 5.97(2H, s), 6.26(1H, m), 6.78(1H, d, J=7.8 Hz), 6.80(1H, d, J=7.8 Hz), 6.83(1H, s), 7.35(1H, dd, J=9.0, 2.4 Hz), 7.40(1H, d, J=2.4 Hz), 8.81(1H, d, J=9.0 Hz), 11.03(1H, s)

EXAMPLE 79

5-Chloro-N-(3,4-methylenedioxybenzyl)-2-(4-piperidinobutyrylamino)benzamide

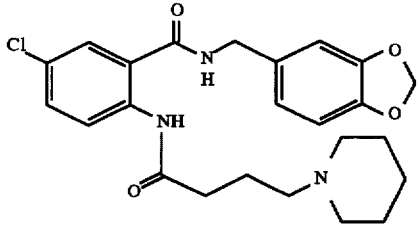

The title compound was obtained as a slightly yellow needle in a similar manner to that of Example (yield: 7%).
M.P.: 121° to 122° C.
MASS: 458(MH$^+$) $^1$H-NMR(400 MHz, CDCl$_3$) δ:
1.37–1.45(2H, m), 1.51–1.59(4H, m), 1.91(2H, quintet, J=7.5Hz), 2.31–2.48(8H, m), 4.50(2H, d, J=5.7Hz), 5.98(2H, s), 6.43(1H, m), 6.78–6.85(3H, m), 7.39(1H, d, J=2.6Hz), 7.89(1H, dd, J=9.7, 2.6 Hz), 8.56(1H, d, J=9.7Hz), 10.96(1H, s)

EXAMPLE 80

N-(3-Chloro-4-methoxybenzyl)-5-cyano-2-(isonicotinoylamino)benzamide

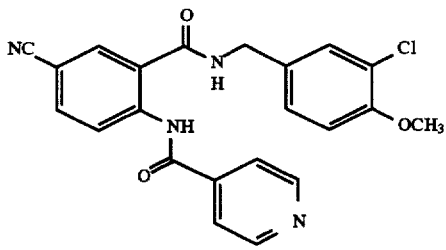

2-Amino-N-(3-chloro-4-methoxybenzyl)-5-cyanobenzamide (0.33 g) was dissolved in 5 ml of pyridine, followed by cooling with ice. Isonicotinoyl chloride hydrochloride (0.2 g) was added to the resulting solution. The obtained mixture was stirred at room temperature for 4 hours, followed by the addition of water. The precipitates formed were recovered by filtration, washed with water and ether, and recrystallized from ethyl acetate to give 0.27 g of the title compound as a slightly yellow needle (yield: 64%).
M.P.: 243° to 245° C. (dec.)
MASS: 421(MR$^+$)
$^1$H-NMR(400 MHz, DMSO-d$_6$) δ:
3.83(3H, s), 4.47(2H, d, J=5.7 Hz), 7.32(1H, dd, J=8.4, 2.2 Hz), 7.46(1H, d, J=2.2 Hz), 7.79–7.83(2H, m), 8.06(1H, dd, J=8.8, 1.8 Hz), 8.40(1H, d, J=1.8 Hz), 8.77(1H, d, J=8.8 Hz), 8.84–8.88(2H, m), 9.56(1H, t, J=5.7 Hz), 12.90(1H, s)

EXAMPLE 81

5-Bromo-N-(3-chloro-4-methoxybenzyl-2-(isonicotinoylamino)benzamide

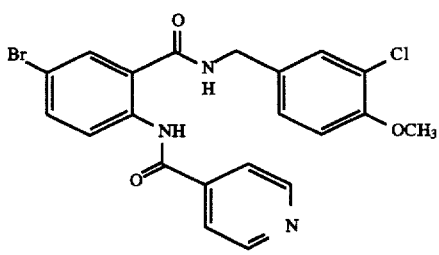

The title compound was obtained as a white needle in a similar manner to hat of Example 80 (yield: 7s).
M.P.: 190° to 192° C.
MASS: 476(MH$^+$)
$^1$H-NMR(400MHz, CDCl$_3$) δ:
3.90(3H, s), 4.57(2H, d, J=5.7 Hz), 6.70(1H, t, J=5.7 Hz), 6.92(1H, d, J=8.4 Hz), 7.23(1H, dd, J=8.4, 2.2 Hz), 7.40(1H, d, J=2.2 Hz), 7.64(1H, dd, J=9.3, 2.2 Hz), 7.65(1H, d, J=2.2 Hz), 7.83–7.87(2H, m), 8.72(1H, d, J=9.3 Hz), 8.81–8.85(2H, m), 12.33(1H, s)

EXAMPLE 82

5-Bromo-N-(3-chloro-4-methoxybenzyl)-2-(isonicotinoylamino)-4-methoxybenzamide

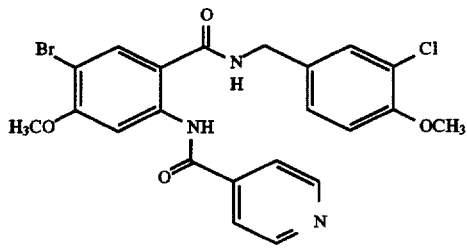

The title compound was obtained as a white needle in a similar manner to that of Example 80 (yield: 40%).
M.P.: 252° to 253° C. (dec.)
MASS: 506(MH$^+$)
$^1$H-NMR(400 MHz, DMSO-d$_6$) δ:
3.83(3H, s), 3.95(3H, s), 4.45(2H, d, J=5.7 Hz), 7.11(1H, d, J=8.6 Hz), 7.30(1H, dd, J=8.6, 2.2 Hz), 7.42(1H, d, J=2.2 Hz), 7.80–7.84(2H, m), 8.24(1H, s), 8.55(1H, s), 8.84–8.88(2H, m), 9.39(1H, t, J=5.7 Hz), 13.26(1H, s)

EXAMPLE 83

N-(3-Chloro-4-methoxybenzyl)-5-cyano-2-(isonicotinoylamino)-4-methoxybenzamide

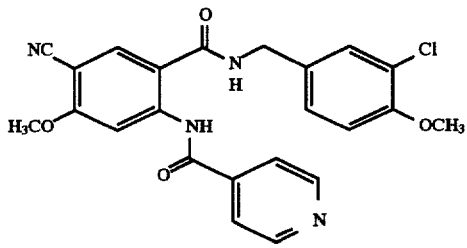

The title compound was obtained as a white needle in a similar manner to that of Example 80 (yield: 81%).
M.P.: 262° to 267° C. (dec.)

MASS: 451(MH⁺)

¹H-NMR(400 MHz, DMSO-d₆) δ:
3.83(3H, s), 4.00(3H, s), 4.46(2H, d, J5.7 Hz), 7.11(1H, d, J=8.6 Hz), 7.81(1H, dd, J=8.6, 2.2 Hz), 7.44(1H, d, J=2.2 Hz), 7.81–7.84(2H, m), 8.40(1H, s), 8.60(1H, s), 8.85–8.90(2H, m), 9.42(1H, t, J=5.7 Hz), 13.48(1H, s)

EXAMPLE 84

5-Bromo-2-(isonicotinoylamino)-4-methoxy-N-(3,4-methylenedioxybenzyl)benzamide

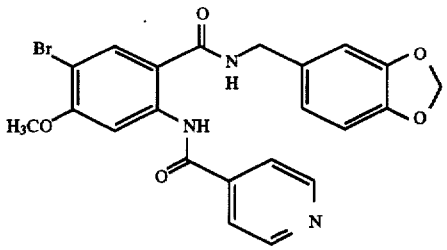

The title compound was obtained as a slightly yellow needle in a similar manner to that of Example 30 (yield: 75%)

¹H-NMR(400 MHz, DMSO-d₆)

M.P.: 249° to 254° C. (dec.)

MASS: 484(M^{H+})

3.94(3H, s), 4.42(2H, d, J=5.7 Hz), 5.98(2H, s), 6.83(1H, dd, J=8.0, 1.3 Hz), 6.86(1H, dd, J=8.0, 0.4 Hz), 6.94(1H, dd, J=1.3, 0.4 Hz), 7.80–7.84(2H, m), 8.24(1H, s), 8.55(1H, s), 8.85–8.88(2H, m), 9.36(1H, t, J=5.7 Hz), 13.32(1H, s)

EXAMPLE 85

5-Bromo-2-(isonicotinoylamino)-N-(3,4-methylenedioxybenzyl)benzamide

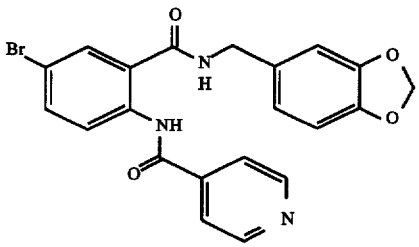

The title compound was obtained as a slightly yellow needle in a similar manner to that of Example 80 (yield: 49%).

M.P.: 207° to 211° C.

MASS: 454 (H⁺)

¹H-NMR(400 Hz, DMSO-d₆) δ:
4.42(2H, d, J=5.7 Hz), 5.98(2H, s), 6.83(1H, dd, J=7.9, 1.5 Hz), 6.86(1H, d, J=7.9 Hz), 6.95(1H, d, J=1.5 Hz), 7.75–7.83(3H, m), 8.10(1H, d, J=2.2 Hz), 8.53(1H, d, J=9.0 Hz), 8.81–8.87(2H, m), 9.48(1H, t, J=5.7 Hz), 12.61(1H, s)

EXAMPLE 86

N-(3-Chloro-4-methoxybenzyl)-5-cyano-2-[(trans-4-cyanocyclohexanecarbonyl)amino]benzamide

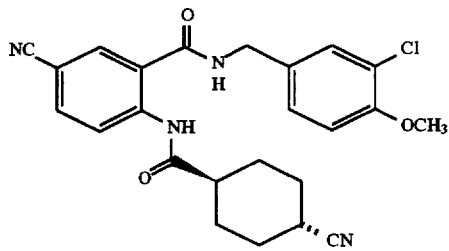

2-Amino-N-(3-chloro-4-methoxybenzyl)-5-cyanobenzamide (0.5 g) was dissolved in 8 ml of pyridine, followed by cooling with ice. A solution of 0.33 g of trans-4-cyanocyclohexanecarbonyl chloride in 1 ml of dichloromethane was dropped into the above solution in such a way that the bulk temperature did not exceed 10° C. The obtained mixture was stirred for 2 hours, followed by the addition of ice-water. The resulting mixture was extracted with ethyl acetate. The organic phase was washed with 1N hydrochloric acid, water, a saturated aqueous solution of sodium hydrogen-carbonate, water, and a saturated aqueous solution of common salt, dried over anhydrous magnesium sulfate, and concentrated in a vacuum. The residue was purified by silica gel column chromatography (solvent: dichloromethane/methanol (100: 1)) and recrystallized from aqueous ethanol to give 0.44 g of the title compound as a white needle (yield: 61%).

M.P.: 188° to 184° C.

MASS: 451(MH⁺)

¹H-NMR(400 MHz, CDCl₃) δ:
1.54–1.75(4H, m), 2.08–2.18(2H, m), 2.20–2.28(2H, m), 2.89(1H, m), 2.51(1H, m), 8.91(8H, s), 4.53(2H, d, J=5.7 Hz), 8.92(1H, t, J=5.7 Hz), 6.93(1H, d, J=8.4 Hz), 7.22 (1H, dd, J=8.4, 2.2 Hz), 7.39(1H, d, J=2.2 Hz), 7.70(1H, dd, J=8.0, 2.0 Hz), 7.86(1H, d, J=2.0 Hz), 8.79(1H, d, J=8.8 Hz), 11.57(1H, s)

EXAMPLE 87

5-Bromo-2-[(tans-4-cyanocyclohexanecarbonyl)amino]-N-(3,4-methylenedioxybenzyl)benzamide

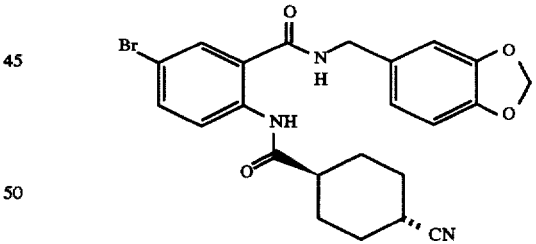

The title compound was obtained as a white granular crystal in a similar manner to that of Example 86 (yield: 75).

M.P.: 147° to 149° C.

MASS: 484(MH⁺)

¹H-NMR(400 MHz, CDCl₃) δ:
1.54–1.73(4H, m), 2.07–2.14(2H, m), 2.19–2.27(2H, m), 2.35(1H, m), 2.50(1H, m), 4.51(2H, d, J=5.5 Hz), 5.98 (2H, s), 6.47(1H, m), 6.80(2H, s), 6.84(1H, s), 7.55(1H, dd, J=9.5, 2.2 Hz), 7.55(1H, d, J=2.2 Hz), 8.52(1H, d, J=9.5 Hz), 11.13(1H, s)

EXAMPLE 88

2-[[(trans-4-(Acetoxy)cyclohexancarbonyl)-amino]-N-(3-chloro-4-methoxybenzyl)-5-cyanobenzamide

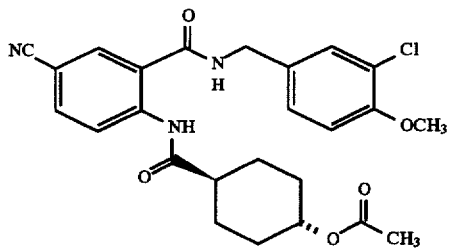

The title compound was obtained as a white needle in a similar manner to that of Example 34 (yield: 60%).

M.P.: 194° to 196° C.

MASS: 484(MH⁺)

¹H-NMR(400 MHz, CDCl₃) δ:

1.39–1.50(2H, m), 1.62–1.74(2H, m), 2.05(3H, s), 2.05–2.15(4H, m), 2.34(1H, tt, J=11.7, 3.3 Hz), 3.91(3H, s), 4.54(2H, d, J=5.9 Hz), 4.73(1H, tt, J=11.0, 4.0 Hz), 6.82(1H, t, J=5.9 Hz), 6.93(1H, d, J=8.4 Hz), 7.23(1H, dd, J=8.4, 2.2 Hz), 7.40(1H, d, J=2.2 Hz), 7.70(1H, dd, J=8.8, 2.0 Hz), 7.83(1H, d, J=2.0 Hz), 8.81(1H, d, J=8.8 Hz), 11.47(1H, s)

EXAMPLE 89

5-Chloro-N-(3,4-methylenedioxybenzyl-2-[(trans-4-piperidinocyclohexanecarbonyl)amino]benzamide

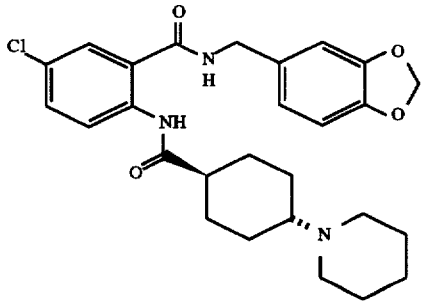

The title compound was obtained as a slightly yellow needle in a similar manner to that of Example 86 (yield: 17%).

M.P.: 162° to 163° C.

MASS: 498(MH⁺)

¹H-NMR(400 MHz, CDCl₃) δ:

1.29–1.48(4H, m), 1.50–1.63(6H, m), 2.00(2H, m), 2.10(2H, m), 2.22(1H, m), 2.32(1H, m), 2.46–2.58(4H, m), 4.51 (2H, d, J=5.7 Hz), 5.97(2H, s), 6.51(1H, t, J=5.7 Hz), 6.77–6.85(3H, m), 7.38(1H, dd, J=8.6, 2.6 Hz), 7.39(1H, d, J=2.6 Hz), 8.57(1H, d, J=8.6 Hz), 10.94(1H, s)

EXAMPLE 90

N-(3-Chloro-4-methoxybenzyl)-5-cyano-2-[(trans-4-piperidinocyclohexanecarbonyl)amino]benzamide

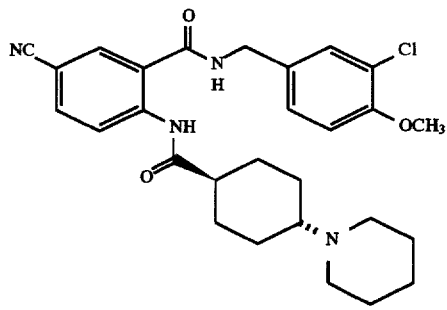

The title compound was obtained as a white needle in a similar manner to that of Example 86 (yield: 2%).

M.P.: 215° to 218° C. (dec.)

MASS: 509(MH⁺)

¹H-NMR(400 MHz, CDCl₃) δ:

1.31–1.48(4H, m), 1.51–1.64(4H, m), 2.01(2H, m), 2.11(2H, m), 2.22–2.38(2H, m), 2.48–2.56(4H, m), 3.91(3H, s), 4.54(2H, d, J=5.7 Hz), 6.71(1H, t, J=5.7 Hz), 6.93(1H, d, J=8.4 Hz), 7.22(1H, dd, J=8.4, 2.2 Hz), 7.40(1H, d, J=8.8, 2.0 Hz), 7.79(1H, d, J=2.0 Hz), 8.81 (1H, d, J=8.8 Hz), 11.34(1H, s)

EXAMPLE 91

N-(3-Chloro-4-methoxybenzyl)-5-cyano-2-[[(trans-4-(ethoxycarbonyl)cyclohexanecarbonyl)amino]benzamide

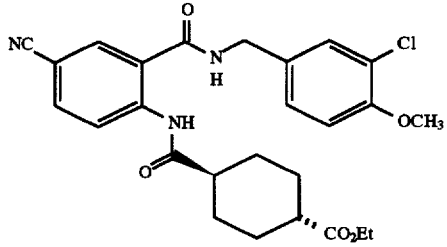

2-Amino-N-(3-chloro-4-methoxybenzyl)-5-cyanobenzamide (1.2 g) was dissolved in 10 ml of pyridine, followed by cooling with ice. A solution of 1.0 g of trans-4-(ethoxycarbonyl)cyclohexanecarbonyl chloride in 2 ml of dichloromethane was dropped into the solution prepared above in such a way that the bulk temperature did not exceed 10° C. The obtained mixture was stirred for 4 hours, followed by the addition of ice-water. The resulting mixture was extracted with ethyl acetate. The organic phase was washed with 1N hydrochloric acid, water, a saturated aqueous solution of sodium hydrogencarbonate, water, and a saturated aqueous solation of common salt, dried over anhydrous magnesium sulfate, and concentrated in a vacuum. The residue was purified by silica gel column chromatography (solvent: n-hexane/ethylacetate (2: 1)). The obtained solid was washed with ether to give 0.9 g of the title compound as a white powder (yield: 48% ).

M.P.: 153° to 155° C.

MASS: 498(MH⁺)

¹H-NMR(400 MHz, CDCl₃) δ:

1.26(3H, t, J=7.1 Hz), 1.46–1.64(4H, m), 2.05–2.19(4H, m), 2.28–2.38(2H, m), 3.91(3H, s), 4.14(2H, q, J=7.1 Hz), 4.54(2H, d, J=5.7 Hz), 6.82(1H, t, J=5.7 Hz), 6.93(1H, d, J=8.4 Hz), 7.23(1H, dd, J=8.4, 2.2 Hz), 7.40(1H, d, J=2.2 Hz), 7.69(1H, dd, J=9.0, 1.8 Hz), 7.83(1H, d, J=1.8 Hz), 8.81(1H, d, J=9.0 Hz), 11.45(1H, s)

EXAMPLE 92

N-(3-Chloro-4-methoxybenzyl)-2-[[(trans-4-(ethoxycarbonyl)cyclohexanecarbonyl)amino]-5-nitrobenzamide

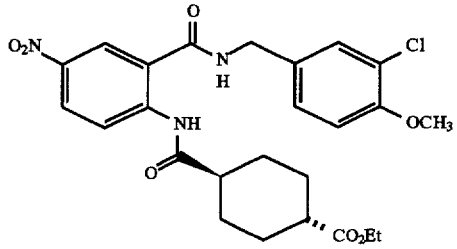

The title compound was obtained as a pale-yellow powder in a similar manner to that of Example 91 (yield: 614%).

M.P.: 166° to 169° C.

MASS: 518(MH$^+$)

$^1$H-NMR(400 MHz, CDCl$_3$) δ:

1.27(8H, t, J=7.1 Hz), 1.47–1.66(4H, m), 2.07–2.20(4H, m), 2.29–2.40(2H, m), 8.91(8H, s), 4.14(2H, q, J=7.1 Hz), 4.57(2H, d, J=5.7 Hz), 6.79(1H, t, J=8.4 Hz), 6.98(1H, d, J=8.4 Hz), 7.24(1H, dd, J=8.4, 2.2 Hz), 7.41(1H, d, J=2.2 Hz), 8.80(1H, dd, J=9.3, 2.6 Hz), 8.39(1H, d, J=2.6 Hz), 8.88(1H, d, J=9.3 Hz), 11.64(1H, s)

EXAMPLE 93

5-Chloro-N-(3-chloro-4-methoxybenzyl)-2-[[(trans-4-(ethoxycarbonyl)cyclohexanecarbonyl)amino]benzamide

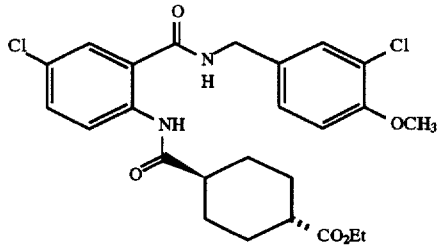

The title compound was obtained as a white powder in a similar manner to that of Example 91 (yield: 83%).

M.P.: 122° to 125° C.

MASS: 507(MH$^+$)

$^1$H-NMR(400 MHz, CDCl$_3$) δ:

1.26(3H, t, J=7.1 Hz), 1.43–1.63(4H, m), 2.06–2.14(4H, m), 2.24–2.36(2H, m), 3.91(3H, s), 4.13(2H, q, J=7.1 Hz), 4.52(2H, d, J=5.7 Hz), 6.67(1H, t, J=5.7 Hz), 6.92(1H, d, J=8.4 Hz), 7.21(1H, dd, J=8.4, 2.2 Hz), 7.37(1H, d, J=2.2 Hz), 7.38(1H, dd, J=9.0, 2.4 Hz), 7.42(1H, d, J=2.4 Hz), 8.55(1H, d, J=9.0 Hz), 10.99(1H, s)

EXAMPLE 94

5-Chloro-2-[[(trans-4-(ethoxycarbonyl)cyclohexanecarbonyl)amino]-N-[(2-methoxy-5-pyridyl)methyl]benzamide

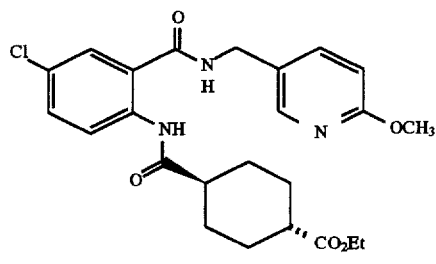

The title compound was obtained as a white powder in a similar manner to that of Example 91 (yield: 94%).

M.P.: 141° to 144° C.

MASS: 474(MH$^+$)

$^1$H-NMR(400 MHz, CDCl$_3$) δ:

1.26(3H, , J=7.1 Hz), 1.45–1.63(4H, m), 2.04–2.18(4H, m), 2.24–2.36(2H, m), 3.94(3H, s), 4.14(2H, q, J=7.1 Hz), 4.54(2H, d, J=5.7 Hz), 6.55(1H, t, J=5.7 Hz), 6.76(1H, d, J=8.6 Hz), 7.39(1H, d, J=2.4 Hz), 7.40(1H, dd, J=9.7, 2.4 Hz), 7.59(1H, dd, J=8.6, 2.6 Hz), 8.16(1H, d, J=2.6 Hz), 8.58(1H, d, J=9.7 Hz), 10.98(1H, s)

EXAMPLE 95

5-Chloro-N-(3-cyano-4-methoxybenzyl)-2-[[(trans-4-(ethoxycarbonyl)cyclohexanecarbonyl)amino]benzamide

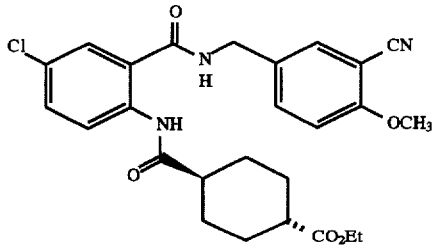

The title compound was obtained as a white powder in a similar manner to that of example 91 (yield:

M.P.: 157° to 160° C.

*Ms: 496(MH$^+$)

$^1$H-NMR(400 MHz, CDCl$_3$) δ:

1.26(3H, t, J=7.1 Hz), 1.44–1.62(4H, m), 2.03–2.17(4H, m), 2.24–2.36(2H, m), 3.94(3$_H$, s), 4.13(2H, q, J=7.1 Hz), 4.55(2H, d, J=5.9 Hz), 6.85(1H, t, J=5.9 Hz), 6.98(1H, m), 7.39(1H, dd, J=9.0, 2.4 Hz), 7.44(1H, d, J=2.4 Hz), 7.53–7.58(2H, m), 8.56(1H, d, J=9.0 Hz), 11.00(1H, s)

EXAMPLE 96

5-Chloro-N-(4-chloro-3-methoxybenzyl)-2-[[(trans-4-(ethoxycarbonyl)cyclohexanecarbonyl)amino]benzamide

87

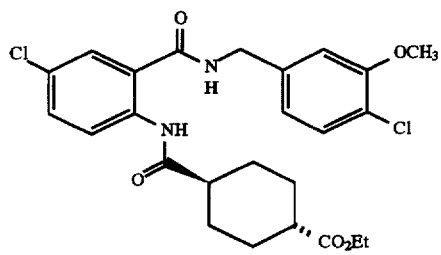

The title compound was obtained as a white powder in a similar manner to that of Example 91 (yield: 83%).

M.P.: 167° to 168° C.

MASS: 507(MH$^+$)

$^1$H-NMR(400 MHz, CDCl$_3$) δ:

1.26(3H, t, J=7.1 Hz), 1.44–1.64(4H, m), 2.04–2.18(4H, m), 2.25–2.36(2H, m), 3.92(3H, s), 4.13(2H, q, J=7.1 Hz), 4.58(2H, d, J=5.7 Hz), 6.54(1H, t, J=5.7 Hz), 6.88(1H, dd, J=8.1, 1.6 Hz), 6.91(1H, d, J=1.6 Hz), 7.36(1H, d, J=8.1 Hz), 7.42(1H, d, J=2.2 Hz), 7.42(1H, dd, J=9.5, 2.2 Hz), 8.60(1H, d, J=9.5 Hz), 10.99(1H, s)

EXAMPLE 97

5-Bromo-N-(3-chloro-5-methoxybenzyl)-2-[[(trans-4-(ethoxycarbonyl)cyclohexanecarbonyl)amino]-4-methoxybenzamide

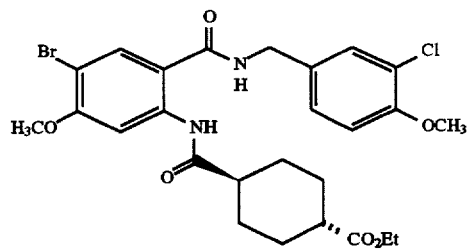

The title compound was obtained as a white powder in a similar manner to that of Example 91 (yield: 76%).

M.P.: 160° C. (dec.)

MASS: 583(MH$^+$)

$^1$H-NMR(400 MHz, CDCl$_3$) δ:

1.26(3H, t, J=7.1 Hz), 1.46–1.65(4H, m), 2.08–2.16(4H, m), 2.27–2.37(2H, m), 3.91(3H, s), 3.95(3H, s), 4.13(2H, q, J=7.1 Hz), 4.51(2H, d, J=5.5 Hz), 6.41(1H, t, J=5.5 Hz), 6.92(1H, d, J=8.4 Hz), 7.21(1H, dd, J=8.4, 2.2 Hz), 7.37(1H, d, J=2.2 Hz), 7.61(1H, s), 8.52(1H, s), 11.62(1H, s)

EXAMPLE 98

5-Bromo-4-methoxy-N-(3-chloro-4-methoxybenzyl-2-[[(trans- 4-(ethoxycarbonyl)cyclohexanecarbonyl)amino] benzamide

88

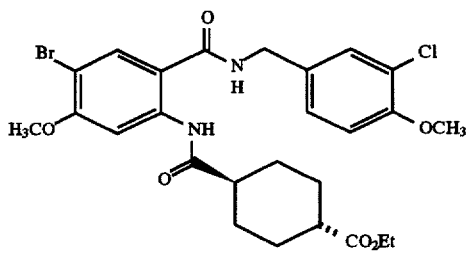

The title compound was obtained as a white powder in a similar manner to that of Example 91 (yield: 71%).

M.P.: 171° to 173° C.

MASS: 553(MH$^+$)

$^1$H-NMR(400 MHz, CDCl$_3$) δ:

1.26(3H, t, J=7.1 Hz), 1.43–1.62(4H, m), 2.03–2.16(4H, m), 2.24–2.35(2H, m), 3.90(3H, s), 4.13(2H, q, J=7.1 Hz), 4.52(2H, d, J=5.7 Hz), 6.79(1H, t, J=5.7 Hz), 6.91(1H, d, J=8.4 Hz), 7.21(1H, dd, J=8.4, 2.2 Hz), 7.37(1H, d, J=2.2 Hz), 7.50(1H, dd, 9.0, 2.4 Hz), 7.57(1H, d, J=2.4 Hz), 8.47(1H, d, J=9.0 Hz), 11.01(1H, s)

EXAMPLE 99

N-(3-Chloro-4-methoxybenzyl)-5-cyano-2-[[(trans-4-(ethoxycarbonyl)cyclohexanecarbonyl)amino]-4-methoxybenzamide

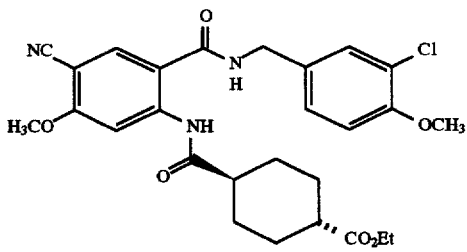

The title compound was obtained as a white powder in a similar manner to that of Example 91 (yield: 72%).

M.P.: 193° to 195° C.

MASS: 526(M$^{H+}$)

$^1$H-NMR(400 MHz, CDCl$_3$) δ:

1.26(3H, t, J=7.1 Hz), 1.46–1.65(4H, m), 2.06–2.19(4H, m), 2.28–2.39(2H, m), 3.91(3H, s), 3.98(3H, s), 4.14(2H, q, J=7.1 Hz), 4.51(2H, d, J=5.7 Hz), 6.66(1H, t, J=5.7 Hz), 6.93(1H, d, J=8.6 Hz), 7.22(1H, dd, J=8.6, 2.2 Hz), 7.39(1H, d, J=2.2 Hz), 7.75(1H, s), 8.58(1H, s), 11.92(1H, s)

EXAMPLE 100

N-(3-Chloro-4-methoxybenzyl)-5-dimethylsulfamoyl-2-[ [(trans-4-(ethoxycarbonyl)cyclohexanecarbonyl)amino] benzamide

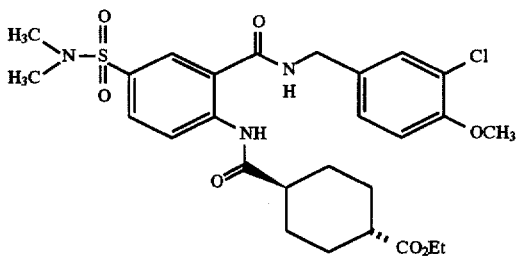

The title compound was obtained as a white powder in a similar manner to that of Example 91 (yield: 89%).

M.P.: 197° to 198° C.

MASS: 580(MH⁺)

$^1$H-NMR(400 MHz, CDCl$_3$) δ:

1.27(3H, t, J=7.1 Hz), 1.47–1.65(4H, m), 2.06–2.19(4H, m), 2.29–2.39(2H, m), 2.67(6H, s), 3.90(3H, s), 4.14(2H, q, J=7.1 Hz), 4.56(2H, d, J=5.9 Hz), 6.90(1H, d, J=8.4 Hz), 7.26(1H, dd, J=8.4, 2.2 Hz), 7.32(1H, t, J=5.9 Hz), 7.42(1H, d, J=2.2 Hz), 7.79(1H, dd, J=9.0, 2.2 Hz), 7.99(1H, d, J=2.2 Hz), 8.88(1H, d, J=9.0 Hz), 11.63(1H, s)

EXAMPLE 101

N-(3-Chloro-4-methoxybenzyl)-2-[[(trans-4-(ethoxycarbonyl)cyclohexanecarbonyl)amino]-5-methylsulfamoylbenzamide

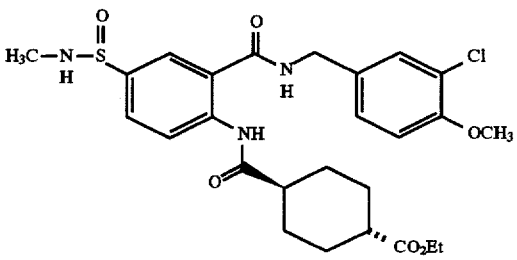

The title compound was obtained as a white powder in a similar manner to that of Example 91 (yield: 44%).

M.P.: 190° to 191° C.

MASS: 566(MH⁺)

$^1$H-NMR(400 MHz, CDCl$_3$) δ:

1.27(3H, t, J=7.1 Hz), 1.46–1.65(4H, m), 2.06–2.18(4H, m), 2.29–2.39(2H, m), 2.61(3H, d, J=5.3 Hz), 8.89(3H, s), 4.14(2H, q, J=7.1 Hz), 4.58(2H, d, J=5.9 Hz), 4.65(1H, q, J=5.3 Hz), 6.89(1H, d, J=8.6 Hz), 7.20(1H, t, J=5.9 Hz), 7.23(1H, dd, J=8.6, 2.2 Hz), 7.40(1H, d, J=2.2 Hz), 7.84(1H, dd, J=9.0, 2.2 Hz), 8.03(1H, d, J=2.2 Hz) 8.83(1H, d, J=9.0 Hz), 11.58(1H, s)

EXAMPLE 102

2-[[(trans-4-(Ethoxycarbonyl)cyclohexanecarbonyl)amino]-N-(3,4-methylenedioxybenzyl)-5-(1-pyrazolyl)benzamide

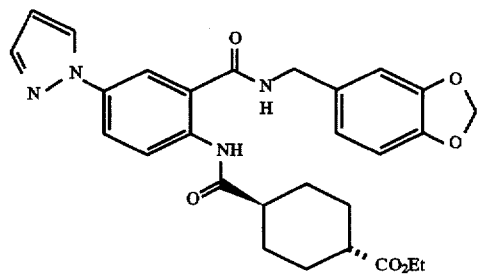

The title compound was obtained as a white powder in a similar manner to that of Example 88 (yield: 85%).

M.P.: 197° to 201° C.

MASS: 519(MH⁺)

$^1$H-NMR(400 MHz, CDCl$_3$) δ:

1.27(3H, , J=7.1 Hz), 1.46–1.66(4H, m), 2.08–2.18(4H, m), 2.27–2.38(2H, m), 4.14(2H, q, J=7.1 Hz), 4.52(2H, d, J=5.7 Hz), 5.96(2H, s), 6.47(1H, dd, J=2.4, 1.6 Hz), 6.78(1H, d, J=7.9 Hz), 6.80(1H, dd, J=7.9, 1.6 Hz), 6.84(1H, d, J=1.6 Hz), 6.85(1H, m), 7.59(1H, dd, J=9.2, 2.6 Hz), 7.68(1H, d, J=1.6 Hz), 7.89(1H, d, J=2.6 Hz), 7.95(1H, d, J=2.4 Hz), 8.73(1H, d, J=9.2 Hz), 11.18(1H, s)

EXAMPLE 103

2-[[(trans-4-(Ethoxycarbonyl)cyclohexanecarbonyl)amino]-N-(3,4-methylenedioxybenzyl)-5-(1,2,4-triazol-1-yl)benzamide

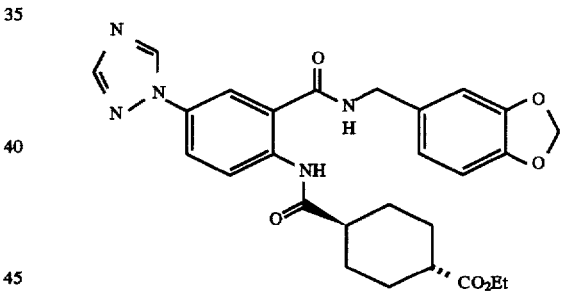

The title compound was obtained as a white powder in a similar manner to that of Example 86 (yield: 69%).

M.P.: 204° to 206° C.

MASS: 520(MH⁺)

$^1$H-NMR(400 MHz, CDCl$_3$) δ:

1.27(3H, t, J=7.1 Hz), 1.45–1.65(4H, m), 2.05–2.19(4H, m), 2.28–2.38(2H, m), 4.14(2H, q, J=7.1 Hz), 4.55(2H, d, J=5.7 Hz), 5.97(2H, s), 6.79(1H, d, J=7.9 Hz), 6.82(1H, dd, J=7.9, 1.6 Hz), 6.85(1H, d, J=1.6 Hz), 6.91(1H, t, J=5.7 Hz), 7.64(1H, dd, J=9.2, 2.6 Hz), 7.86(1H, d, J=2.6 Hz), 8.05(1H, s), 8.49(1H, s), 8.79(1H, d, J=9.2 Hz), 11.21(1H, s)

EXAMPLE 104

2-[[(trans-4-(Ethoxycarbonyl)cyclohexanecarbonyl)amino]-N-(3,4-methylenedioxybenzyl)-5-trifluoromethoxybenzamide

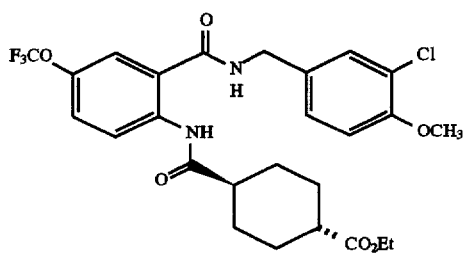

The title compound was obtained as a white powder in a similar manner to that Example 86 (yield: 63%).

M.P.: 179° to 180° C.

MASS: 537(MH⁺)

¹H-NMR(400 MHz, CDCl₃) δ:

1.26(3H, t, J=7.1 Hz), 1.44–1.64(4H, m), 2.05–2.17(4H, m), 2.25–2.37(2H, m), 4.13(2H, q, J=7.1 Hz), 4.52(2H, d, J=5.7 Hz), 5.97(2H, s), 6.53(1H, t, J=5.7 Hz), 6.79(1H, d, J=7.9 Hz), 6.81(1H, d, J=7.9 Hz), 6.84(1H, s), 7.28(1H, d, J=2.7 Hz), 7.32(1H, dd, J=9.2, 2.7 Hz), 8.66(1H, d, J=9.2 Hz), 11.03(1H, s)

EXAMPLE 105

5-Cyano-2-[[(trans-4-ethoxycarbonyl)cyclohexanecarbonyl)amino]-N-(3,4-methylenedioxybenzyl)benzamide

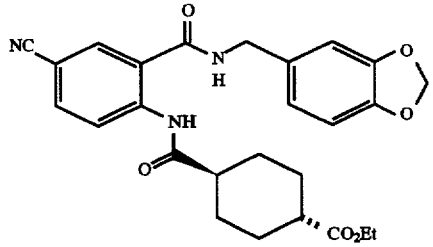

The title compound was obtained as a white powder in a similar manner to that of Example 86 (yield: 36%).

M.P.: 150° to 153° C.

MASS: 478(MH⁺)

¹H-NMR(400 MHz, CDCl₃) δ:

1.26(3H, t, J=7.1 Hz), 1.46–1.64(4H, m), 2.05–2.18(4H, m), 2.28–2.38(2H, m), 4.14(2H, q, J=7.1 Hz), 4.52(2H, d, J=5.7 Hz), 5.98(2H, s), 6.75(1H, t, J=5.7 Hz), 6.80(1H, dd, J=7.9, 0.7 Hz), 6.83(1H, dd, J=7.9, 1.3 Hz), 6.85(1H, dd, J=1.3, 0.7 Hz), 7.69(1H, dd, J=9.0, 2.0 Hz), 7.81(1H, d, J=2.0 Hz), 8.80(1H, d, J=9.0 Hz), 11.46(1H, s)

EXAMPLE 106

5-Bromo-2-[[(trans-4-(ethoxycarbonyl)cyclohexanecarbonyl)amino]-4-methoxy-N-(3,4-methylenedioxybenzyl)benzamide

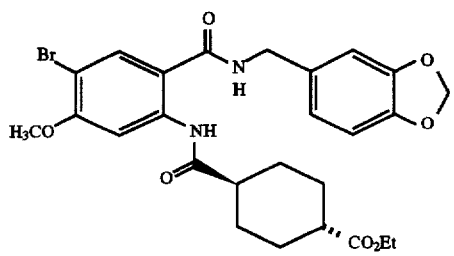

The title compound was prepared as a white powder in a similar manner to that of Example 86 (yield: 67%).

M.P.: 194° to 195° C.

MASS: 561 (MH⁺)

¹H-NMR(400 MHz, CDCl₃) δ:

1.26(3H, t, J=7.1 Hz), 1.46–1.66(4H, m), 2.08–2.16(4H, m), 2.27–2.37(2H, m), 3.95(3H, s), 4.13(2H, q, J=7.1 Hz), 4.50(2H, d, J=5.5 Hz), 5.97(2H, s), 6.35(1H, t, J=5.5 Hz), 6.80(2H, s), 6.84(1H, s), 7.60(1H, s), 8.52(1H, s), 11.65 (1H, s)

EXAMPLE 107

4-Bromo-7-[(trans-4-(ethoxycarbonyl)cyclohexanecarbonyl)amino]-N-(3,4-methylenedioxybenzyl)isoindoline-1-one

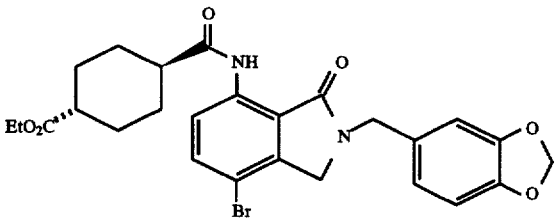

The title compound was obtained as a white powder in a similar manner to that of Example 86 (yield: 67%).

M.P.: 135° to 137° C.

MASS: 543(MH⁺)

¹H-NMR(400 MHz, CDCl₃) δ:

1.26(3H, t, J=7.1 Hz), 1.46–1.68(4H, m), 2.10–2.20(4H, m), 2.29–2.41(2H, m), 4.14(2H, q, J=7.1 Hz), 4.17(2H, s), 4.66(2H, s), 5.96(2H, s), 6.76–6.82(3H, m), 7.55(1H, d, J=8.8 Hz), 8.44(1H, d, J=8.8 Hz), 10.49.(1H, s)

EXAMPLE 108

5-Bromo-8-[(trans-4-(ethoxycarbonyl)cyclohexanecarbonyl)amino]-N-(3,4-methylenedioxybenzyl)-1,2,3,4-tetrahydro-1-isoquinoline-1-one

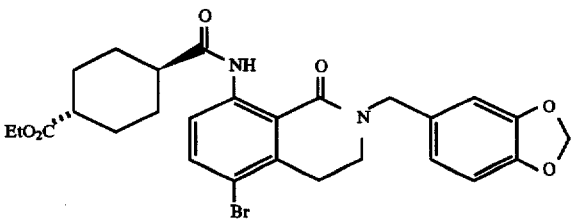

The title compound was obtained as a colorless oil in a similar manner to that of Example 86 (yield: 85%).

MASS: 557(MH⁺)

¹H-NMR(400 MHz, CDCl₃) δ:
1.26(3H, t, J=7.1 Hz), 1.46–1.67 (4H, m), 2.06–2.17(4H, m), 2.28–2.38(2H, m), 3.01(2H, t, J=6.6 Hz), 3.46(2H, t, J=6.6 Hz), 4.13(2H, q, J=7.1 Hz), 4.67(2H, s), 5.96(2H, s), 6.77(1H, dd, J=7.2, 1.3 Hz), 6.79(1H, d, J=7.2 Hz), 6.81(1H, d, J=1.3 Hz), 7.60(1H, d, J=9.0 Hz), 8.57(1H, d, J=9.0 Hz), 12.38(1H, s)

EXAMPLE 109

N-(3-Chloro-4-methoxybenzyl)-5-cyano-2-[(trans-4-hydroxycyclohexanecarbonyl)amino]benzamide

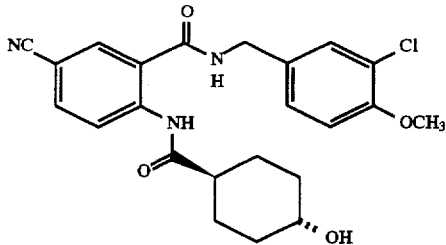

2-[[(trans-4-(Acetoxy)cyclohexanecarbonyl)amino)-N-(3-chloro-4-methoxybenzyl)-5-cyanobenzamide (0.9 g) was dissolved in a solvent mixture comprising 10 ml of ethanol and 10 ml of tetrahydrofuran, followed by the addition of 8 ml of 1N sodium hydroxide. The obtained mixture was stirred at room temperature for 2 hours, followed by the addition of water. The resulting mixture was extracted with an ethyl acetate/tetrahydrofuran/ethanol mixture. The organic phase was washed with a saturated aqueous solution of common salt, dried over anhydrous magnesium sulfate, and distilled in a vacuum to remove the solvent. The obtained solid was washed with ether and recrystallized from aqueous ethanol to give 0.33 g of the title compound as a white needle (yield: 39%).

M.P.: 164° to 165° C.

MASS: 442(MH⁺)

¹H-NMR(400 MHz, DMSO-d₆) δ:
1.14–1.26(2H, m), 1.35–1.47(2H, m), 1.83–1.93(4H, m), 3.35(1H, m), 3.84(3H, s), 4.42(2H, d, J=5.5 Hz), 4.61(1H, d, J=4.4 Hz), 7.12(1H, d, J=8.4 Hz), 7.30(1H, dd, J=8.4, 2.2 Hz), 7.44(1H, d, J=2.2 Hz), 7.94(1H, dd, J=8.8, 2.0 Hz), 8.25(1H, d, J=2.0 Hz), 8.58(1H, d, J=8.8 Hz), 9.24(1H, t, J=5.5 Hz), 11.54(1H, s)

EXAMPLE 110

2-[(trans-4-Carboxycyclohexanecarbonyl)amino]-N-(3-chloro-4-methoxybenzyl)-5-cyanobenzamide

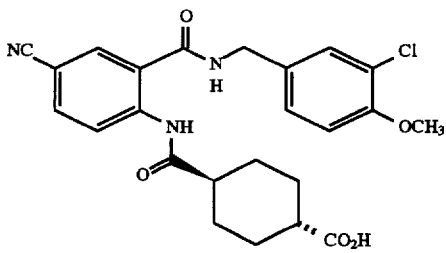

N-(3-Chloro-4-methoxybenzyl)-5-cyano-2-[[(trans-4-(ethoxycarbonyl)cyclohexanecarbonyl)amino]benzamide (0.9 g) was dissolved in a solvent mixture comprising 10 ml of ethanol and 10 ml of tetrahydrofuran, followed by the addition of 8 ml of 1N sodium hydroxide. The obtained mixture was stirred at room temperature for 8 hours, followed by the addition of water and ethyl acetate. The aqueous phase was recovered. The ethyl acetate phase was extracted with water. The obtained aqueous phase and the above one were combined and acidified with 1N hydrochloric acid. The precipitates formed were recovered by filtration and recrystallized from aqueous ethanol to give 0.42 g of the title compound as a white needle (yield: 72%).

M.P.: 223° to 227° C.

MASS: 470(MH⁺)

¹H-NMR(400 MHz, DMSO-d₆) δ:
1.32–1.48(4H, m), 1.89–2.02(4H, m), 2.18(1H, m), 2.31(1H, m), 3.84(3H, s), 4.43(2H, d, J=5.7 Hz), 7.12(1H, d, J=8.6 Hz), 7.31(1H, dd, J=8.6, 2.2 Hz), 7.44(1H, d, J=2.2 Hz), 7.93(1H, dd, J=8.8, 2.0 Hz), 8.26(1H, d, J=2.0 Hz), 8.60(1H, d, J=8.8 Hz), 9.43(1H, t, J=5.7 Hz), 11.57(1H, s), 12.10(1H, s)

EXAMPLE 111

1-[[4-Bromo-2-[(3-chloro-4-methoxybenzyl)carbamoyl]phenyl]carbamoyl]piperidine-4-carboxylic acid

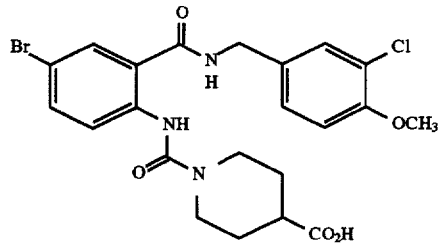

The title compound was obtained as a white powder in a similar manner to that of Example 110 (yield: 64%).

M.P.: 259° C. (dec.)

MASS: 526(MH⁺)

¹H-NMR(400 MHz, DMSO-d₆) δ:
1.48(2H, m), 1.87(2H, m), 2.49(1H, m), 2.98(1H, m), 3.84(3H, s), 8.91(2H, m), 4.40(2H, d, J=5.7 Hz), 7.11(1H, d, J=8.6 Hz), 7.28(1H, dd, J=8.6, 2.0 Hz), 7.61(1H, d, J=2.0 Hz), 7.94(1H, d, J=2.4 Hz), 8.26(1H, d, J=9.2 Hz), 9.38(1H, t, J=5.7 Hz), 11.04(1H, s), 12.30(1H, s)

EXAMPLE 112

2-[(trans-4-Carboxycyclohexanecarbonyl)amino]-5-chloro-N-(3-chloro-4-methoxybenzyl)benzamide

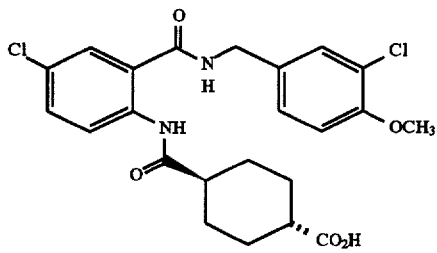

The title compound was obtained as a white needle in a similar manner to that of Example 110 (yield: 77%).

M.P.: 233° to 235° C.

MASS: 478 (MH⁺)

¹H-NMR(400 MHz, DMSO-d₆) δ:

1.30–1.47(4H, m), 1.85–2.02(4H, m), 2.13–2.29(2H, m), 3.84(3H, s), 4.40(2H, d, J=5.7 Hz), 7.11(1H, d, J=8.4 Hz), 7.29(1H, dd, J=8.4, 2.2 Hz), 7.41(1H, d, J=2.2 Hz), 7.55(1H, dd, J=9.0, 2.4 Hz), 7.82(1H, d, J=2.4 Hz), 8.39(1H, d, J=9.0 Hz), 9.35(1H, t, J=5.7 Hz), 11.15(1H, s), 12.08(1H, s)

EXAMPLE 113

5-Bromo-2-[(trans-4-carboxycyclohexanecarbonyl)amino]-N-(3-chloro-4-methoxybenzyl)benzamide

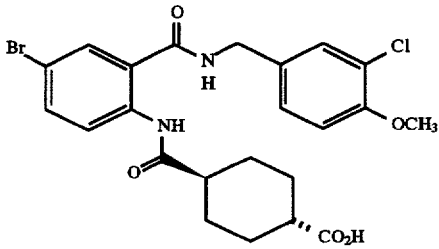

The title compound was obtained as a white needle in a similar manner to that of Example 110 (yield: 58%).

M.P.: 247° to 250° C.

MASS: 523(MH$^+$)

$^1$H-NMR(400 MHz, DMSO-d$_6$) δ:
1.30–1.48(4H, m), 1.88–2.02(4H, m), 2.13–2.29(2H, m), 3.84(3H, s), 4.40(2H, d, J=5.7 Hz), 7.11(1H, d, J=8.4 Hz), 7.28(1H, dd, J=8.4, 2.2 Hz), 7.41(1H, d, J=2.2 Hz), 7.67(1H, dd, J=9.0, 2.2 Hz), 7.94(1H, d, J=2.2 Hz), 8.33(1H, d, J=9.0 Hz), 9.35(1H, t, J=5.7 Hz), 11.16(1H, s), 12.08(1H, s)

EXAMPLE 114

2-[(trans-4-Carboxycyclohexanecarbonyl)amino]-N-(3-chloro-4-methoxybenzyl)-5-nitrobenzamide

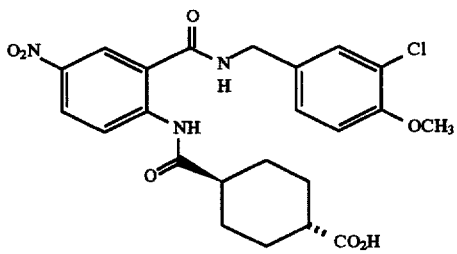

The title compound was obtained as a pale-yellow needle in a similar manner to that of Example 110 (yield: 65%).

M.P.: 285° to 244° C. (dec.)

MASS: 490(MH$^+$)

$^1$H-NMR(400 MHz, DMSO-d$_6$) δ:
1.82–1.50(4H, m), 1.91–2.04(4H, m), 2.18(1H, m), 2.84(1H, m), 8.84(8H, s), 4.45(2H, d, J=5.3 Hz), 7.12(1H, d, J=8.4 Hz), 7.81(1H, dd, J=8.4, 2.2 Hz), 7.44(1H, d, J=2.2 Hz), 8.88(1H, dd, J=9.3, 2.7 Hz), 8.68(1H, d, J=9.3 Hz), 8.69(1H, d, J=2.7 Hz), 9.68(1H, t, J=5.3 Hz), 11.76(1H, s), 12.10(1H, s)

EXAMPLE 115

5-Bromo-2-[(trans-4-carboxycyclohexanecarbonyl)amino]-N-(8-chloro-4-methoxybenzyl)-4-methoxybenzamide

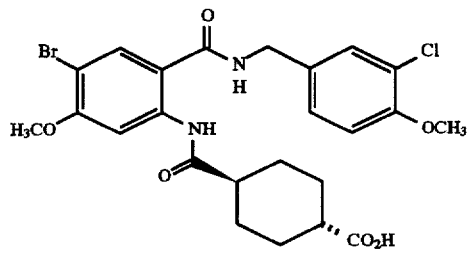

The title compound was obtained as a white needle in a similar manner to that of Example 110 (yield: 67%).

M.P.: 223° to 229° C.

MASS: 555(MH$^+$)

$^1$H-NMR(400 MHz, DMSO-d$_6$) δ:
1.32–1.50(4H, m), 1.90–2.02(4H, m), 2.18(1H, m), 2.26(1H, m), 3.83(3H, s), 3.87(3H, s), 4.39(2H, d, J=5.7 Hz), 7.11(1H, d, J=8.4 Hz), 7.27(1H, dd, J=8.4, 2.2 Hz), 7.39(1H, d, J=2.2 Hz), 8.09(1H, s), 8.42(1H, s), 9.24(1H, t, J=5.7 Hz), 11.92(1H, s), 12.01(1H, s)

EXAMPLE 116

2-[(trans-4-Carboxycyclohexanecarbonyl)amino]-N-(3-chloro-4-methoxybenzyl)-5-cyanobenzamide

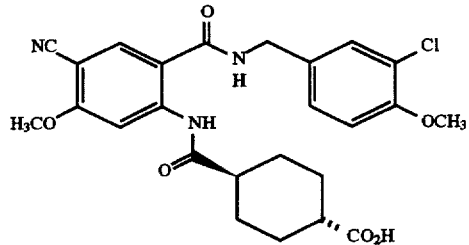

The title compound was obtained as a white needle in a similar manner to that of Example 110 (yield: 51%).

M.P.: 255° to 257° C.

MASS: 500(MH$^+$)

$^1$H-NMR(400 MHz, DMSO-d$_6$) δ:
1.33–1.51(4H, m), 1.91–2.03(4H, m), 2.19(1H, m), 2.31(1H, m), 3.84(3H, s), 3.93(3H, s), 4.41(2H, d, J=5.5 Hz), 7.11(1H, d, J=8.4 Hz), 7.29(1H, dd, J=8.4, 2.2 Hz), 7.41(1H, d, J=2.2 Hz), 8.27(1H, s), 8.47(1H, s), 9.28(1H, t, J=5.7 Hz), 12.01(1H, s), 12.19(1H, s)

EXAMPLE 117

2-[(trans-4-Carboxycyclohexanecarbonyl)amino]-N-(3-chloro-4-methoxybenzyl)-5-dimethylsulfamoylbenzamide

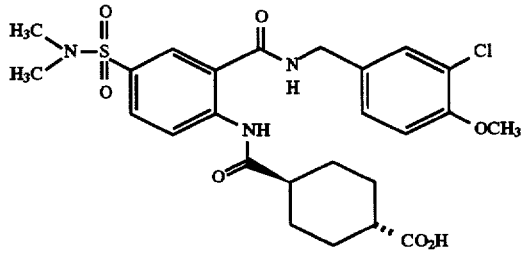

The title compound was obtained as a white needle in a similar manner to that of Example 110 (yield: 68%).

M.P.: 245° to 246° C.

MASS: 552(MH⁺)

¹H-NMR(400 MHz, DMSO-d₆) δ:
1.32–1.46(4H, m), 1.89–2.03(4H, m), 2.19(1H, m), 2.31(1H, m), 2.63(6H, s), 3.84(3H, s), 4.45(2H, d, J=5.7 Hz), 7.12(1H, d, J=8.4 Hz), 7.29(1H, dd, J=8.4, 2.0 Hz), 7.42(1H, d, J=2.0 Hz), 7.86(1H, dd, J=8.8, 2.2 Hz), 8.10(1H, d, J=2.2 Hz), 8.64(1H, d, J=8.8 Hz), 9.58(1H, t, J=5.7 Hz), 11.50(1H, s), 12.09(1H, s)

EXAMPLE 118

2-[(trans-4-Carboxycyclohexanecarbonyl)amino]-N-(3-chloro-4-methoxybenzyl)-5-methylsulfamoylbenzamide

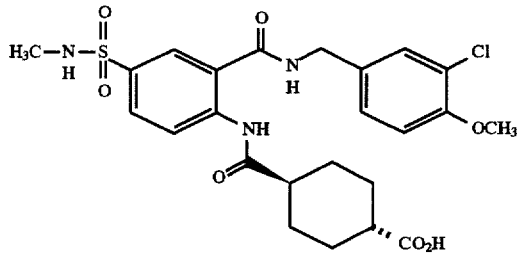

The title compound was obtained as a white needle in a similar manner to that of Example 110 (yield: 38%).

M.P.: 247° to 249° C.

MASS: 538(MH⁺)

¹H-NMR(400 MHz, DMSO-d₆) δ:
1.31–1.48(4H, m), 1.88–2.03(4H, m), 2.18(1H, m), 2.30(1H, m), 2.41(3H, d, J:4.9 Hz), 3.84(3H, s), 4.45(2H, d, J=5.9 Hz), 7.12(1H, d, J=8.4 Hz), 7.30(1H, dd, J=8.4, 2.2 Hz), 7.40(1H, q, J=4.9 Hz), 7.42(1H, d, J=2.2 Hz), 7.86(1H, dd, J=8.8, 2.2 Hz), 8.10(1H, d, J=2.2 Hz), 8.55(1H, d, J=8.8 Hz), 9.53(1H, t, J=5.9 Hz), 11.30(1H, s), 12.08(1H, s)

EXAMPLE 119

2-[(trans-4-Carboxycyclohexanecarbonyl)amino]-5-chloro-N-[(2-methoxy-5-pyridyl)methyl]benzamide

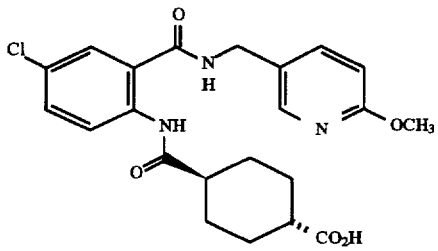

The title compound was obtained as a white needle in a similar manner to that of Example 110 (yield: 78%).

M.P.: 219° to 221° C.

MASS: 446(MH⁺)

¹H-NMR(400 MHz, DMSO-d₆) δ:
1.30–1.48(4H, m), 1.85–2.02(4H, m), 2.13–2.29(2H, m), 3.83(3H, s), 4.41(2H, d, J=5.7 Hz), 6.80(1H, d, J=8.6 Hz), 7.54(1H, dd, J=9.0, 2.4 Hz), 7.70(1H, dd, J=8.6, 2.4 Hz), 7.81(1H, d, J=2.4 Hz), 8.16(1H, d, J=2.4 Hz), 8.38(1H, d, J=9.0 Hz), 9.33(1H, t, J=5.7 Hz), 11.13(1H, s), 12.08(1H, s)

EXAMPLE 120

2-[(trans-4-Carboxycyclohexanecarbonyl)amino]-5-chloro-N-(3-cyano-4-methoxybenzyl)benzamide

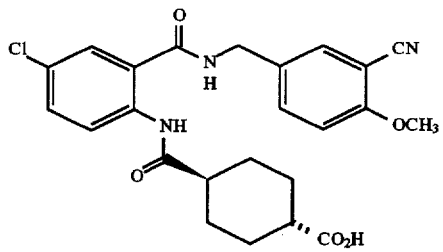

The title compound was obtained as a white needle in a similar manner to that of Example 110 (yield: 77%).

M.P.: 190° to 193° C.

MASS: 470(MH⁺)

¹H-NMR(400 MHz, DMSO-d₆) δ:
1.30–1.46(4H, m), 1.84–2.02(4H, m), 2.12–2.28(2H, m), 3.90(3H, s), 4.43(2H, d, J=5.7 Hz), 7.23(1H, d, J=8.8 Hz), 7.55(1H, dd, J=9.0, 2.6 Hz), 7.65(1H, dd, J=8.8, 2.4 Hz), 7.70(1H, d, J=2.4 Hz), 7.78(1H, d, J=2.6 Hz), 8.36(1H, d, J=9.0 Hz), 9.34(1H, t, J:5.7 Hz), 11.10(1H, s), 12.08(1H, s)

EXAMPLE 121

2-[(trans-4-Carboxycyclohexanecarbonyl)amino]-5-chloro-N-(4-chloro-3-methoxybenzyl)benzamide

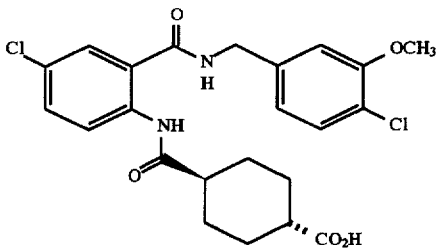

The title compound was obtained as a white needle in a similar manner to that of Example 110 (yield: 38%).

M.P.: 224° to 225° C.

MASS: 479(MH⁺)

¹H-NMR(400 MHz, DMSO-d₆) δ:
1.29–1.46(4H, m), 1.85–2.01(4H, m), 2.13–2.28(2H, m), 3.86(3H, s), 4.47(2H, d, J=5.9 Hz), 6.93(1H, dd, J=8.1, 1.5 Hz), 7.15(1H, d, J=1.5 Hz), 7.37(1H, d, J=8.1 Hz), 7.56(1H, dd, J=9.0, 2.4 Hz), 7.85(1H, d, J=2.4 Hz), 8.39(1H, d, J=9.0 Hz), 9.39(1H, t, J=5.9 Hz), 11.16(1H, s), 12.08(1H, s)

EXAMPLE 122

1-[[4-Bromo-2-[(3,4-methylenedioxybenzyl)carbamoyl]phenyl]carbamoyl]]carbamoyl]piperidine-4-carboxylic acid

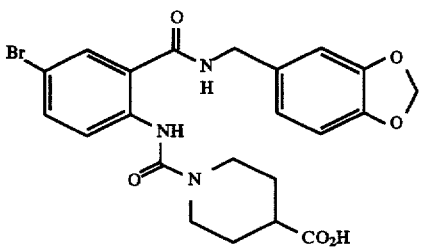

The title compound was obtained as a white powder in a similar manner to that of Example 110 (yield: 62%).

M.P.: 276° to 280° C. (dec.)
MASS: 504(MH$^+$)
$^1$H-NMR(400 MHz, DMSO-d$_6$) δ:
1.47(2H, m), 1.86(2H, m), 2.49(1H, m), 2.98(1H, m), 3.91 (2H, m), 4.37(2H, d, J=5.7 Hz), 5.99(2H, s), 6.81(1H, dd, J=7.9, 1.6 Hz), 6.87(1H, d, J=1.6 Hz), 6.92(1H, d, J=7.9 Hz), 7.61(1H, dd, J=9.2, 2.4 Hz), 7.94(1H, d, J=2.4 Hz), 8.26(1H, d, J=9.2 Hz), 9.35(1H, t, J=5.7 Hz), 11.07(1H, s), 12.30(1H, s)

EXAMPLE 123

4-Bromo-7-[(trans-4-carboxycyclohexanecarbonyl) amino]-N-(3,4-methylenedioxybenzyl)isoindoline-1-one

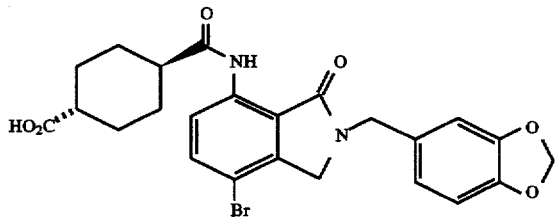

The title compound was obtained as a white needle in a similar manner to that of Example 110 (yield: 48%).

M.P.: 261° to 263° C.
MASS: 515($^{ME+}$)
$^1$H-NMR(400 MHz, DMSO-d$_6$) δ:
1.34–1.54(4H, m), 1.95–2.06(4H, m), 2.21(1H, m), 2.37(1H, m), 4.29(2H, s), 4.63(2H, s), 6.00(2H, s), 6.83(1H, dd, J=7.9, 1.6 Hz), 6.89(1H, d, J=7.9 Hz), 6.91(1H, d, J=1.6 Hz), 7.71(1H, d, J=8.8 Hz), 8.28(1H, d, J=8.8 Hz), 10.38(1H, s), 12.01(1H, s)

EXAMPLE 124

5-Bromo-8-[(trans-4-carboxycyclohexanecarbonyl) amino]-N-(3,4-methylenedioxybenzyl)-1,2,3,4-tetrahydroisoquinoline-1-one

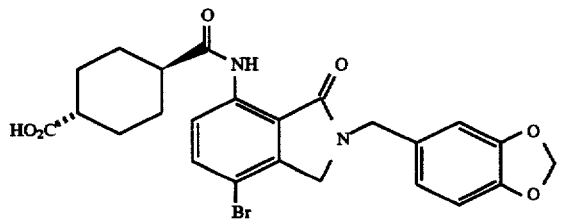

The title compound was obtained as a white needle in a similar manner to that of Example 110 (yield: 45%).

M.P.: 241° to 244° C.
MASS: 529($^{MH+}$)
$^1$H-NMR(400 MHz, DMSO-d$_6$) δ:
1.33–1.52(4H, m), 1.92–2.04(4H, m), 2.20(1H, m), 2.28(1H, m), 2.97(2H, t, J=8.1 Hz), 8.80(2H, t, J=6.8 Hz), 4.64(2H, s), 6.00(2H, s), 6.83(1H, dd, J=8.1, 1.5 Hz), 6.88(1H, d, J=8.1 Hz), 6.92(1H, d, J=1.5 Hz), 7.73(1H, d, J=9.0 Hz), 8.45(1H, d, J=9.0 Hz), 12.10(1H, s), 12.39(1H, s)

EXAMPLE 125

2-[(trans-4-Carboxycyclohexanecarbonyl)amino]-N-(3,4-methylenedioxybenzyl)-5-trifluoromethoxybenzamide

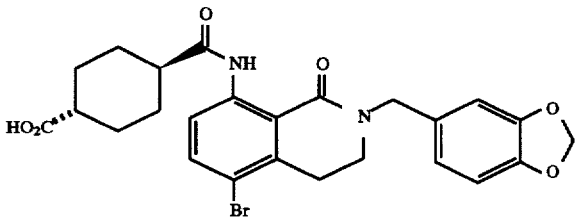

The title compound was obtained as a white needle in a similar manner to that of Example 110 (yield: 72%).

M.P.: 245° to 250° C.
MASS: 509(MH$^+$)
$^1$H-NMR(400 MHz, DMSO-d$_6$) δ:
1.31–1.48(4H, m), 1.88–2.03(4H, m), 2.14–2.32(2H, m), 4.39(2H, d, J=5.7 Hz), 5.99(2H, s), 6.82(1H, dd, J=8.1, 1.6 Hz), 6.87(1H, d, J=8.1 Hz), 6.94(1H, d, J=1.6 Hz), 7.52(1H, dd, J=9.2, 2.8 Hz), 7.76(1H, d, J=2.8 Hz), 8.46(1H, d, J=9.2 Hz), 9.33(1H, t, J=5.7 Hz), 11.22(1H, s), 12.09(1H, s)

EXAMPLE 126

2-[(trans-4-Carboxycyclohexanecarbonyl)amino]-N-(3,4-methylenedioxybenzyl)-5-(1-pyrazolyl)benzamide

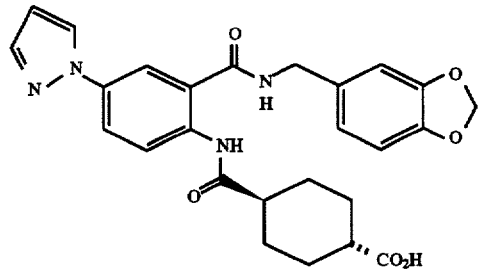

The title compound was obtained as a white needle similar manner to that of Example 110 (yield: 65%).

M.P.: 219° to 221° C.
MASS: 491 (MH$^+$)
$^1$H-NMR(400 MHz, DMSO-d$_6$) δ:
1.32–1.49(4H, m), 1.89–2.03(4H, m), 2.15–2.31(2H, m), 4.42(2H, d, J=5.9 Hz), 5.99(2H, s), 6.56(1H, dd, J=2.4, 1.8 Hz), 6.84(1H, dd, J=7.8, 1.5 Hz), 6.87(1H, d, J=7.8 Hz), 6.95(1H, d, J=1.5 Hz), 7.76(1H, d, J=1.8 Hz), 7.94(1H, dd, J=9.0, 2.6 Hz), 8.16(1H, d, J=2.6 Hz), 8.48(1H, d, J=9.0 Hz), 8.48(1H, d, J=2.4 Hz), 9.38(1H, t, J=5.9 Hz), 11.18(1H, s), 12.08(1H, s)

EXAMPLE 127

2-[(trans-4-Carboxycyclohexanecarbonyl)amino]-N-(3,4-methylenedioxybenzyl)-5-(1,2,4-triazol-1-yl)benzamide

101

2-[(trans-4-Carboxycyclohexanecarbonyl)amino]-5-cyano-N-(3,4-methylenedioxybenzyl)benzamide

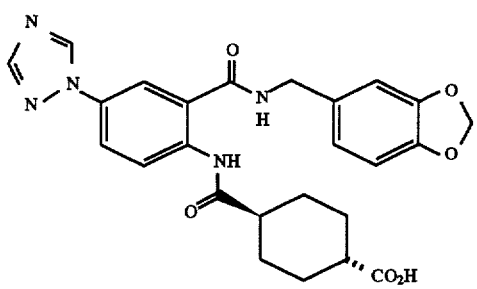

The title compound was obtained as a white needle in a similar manner to that of Example 110 (yield: 72%).

M.P.: 278° to 281° C. (dec.)

MASS: 492 (MH⁺)

$^1$H-NMR(400 MHz, DMSO-d$_6$) δ:
1.32–1.50(4H, m), 1.90–2.03(4H, m), 2.15–2.33(2H, m), 4.43(2H, d, J=5.7 Hz), 5.99(2H, s), 6.84(1H, dd, J=8.1, 1.1 Hz), 6.87(1H, d, J=8.1 Hz), 6.95(1H, d, J=1.1 Hz), 7.96(1H, dd, J=9.0, 2.4 Hz), 8.21(1H, d, J=2.4 Hz), 8.25(1H, s), 8.54(1H, d, J=9.0 Hz), 9.24(1H, s), 9.37(1H, t, J=5.7 Hz), 11.23(1H, s), 12.09(1H, s)

EXAMPLE 128

5-Bromo-2-[(trans-4-carboxycyclohexanecarbonyl)amino]-4-methoxy-N-(3,4-methylenedioxybenzyl)benzamide

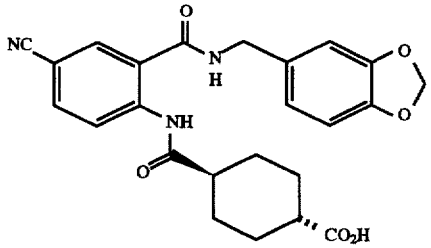

The title compound was obtained as a white needle in a similar manner to that of Example 110 (yield: 26%).

M.P.: 238° to 241° C. (dec.)

MASS: 450(MH⁺)

$^1$H-NMR(400 MHz, DMSO-d$_6$) δ:
1.32–1.48(4H, m), 1.89–2.03(4H, m), 2.19(1H, m), 2.31(1H, m), 4.40(2H, d, J=5.7 Hz), 5.99(2H, s), 8.83(1H, dd, J=7.9, 1.5 Hz), 6.87(1H, d, J=7.9 Hz), 6.95(1H, d, J=1.5 Hz), 7.98(1H, dd, J=8.8, 2.0 Hz), 8.26(1H, d, J=2.0 Hz), 8.60(1H, d, J=8.8 Hz), 9.40(1H, t, J=5.7 Hz), 11.61(1H, s), 12.09(1H, s)

EXAMPLE 129

5-Bromo-2-[(trans-4-carboxycyclohexanecarbonyl)amino]-4-methoxy-N-(3,4-methylenedioxybenzyl)benzamide

102

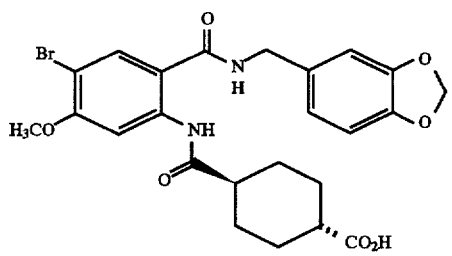

The title compound was obtained as a white needle in a similar manner to that of Example 110 (yield: 26%).

M.P.: 245° to 249° C.

MASS: 533 (MH⁺)

$^1$H-NMR(400 MHz, DMSO-d$_6$) δ:
1.32–1.50(4H, m), 1.90–2.18(1H, m), 2.26(1H, m), 3.87(3H, s), 4.37(2H, d, J=5.7 Hz), 5.99(2H, s), 6.80(1H, dd, J=7.9, 1.6 Hz), 6.86(1H, d, J=7.9 Hz), 6.91(1H, d, J=1.6 Hz), 8.10(1H, s), 8.42(1H, s), 9.21(1H, t, J=5.7 Hz), 11.96(1H, s), 12.01(1H, s)

EXAMPLE 130

5-Chloro-2-(2,5-dimethoxyphenylacetamido)-N-(3,4-methylenedioxybenzyl)benzamide

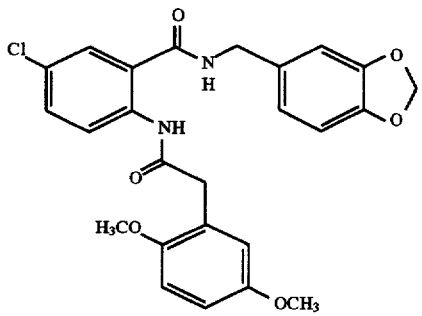

The title compound was obtained as a whitecrystal in a similar manner to that of Example 84 (yield: 55%).

MASS: 483(MH)

$^1$H-NMR(400MHz, DMSO-d$_6$) δ:
3.60(2H, s), 3.68(3H, s), 3.71(3H, s), 4.32(2H, d, J=5.9 Hz), 6.00(2H, s), 6.77–6.94(6H, m), 7.53(1H, dd, J=8.6, 2.2 Hz), 9.26(1H, t, J=5.9 Hz), 11.08(1H, s)

EXAMPLE 131

5-Chloro-2-(2,5-dimethoxybenzamido)-N-(3,4-methylenedioxybenzamide

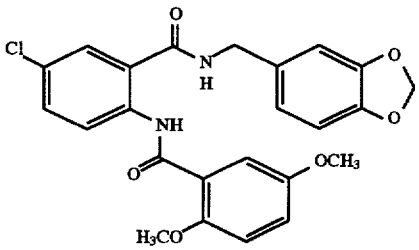

The title compound was obtained as a white crystal in a similar manner to that of Example 34 (yield: 56%).

MASS: 469(MH⁺)

¹H-NMR(400 MHz, CDCl₃) δ:
3.84(3H, s), 4.04(3H, s), 4.52(2H, d, J=5.7 Hz), 5.94(2H, s), 6.34(1H, t, J=5.7 Hz), 6.73–6.84(3H, m), 6.95(1H, d, J=9.0 Hz), 7.06(1H, dd, J=3.1, 9.0 Hz), 7.38–7.44(2H, m), 7.77(1H, d, J=3.1 Hz), 11.71(1H, s)

EXAMPLE 132

4-Amino-5-bromo-2-[(isonicotinoyl)amino]-N-(3,4-methylenedioxybenzyl)benzamide

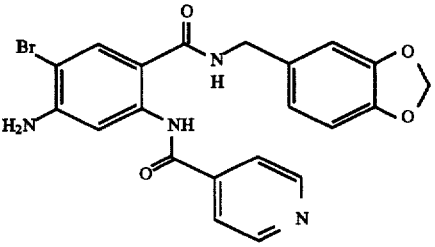

The title compound was obtained as a light-brown crystal in a similar manner to that of Example 34 (yield: 78%).

¹H-NMR(400 MHz, DMSO-d₆) δ:
4.38(2H, d, J=5.7 Hz), 5.98(2H, s), 6.19(2H, br s), 6.80(1H, dd, J=1.6, 7.9 Hz), 6.86(H, d, J=7.9), 6.91(1H, d, J=1.6 Hz), 7.80(2H, d, J=5.9 Hz), 8.05(1H, s), 8.22(1H, s), 8.84(2H, d, J=5.9 Hz), 9.10(1H, t, J=5.7 Hz), 13.35(1H, s)

EXAMPLE 133

4-Amino-5-bromo-2-[(4-tert-butylbenzenesulfonyl)amino]-N-(3,4-methylenedioxybenzyl)benzamide

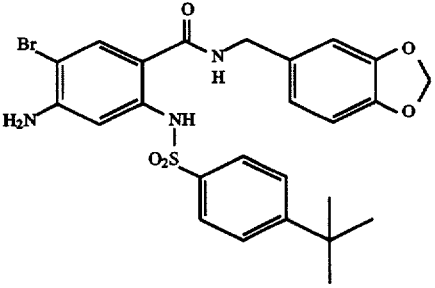

The title compound was obtained as a white powdery crystal in a similar manner to that of Example 34 (yield: 79%).

M.P.: 234° to 235° C.

¹H-NMR(400 MHz, DMSO-d₆) δ:
1.25(9H, s), 4.28(2H, d, J=5.8 Hz), 6.00(2H, br s), 6.78(1H, dd J=1.6, 8.1 Hz), 6.87(1H, d, J=1.6 Hz), 6.88(1H, d, J=8.1 Hz), 7.00(1H s), 7.49–7.54(2H, m), 7.66–7.71(2H, m), 7.86(1H s), 8.97(1H, t, J=5.8 Hz), 12.68(1H, s)

EXAMPLE 134

4-Amino-5-bromo-2-(methanesulfonyl)amino-N-(3,4-methylenedioxybenzyl)benzamide

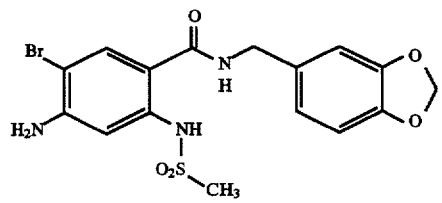

The title compound was obtained as a white crystal in a similar manner to that of Example 34 (yield: 41%).

M.P.: 178° to 180° C.

¹H-NMR(400 MHz, DMSO-d₆) δ:
3.08(3H, s), 3.83(3H, s), 4.33(2H, d, J=5.7 Hz), 6.17(2H, br s), 6.94(1H, s), 7.11(1H, d, J=8.6 Hz), 7.25(1H, dd, J=2.0, 8.6 Hz), 7.36(1H, d, J=2.0 Hz), 8.00(1H, s), 9.07(1H, t, J=5.7 Hz), 11.80(1H, s)

EXAMPLE 135

5-Bromo-2-(methanesulfonyl)amino-N-(3,4-methylenedioxybenzyl)benzamide

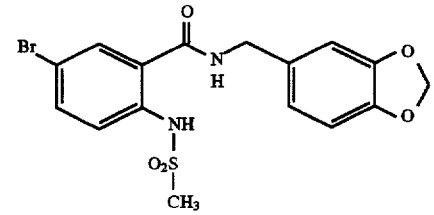

The title compound was obtained as a white crystal in a similar manner to that of Example 34 (yield: 69%).

M.P.: 172° to 173° C.

¹H-NMR(400 MHz, DMSO-d₆) δ:
4.31(2H, d, J=5.9 Hz), 6.77(1H, dd, J=1.6 Hz, 7.9 Hz), 8.87(1H, d, J=1.6 Hz), 6.89(1H, d, J=7.9 Hz), 7.45–7.55 (3H, m), 7.60–7.74(4H, m), 9.33(1H, m), 11.58(1H, s)

EXAMPLE 136

N-(3-Chloro-4-methoxybenzyl)-5-cyano-2-[((S)-5-oxo-2-tetrahydrofurancarbonyl)amino]benzamide

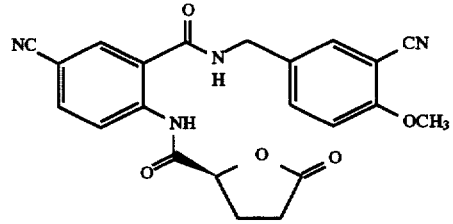

The title compound was obtained as a white crystal in a similar manner to that of Example 34 (yield: 24%).

¹H-NMR(400 MHz, DMSO-d₆) δ:
2.23–2.35(1H, m), 2.52–2.63(3H, m), 3.84(3H, s), 4.43(2H, d, J=5.7 Hz), 5.12–5.17(1H, m), 7.12(1H, d, J=8.6 Hz), 7.32(1H, dd, J=8.0, 2.4 Hz), 7.43(1H, d, J=2.4 Hz), 8.00(1H, dd, J=1.6, 8.9 Hz), 8.30(1H, d, J=1.6 Hz), 8.60(1H, d, J=8.9 Hz), 9.41(1H, t, J=5.7 Hz), 12.02(1H, s)

EXAMPLE 137

N-(3-Chloro-4-methoxybenzyl)-5-cyano-2-[((R)-5-oxo-2-tetrahydrofurancarbonyl)amino]benzamide

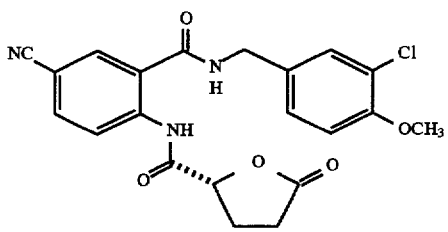

The title compound was obtained as a white crystal in a similar manner to hat of Example 34 (yield: 42%).

M.P.: 231° to 232° C.

¹H-NMR(400 MHz, DMSO-d₆) δ:
2.23–2.35(1H, m), 2.52–2.63(3H, m), 3.84(3H, s), 4.43(2H, d, J=5.7 Hz), 5.12–5.17(1H, m), 7.12(1H, d, J=8.6 Hz), 7.32(1H, dd, J=8.0, 2.4 Hz), 7.43(1H, d, J=2.4 Hz), 8.00(1H, dd, J=1.6, 8.9 Hz), 8.30(1H, d, J=1.6 Hz), 8.60(1H, d, J=8.9 Hz), 9.41(1H, t, J=5.7 Hz), 12.02(1H, s)

EXAMPLE 138

4-Amino-5-bromo-2-[[trans-4-(ethoxycarbonyl)cyclohexanecarbonyl]amino]-N-(3,4-methylenedioxybenzyl)benzamide

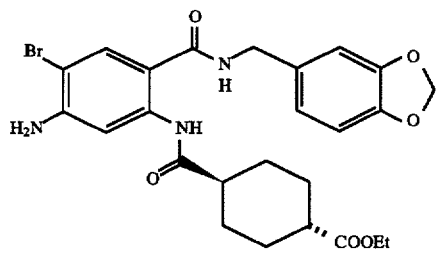

The title compound as obtained as a white crystal in a similar manner to that of Example 4 (yield: 59%).

¹H-NMR(400 MHz, CDCl₃) δ:
1.26(3H, t, J=7.1 Hz), 1.44–1.64(4H, m), 2.06–2.14(4H, m), 2.25–2.36(2H, m), 4.13(2H, q, J=7.1 Hz), 4.42–4.49(4H, m), 5.97(2H, s), 6.30(1H, t, J=5.5 Hz), 5.97(2H, s), 6.83(1H, s), 7.49(1H, s), 8.20(1H, s), 11.57(1H, s)

EXAMPLE 139

4-Amino-5-bromo-N-(3-chloro-4-methoxybenzyl)-2-[[trans-4-(ethoxycarbonyl)cyclohexanecarbonyl]amino]benzamide

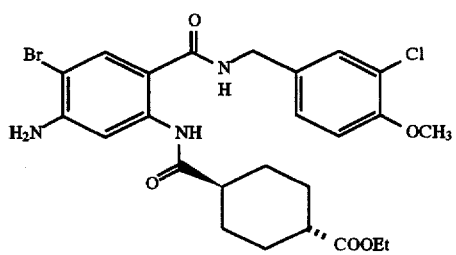

The title compound was obtained as a white crystal in a similar manner to that of Example 84 (yield: 67%).

¹H-NMR(400 MHz, DMSO-d₆) δ:
1.28(8H, t, J=7.1 Hz), 1.42–1.64(4H, m), 2.24–2.87(2H, m), 8.91(8H, s), 4.13(2H, q, J=7.1 Hz), 4.46(2H, br s), 4.49 (2H, d, J=5.6 Hz), 6.30(1H, t, J=5.6 Hz), 6.92(1H, d, J=8.4 Hz), 7.20(1H, dd, J=2.2, 8.4 Hz), 7.87(1H, d, J=2.2 Hz), 7.49(1H, s), 8.21(1H, s), 11.54(1H, s)

EXAMPLE 140

4-Amino-5-bromo-2-[(trans-4-carboxycyclohexanecarbonyl)amino]-N-(3,4-methylenedioxybenzyl)benzamide

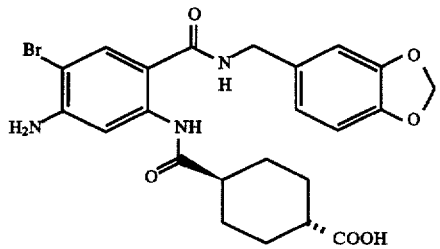

The title compound was obtained as a white crystal in a similar manner to that of Example 34 (yield: 75%).

¹H-NMR(400 MHz, DMSO-d₆) δ:
1.30–1.47(4H, m), 1.90–1.99(4H, m), 2.13–2.24(2H, m), 4.33(2H, d, J=5.6 Hz), 5.98(2H, s), 6.00(2H, br s), 6.77 (1H, dd, J=1.6, 8.1 Hz), 6.88(1H, d, J=1.6 Hz), 7.90(1H, s), 8.04(1H, s), 8.95(1H, t, J=4.0 Hz), 11.93(1H, s)

EXAMPLE 141

4-Amino-5-bromo-2-[(trans-4-carboxycyclohexanecarbonyl)amino]-N-(3-chloro-4-methoxybenzyl)benzamide

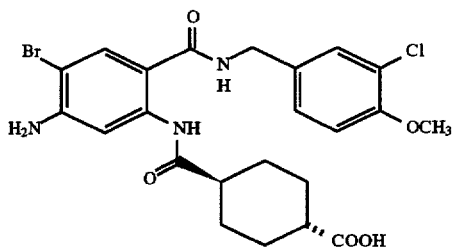

The title compound was obtained as a white crystal in a similar manner to that of Example 34 (yield: 64%).

M.P.: 274° to 276° C.

¹H-NMR(400 MHz, DMSO-d₆) δ:
1.30–1.47(4H, m), 1.90–1.98(4H, m), 2.12–2.23(2H, m), 3.83(3H, s), 4.35(2H, d, J=5.6 Hz), 6.01(2H, br s), 7.11 (1H, d, J=8.6 Hz), 7.25(1H, dd, J=8.6, 2.2 Hz), 7.36(1H, d, J=2.2 Hz), 7.90(1H, s), 8.03(1H, s), 8.98(1H, t, J=5.4 Hz), 11.89(1H, s)

EXAMPLE 142

2-[((R)-4-Carbamoyl-2-hydroxybutyryl)amino]-N-(3-chloro-4-methoxybenzyl)-5-cyanobenzamide

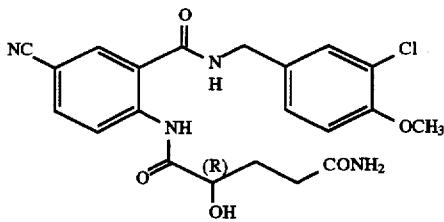

N-(3-Chloro-4-methoxybenzyl)-5-cyano-2-[((R)-5-oxo-2-tetrahydrofurancarbonyl)amino]benzamide (500 mg) was dissolved in 2.5 ml of 1,4-dioxane, followed by the addition of 2.5 ml of concentrated aqueous ammonia. The obtained mixture was heated under reflux for 2 hours and concentrated. The residue was purified by silica gel column chromatography (solvent: ethyl acetate) to give 150 mg of the title compound as a white crystal (yield: 29%).

M.P.: 168° to 170° C.

$^1$H-NMR(400 MHz, DMSO-$d_6$) δ:
1.68–1.80(1H, m), 1.95–2.05(1H, m), 2.12–2.30(2H, m), 3.84(3H, s), 4.05–4.13(1H, m), 4.40–4.47(2H, m), 6.35 (1H, br s), 6.79(1H br s), 7.09–7.15(1H, m), 7.29–7.42 (2H, m), 7.43(1H, d, J=2.0 Hz), 7.96(1H, dd, J=2.0, 8.8 Hz), 8.27(1H, d, J=2.0 Hz), 8.77(1H, d, J=8.8 Hz), 9.40(1H, t, J=5.7 Hz),

EXAMPLE 143

2,4-Diamino-N-(3,4-methylenedioxybenzyl)benzamide

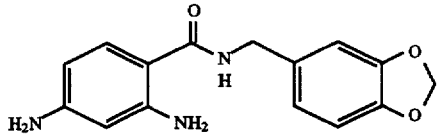

4-Nitroanthranilic acid (7.0 g), piperonylamine (6.42 g), N,N'-dicyclohexylcarbodiimide (8.78 g), and 1-hydroxybenztriazole (5.75 g) were added to 500 ml of acetonitrile. The obtained mixture was heated at 60° C. for 3 hours, cooled and filtered to remove formed crystals. The filtrate was concentrated and extracted with ethyl acetate. The ethyl acetate phase was distilled to remove the solvent, giving crude crystals. Ethanol (50 ml), N,N-dimethylformamide (50 ml) and platinum oxide (50 mg) were added to the formed crystals. The obtained mixture was subjected to catalytic hydrogenation under an elevated pressure at room temperature for 2 hours. The resulting reaction mixture was freed from the catalyst by filtration, and distilled to remove the solvent. Dichloromethane was added to the residue to conduct crystallization. The formed crystals were recovered by filtration and dried to give 4.83 g of the title compound as a gray crystal (yield: 42%).

M.P.: 180° to 182° C.

$^1$H-NMR(400 MHz, DMSO-$d_6$) δ:
4.25(2H, d, J=8.0), 5.28(2H, s), 5.78–5.80(2H, m), 5.96(2H, s), 6.39(2H, s), 6.81–6.86(2H, m), 7.28(1H, d, J=9.2 Hz)., 8.21(1H, t, J=6.0 Hz)

EXAMPLE 144

5-Bromo-2,4-diamino-N-(3,4-methylenedioxybenzyl) benzamide

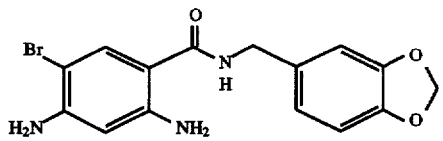

2,4-Diamino-N-(3,4-methylenedioxybenzyl)benzamide (6.47 g) was suspended in 50 ml of ethanol, followed by the gradual addition of 3 ml of 47% aqueous hydrobromic acid. After the completion of the precipitation of white crystals, the solvent was completely distilled off in a vacuum. Dimethyl sulfoxide (30 ml) was added to the residue and the obtained mixture was heated at 150° C. under stirring for one hour and distilled in a vacuum to remove the dimethyl sulfoxide. The residue was purified by silica gel column chromatography (solvent: toluene/ethyl acetate (1: 1)) to give 1.80 g of the title compound as a white crystal (yield: 22%).

M.P.: 148° to 150° C.

$^1$H-NMR(400 MHz, DMSO-$d_6$) δ:
4.25(2H, d, J=5.9 Hz), 5.45(2H, s), 5.97(2H, s), 8.02(1H, s), 8.49(2H, s), 8.74(1H, dd, J=1.8, 8.1 Hz), 8.82–8.88(2H, m), 7.82(1H, s), 8.44(1H, t, J=5.9 Hz),

We claim:

1. An anthranilic acid derivative represented by the general formula (I) or a pharmacologically acceptable salt thereof:

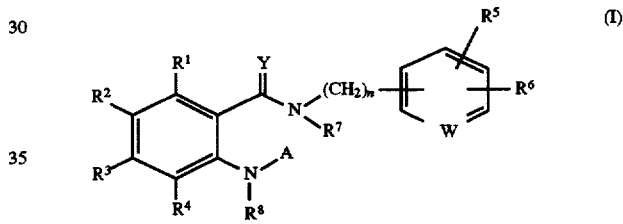

wherein $R^1$, $R^2$, $R^3$ and $R^4$ represent the same or different from each other, a hydrogen atom, a halogen atom, a hydroxy group, an optionally halogenated lower alkyl group, an optionally halogenated lower alkoxy group, a nitro group, a hydroxyalkyl group, a cyano group, a group of the formula:

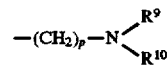

wherein $R^9$ and $R^{10}$ represent the same or different from each other, a hydrogen atom, an optionally halogenated lower alkyl group, an arylalkyl group, a heteroarylalkyl group, an acyl group or an optionally protected carboxyl group, or alternatively $R^9$ and $R^{10}$ together with the nitrogen atom to which they are bonded may form a ring which may be substituted; and p is an integer of 0 to 6, an optionally substituted tetrazolyl group, an optionally protected carboxyl group, an optionally substituted carbamoyl group, an optionally substituted pyrazolyl group, an optionally substituted imidazolyl group, a group of the formula:

(wherein $R^{13}$ represents a hydrogen group or an optionally halogenated lower alkyl group; and q is an integer of 0 to 2, or alternatively two substituents selected from among $R^1$, $R^2$, $R^3$ and $R^4$ which are adjacent to each other may form a ring together with the carbon atoms to which they are bonded respectively;

R$^5$ and R$^6$ represent the same or different from each other, a hydrogen atom, a halogen atom, a hydroxy group, a cyano group, an optionally halogenated lower alkyl group or an optionally halogenated lower alkoxy group, or alternatively R$^5$ and R$^6$ together with the carbon atoms to which they are bonded respectively may form a cycloalkyl ring, an oxolane ring, a 1,3-dioxolane ring or a 1,4-dioxane ring;

W represents a group of the formula: —N= or —CH=; R$^7$ and R$^8$ represent the same or different from each other, a hydrogen atom or an optionally halogenated lower alkyl group, or alternatively R$^1$ and R$^7$ together with the carbon atoms to which they are bonded respectively may form a ring which may contain a nitrogen atom, an oxygen atom or a sulfur atom and which may be substituted;

A represents a hydrogen atom, an optionally halogenated lower alkyl group or a group of the formula: —X—(CH$_2$)$_m$—Z wherein X represents —CO—, —CS—, —CH$_2$— or —S(O)$_2$—;

Z represents a hydroxy group, an optionally halogenated lower alkoxy group, a cyano group, a halogen atom, an optionally protected carbamoyl group, an optionally substituted aryl group, an optionally substituted aryloxy group, an optionally substituted heteroaryl group, an optionally substituted heteroarylalkyloxy group, a group of the formula: —NR$^{11}$R$^{12}$ wherein R$^{11}$ and R$^{12}$ represent the same or different from each other, a hydrogen atom, an optionally halogenated lower alkyl group, an optionally substituted arylalkyl group, an optionally substituted heteroarylalkyl group, an acyl group, an optionally protected carboxy group or an optionally substituted carbamoyl group, or alternatively R$^{11}$ and R$^{12}$ together with the nitrogen atom to which they are bonded may form a ring which may be substituted, or an optionally substituted cycloalkyl group; and m is an integer of 0 to 6;

Y represents an oxygen atom or a sulfur atom; and n is an integer of 0 to 6.

2. An anthranilic acid derivative or pharmacologically acceptable salt thereof as set forth in claim 1, wherein Y is an oxygen atom.

3. A preventive and therapeutic agent for diseases wherein a phosphodiesterase inhibitory action is efficacious, which comprises an anthranilic acid derivative or pharmacologically acceptable salt thereof as set forth in claim 1 as an active ingredient.

4. A preventive and therapeutic agent for diseases wherein a cyclic GMP phosphodiesterase inhibitory action is efficacious, which comprises an anthranilic acid derivative or pharmacologically acceptable salt thereof as set forth in claim 1 as an active ingredient.

5. A preventive and therapeutic agent as set forth in claim 4, wherein said diseases include ischemic heart diseases, angina pectoris, hypertension, pulmonary hypertension, heart failure and asthma.

6. A drug composition comprising a pharmacologically effective amount of an anthranilic acid derivative or pharmacologically acceptable salt thereof as set forth in claim 1, and a pharmacologically acceptable carrier.

7. A method for the prevention and treatment of diseases, which comprises administering a pharmacologically effective amount of an anthranilic acid derivative or pharmacologically acceptable salt thereof as set forth in claim 1 to inhibit phosphodiesterase.

* * * * *